US007592319B2

(12) United States Patent
Li et al.

(10) Patent No.: US 7,592,319 B2
(45) Date of Patent: Sep. 22, 2009

(54) USES OF DNA-PK

(75) Inventors: Gloria C. Li, New York, NY (US); Paul W. J. J. Burgman, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 98 days.

(21) Appl. No.: 10/712,642

(22) Filed: Nov. 12, 2003

(65) Prior Publication Data

US 2005/0032726 A1  Feb. 10, 2005

Related U.S. Application Data

(63) Continuation of application No. 09/750,410, filed on Dec. 28, 2000, which is a continuation of application No. PCT/US99/14702, filed on Jun. 30, 1999.

(60) Provisional application No. 60/091,181, filed on Jun. 30, 1998.

(51) Int. Cl.
*A01N 43/04* (2006.01)
*A01N 61/00* (2006.01)
*C12Q 1/68* (2006.01)
*C12N 15/63* (2006.01)
*C07H 21/04* (2006.01)

(52) U.S. Cl. .............................. 514/44; 435/6; 435/91.1; 435/320.1; 435/455; 514/1; 514/2; 536/23.1; 536/24.5

(58) Field of Classification Search ................ 435/6, 435/91.1, 91.31, 455, 458, 375, 320.1; 514/44, 514/1, 2; 536/23.1, 24.5
See application file for complete search history.

(56) References Cited

U.S. PATENT DOCUMENTS 5,641,754 A    6/1997  Iversen
5,773,580 A *  6/1998  Au-Young et al. .......... 530/350

FOREIGN PATENT DOCUMENTS

WO    WO 97/08184    3/1997
WO    WO 9708184     3/1997

OTHER PUBLICATIONS

Takiguchi et al., Genomics, vol. 35, pp. 129-135 (1996).*
Reeves et al., J. Biol. Chem., vol. 264, No. 9, pp. 5047-5052 (1989).*
Milner et al., Nature Biotech., vol. 15, pp. 537-541 (1997).*
Peracchi et al., Rev. Med. Virol., vol. 14, pp. 47-64 (2004).*
Agrawal et al., Molecular Med. Today, vol. 6, pp. 72-81 (2000).*
Branch, A.D., Trends in Biochem. Sci., vol. 23, pp. 45-50 (1998).*
Chirila et al., Biomaterials, vol. 23, pp. 321-342 (2002).*
Crooke, S.T., Antisense Res. & Application, Chapter 1, pp. 1-50, Ed. by S. Crooke, Publ. by Springer-Verlag (1998).*
Reed, J.C. et al., Proc. Natl. Acad. Sci., vol. 87, pp. 3660-3664 (1990).*

Amiel, J. et al., (1996), Heterozygous Endothelin Receptor B (EDNRB) Mutations In Isolated Hirschsprung Disease, *Human Molecular Genetics*, 5 (3), pp. 355-357.
Anderson, C.W., (1993), Dna Damage And The Dna-Activated Protein Kinase, *Tibs*, 18, pp. 433-437.
Angrist, M., et al., (1995), Mutation Analysis Of The RET Receptor Tyrosine Kinase In Hirschsprung Disease, *Human Molecular Genetics*, vol. 4 (5), pp. 821-830.
Araki, R., et al., (1997), Nonsense Mutation At Tyr-4046 In The DNA-Dependent Protein Kinase Catalytic Subunit Of Server Combined Immune Deficiency Mice, *Proc. Natl. Acad. Sci. USA*, 94, pp. 2438-2443.
Attie, T., et al., (1995), Diversity Of RET Proto-Oncogene Mutations In Familial And Sporadic Hirschsprung Disease, *Human Molecular Genetics*, 4 (8), pp. 1381-1386.
Badner, J., et al., (1990), A Genetic Study Of Hirschsprung Disease, *Am. J. Hum. Genet.*, 46, pp. 568-580.
Barlow, C., et al., (1996), Atm-Deficient Mice: A Paradigm Of Ataxia Telangiectasia, *Cell*, 86, pp. 179-171.
Biederman, K., et al., (1991), *Scid* Mutation In Mice Confers Hypersensitivity To Ionizing Radiation And A Deficiency In DNA Double-Strand Break Repair, *Proc. Natl. Acad. Sci.*, 88, pp. 1394-1397.
Bird, R., (1995), Role Of Aberrant Crypt Foci In Understanding The Pathogenesis Of Colon Cancer, *Cancer Letters*, 93, pp. 55-71.

(Continued)

*Primary Examiner*—Jane Zara
(74) *Attorney, Agent, or Firm*—John P. White; Cooper & Dunham LLP

(57) ABSTRACT

This invention provides a method for increasing the susceptibility of a cell to DNA-damaging agents, comprising introducing into the cell an antisense oligonucleotide that specifically hybridizes to a nucleic acid encoding a DNA dependent protein kinase subunit so as to prevent expression of the DNA dependent protein kinase subunit; wherein the antisense oligonucleotide is in an amount sufficient to increase the sensitivity of the cell to heat, chemical, or radiation-induced DNA damage; and wherein the DNA dependent protein kinase subunit is a DNA dependent protein kinase catalytic subunit, a Ku70, or a Ku80. This invention also provides a method of treating a tumor in a subject, comprising administering to the subject an antisense oligonucleotide that specifically hybridizes to a nucleic acid encoding a DNA dependent protein kinase subunit so as to prevent expression of the DNA dependent protein kinase subunit; wherein the antisense oligonucleotide is in an amount sufficient to increase the sensitivity of the tumor to heat, chemical, or radiation-induced DNA damage; and wherein the DNA dependent protein kinase subunit is a DNA dependent protein kinase catalytic subunit, a Ku70, or a Ku80. This invention provides an antisense oligonucleotide that specifically hybridizes to a nucleic acid encoding a DNA dependent protein kinase subunit, wherein the DNA dependent protein kinase subunit is a DNA, dependent protein kinase catalytic subunit, Ku70, or Ku80, so as to prevent expression of the DNA dependent protein kinase subunit.

10 Claims, 31 Drawing Sheets

OTHER PUBLICATIONS

Blunt, T., et al., (1995), Defective DNA-Dependent Protein Kinase Activity Is Linked To V(D)J Recombination And DNA Repair Defects Associated With The Murine Scid Mutation, *Cell*, 80, pp. 813-823.

Blunt, T., et al., (1996), Identification Of A Nonsense Mutation In The Carboxyl-Terminal Region Of DNA-Dependent Protein Kinase Catalytic Subunit In The *Scid* Mouse, *Proc. Natl. Acad. Sci.*, 93, pp. 10285-10290.

Boder, Elena (1975), Ataxia-Telangiectasia: Some Historic, Clinical And Pathologic Observations, *Birth Defects: Original Article Series*, XI, (1), pp. 255-270.

Bogue, M., et al., (1996), Mechanism Of V(D)J Recombination, *Current Opinion In Immunology*, 8, pp. 175-180.

Bogue, M., et al., (1996), P53 Is Required For Both Radiation-Induced Differentiation And Rescue Of V(D)J Rearrangement In Scid Mouse Thymocytes, *Genes & Development*, 10 pp. 553-565.

Bosma, G., et al., (1983), A Severe Combined Immunodeficiency Mutation In The Mouse, *Nature*, 301 (10), pp. 527-530.

Bosma, M.J., et al., (1991), The SCID Mouse Mutant: Definition, Characterization, And Potential Uses, *Ann. Rev. Immunol.*, 9, pp. 323-350.

Boubnov, N., et al., (1995), Complementation Of The Ionizing Radiation Sensitivity, DNA End Binding, And V(D)J Recombination Defects Of Double-Strand Break Repair Mutants By The P86 Ku Autantigen, *Proc. Natl. Acad. Sci.*, 92, pp. 890-894.

Cai, Q.Q., et al., (1994), Chromosomal Location And Expression Of The Genes Coding For Ku P70 And P80 In Human Cell Lines And Normal Tissues, *Cytogenet Cell Genet*, 65, pp. 221-227.

Carroll, A.M., et al., (1989) Occurence Of Mature B (IGM, B220) And T (CD#) Lymphocytes In Scid Mice, *Journal Of Immunology*, 143, pp. 1087-1093.

Carroll, A.M., et al., (1991), T-Lymphocyte Development In Scid Mice Is Arrested Shortly After The Initiation Of T-Cell Receptor Δ Gene Recombination, *Genes & Development*, vol. 5, pp. 1357-1366.

Carter, T., et al., (1990), A DNA-Activated Protein Kinase From Hela Cell Nuclei, *Molecular And Cellular Biology*, 10(12), pp. 6460-6471.

Chan, D.W., et al., (1996), The DNA-Dependent Protein Kinase Is Inactivated By Autophosphorylation Of The Catalytic Subunit, *Journal Of Biological Chemistry*, 271 (15), pp. 8939-8941.

Chou, C.H., et al., (1992), Role Of A Major Autoepitope In Forming The DNA Binding Site Of The P70 (Ku) Antigen, *J. Exp. Med.*, 175, pp. 1677-1684.

Cordon-Cardo, C., et al., (1994), Expression Of The Retinoblastoma Protein Is Regulated In Normal Human Tissue, *American Journal Of Pathology*, 144, pp. 500-510.

Costa, T.E., et al., (1992), Chromosomal Position Of Rearranging Gene Segments Influences Allelic Exclusion In Transgenic Mice, *Proc. Natl. Acad. Sci.*, 89, pp. 2205-2208.

Custer, R.P., et al., (1985), Severe Combined Immunodeficiency (SCID) In The Mouse, *Am. J. Pathol.*, 120, pp. 464-477.

Dalbagni, G., et al., (1993), Molecular Genetic Alterations Of Chromosome 17 And P53 Nuclear Overexpression In Human Bladder Cancer, *Diagnostic Molecular Pathology*, 2(1), pp. 4-13.

Danska, J.S., et al., (1994), Rescue Of T-Cell Specific V(D)J Recombination In SCID Mice By DNA-Damaging Agents, *Science*, 266, pp. 450-455.

Donehower, L., et al., (1992), Mice Deficient For P53 Are Developmentally Normal But Susceptible To Spontaneous Tumors, *Nature*, 356, pp. 215-221.

Dvir, A. et al., (1992), Ku Autoantigen Is The Regulatory Component Of A Template-Associated Protein Kinase That Phosphorylates RNA Polymerase II, *Proc. Natl. Acad. Sci.*, 89, pp. 11920-11924.

Dyson, N. et al., (1989), The Human Papilloma Virus-16 E7 Oncoprotein Is Able To Bind To The Retinoblastoma Gene Product, *Science, New Series*, 243, pp. 934-937.

Edery, P., et al., (1996), Mutation Of The Endothelin-3 Gene In The Waardenburg-Hirschsprung Disease (Shah-Waardenburg Syndrome), *Nature Genetics*, 12, pp. 442-444.

Fulop, G.M., et al., (1990), The Scid Mutation In Mice Causes A General Defect In Dna Repair, *Nature*, 347, pp. 479-482.

Gao, Y., et al., (1998), A Targeted Dna-Pkcs-Null Mutation Reveals Dna-Pk-Independent Functions For Ku In V(D)J Recombination, *Immunity*, 9, pp. 367-376.

Gonzalez-Zuleta, M., et al., (1995), Methylation Of The 5' Cpg Island Of The P16/Cdkn2 Tumor Suppressor Gene In Normal And Transformed Human Tissues Correlates With Gene Silencing, *Cancer Research*, 55, pp. 4531-4535.

Gottlieb, T.M., et al., (1993), The DNA-Dependent Protein Kinase: Requirement For DNA Ends And Association With Ku Antigen, *Cell*, 72, pp. 131-142.

Gu, Y., et al., (1997), Growth Retardation And Leaky SCID Phenotype Of Ku70-Deficient Mice, *Immunity*, 7, pp. 653-665.

Hammarsten, O. et al., (1998), DNA-Dependent Protein Kianse: DNA Binding And Activation In The Absence Of Ku, *Proc. Natl. Acad. Sci.*, 95, pp. 525-530.

Hendrickson, E.A. et al., (1991), A Link Between Double-Strand Break-Related Repair And V(D)J Recombination: The Scid Mutation, *Proc. Natl. Acad. Sci.*, 88, pp. 4061-4065.

Hofstra, R., et al., (1996), A Homozygous Mutation In The Endothelin-3 Gene Associated With A Combined Waardenburg Type 2 And Hirschsprung Phenotype (Shah-Waardenburg Syndrome), *Nature Genetics*, 12, pp. 445-447.

Iliakis, G.E., et al., (1991), Detection Of DNA Double-Strand Breaks In Synchronous Cultures Of CHO Cells By Means Of Asymmetric Field Inversion Gel Electrophoresis, *Int. J. Radiat. Biol.*, 59(2), pp. 321-341.

Jacks, T., 1994, Tumor Spectrum Analysis In P53-Mutant Mice, *Current Biology*, 4(1), pp. 1-7.

Jackson, S.P., et al., (1995), DNA Double-Strand Break Repair And V(D)J Recombination: Involvement Of DNA-PK, *TIBS*, 20, pp. 412-415.

Jeggo, P.A., et al., Menage A Trois: Double Strand Break Repair, V(D)J Recombination And DNA-PK, (1995), *Bioessays*, 17 (11), pp. 949-957.

Jhappan, C., et al., (1997), DNA-Pkcs: A T-Cell Tumour Suppressor Encoded At The Mouse *Scid* Locus, *Nature Genetics*, 17, pp. 483-486.

Kim, D., et al., (1995), A Constitutive Heat Shock Element-Binding Factor Is Immunologically Identical To The Ku Autoantigen, *Journal Of Biological Chemistry*, 87, pp. 15277-15284.

Kinzler, K.W., et al., (1996), Lessons From Hereditary Colorectal Cancer, *Cell*, 87, pp. 159-170.

Kirchgessner, C.U., et al., (1995), DNA-Dependent Kinase (P350) As A Candidate Gene For The Murine SCID Defect, *Science*, 267, pp. 1178-1183.

Lees-Miller, S.P., et al., (1995), Absense Of P350 Of DNA-Activated Protein From A Radiosensitive Human Cell Line, *Science*, 267, pp. 1183-1185.

Lees-Miller, S.P., et al., (1996), The DNA-Dependent Protein Kinase, DNA-PK: 10 Years And No Ends In Sight, *Biochem. Cell Biol.*, 74, pp. 503-512.

Li, G.C., et al., (1998) Ku70: A Candidate Tumor Suppressor Gene For Muring T Cell Lymphoma, *Molecular Cell*, 2, pp. 1-8.

Li, Z., et al., (1995) The XRCC4 Gene Encodes A Novel Protein Involved In DNA Double-Strand Break Repair And V(D)J Recombination, *Cell*, 83, pp. 1079-1089.

Liang, F., et al., (1996), Ku80-Deficient Cells Exhibit Excess Degradation Of Extrachromosomal DNA, *Journal Of Biological Chemistry*, 271(24), pp. 14405-14411.

Lieber, M.R., et al., (1998), The Defect In Murine Severe Comined Immune Deficiency: Joining Of Signal Sequences But Not Coding Segments In V(D)J Recombination, *Cell*, 55, pp. 7-16.

Linzer, D.I.H., et al., (1979), Characterization Of A 54K Dalton Cellular SV40 Tumor Antigen Present In SV40-Transformed Cells And Uninfected Embryonal Carcinoma Cells, *Cell*, 17, pp. 43-52.

Little, J.B., (1979), Quantitative Studies Of Radiation Transformation With The A31-11 Mouse BALB/3T3 Cell Line, *Cancer Research*, 39, pp. 1474-1480.

Loda, M., et al., (1997), Increased Proteasome-Dependent Degradation Of The Cyclin Dependent Kinase Inhibitor P27 In Aggressive Colorectal Carcinomas, *Nature Medicine*, 3(2), pp. 231-234.

Macpherson, I., (1973), Soft Agar Techniques. In Tissue Culture Methods And Applications, P.F. Kruse Jr. Eds. (New York Academic Press) Chapter 7, pp. 276-280.

Merlo, A., (1995), 5' Cpg Island Methylation Is Associated With Transcriptional Silencing Of The Tumour Suppressor P16/CDKN2/MTS1 In Human Cancers, *Nature Medicine*, (7), pp. 686-692.

Mimori, T., et al., (1981), Characterization Of A High Molecular Weight Acidic Nuclear Protein Recognized By Autoantibodies In Sera From Patients With Polymyositis-Scleroderma Overlap, *J. Clin. Invest.*, 68, pp. 611-620.

Moen, C.J.A., et al., (1996), Different Genetic Susceptibility To Aberrant Crypts And Colon Adenomas In Mice, *Cancer Research*, 56, pp. 2382-2386.

Nagasawa, H., et al., (1979) Effect Of Tumor Promoters, Protease Inhibitors, And Repair Processes On X-Ray-Induced Sister Chromatid Exchanges In Mouse Cells, *Proc. Natl. Acad. Sci.*, 76, pp. 1943-1947.

Nagasawa, H., et al., (1991), Response Of X-Ray-Sensitive CHPO Mutant Cells (Xrs-6c) To Radiation, *Radiation Research*, 126, pp. 280-288.

Nagasawa, H., et al., (1987), Spontaneous Transformation To Anchorage-Independent Growth Of A Xeroderma Pigmentosum Fibroblast Cell Strain, *The Society For Investigative Dermatology, Inc.*, 88, pp. 149-153.

Nussenzweig, A., et al., (1996), Requirement For Ku80 In Growth And Immunoglobulin V(D)J Recombination, *Nature*, 382, pp. 551-555.

Orita, M., et al., (1989), Detection Of Polymorphisms Of Human DNA By Gel Electrophoresis As Single-Strand Conformation Polymorphisms, *Proc. Natl. Acad. Sci.*, 86, pp. 2766-2770.

Ouyang, H., et al., (1997), Ku70 Is Required For DNA Repair But Not For T Cell Antigen Receptor Gene Recombination In Vivo, *J. Exp. Med.*, 186, pp. 921-929.

Pan, Z.Q., et al., (1994), Phosphorylation Of The P34 Subunit Of Human Single-Stranded-DNA Binding Protein In Cyclin A-Activated $G_1$ Extracts Is Catalyzed By Cdk-Cyclin A Complex And DNA-Dependent Protein Kinase, *Proc. Natl. Acad. Sci.*, 91, pp. 8343-8347.

Pavan, W.J., et al., (1995), A High-Resolution Linkage Map Of The Lethal Spotting Locus: A Mouse Model For Hirschsprung Disease, *Mammalian Genonme*, 6, pp. 1-7.

Pergola, F., et al., (1993), V(D)J Recombination In Mammalian Cell Mutants Defective In DNA Double-Strand Break Repair, *Molecular And Cellular Biology*, 13(6), pp. 3464-3471.

Perry, P., et al., (1974), New Giemsa Method For The Differential Staining Of Sister Chromatids, *Nature*, 251, pp. 156-158.

Peterson, S.R. et al., (1997), Characterization Of Two DNA Double-Stranded Break Repair-Deficient Cell Lines That Express Inactive DNA-Dependent Protein Kinase Catalytic Subunits, 272 (15), pp. 10227-10231.

Peterson, S.R., et al., (1995), Loss Of The Catalytic Subunit Of The DNA-Dependent Protein Kinase In DNA Double-Strand-Break-Repair Mutant Mammalian Cells, *Proc. Natl. Acad. Sci.*, 92, pp. 3171-3174.

Peterson, S.R., et al., (1995), Stimulation Of The DNA-Dependent Protein Kinase By RNA Polymerase II Transcriptional Activator Proteins, *J. Bio. Chemistry*, 270(3), pp. 1449-1454.

Pingault, V., et al., (1997), Human Homology And Candidate Genes For The Dominant Megacolon Locus, A Mouse Model Of Hirschsprung Disease, *Genomics*, 39, pp. 86-89.

Ponce-Castaneda, M., et al., (1995), P27$^{kip1}$: Chromosomal Mapping To 12p12-12p13.1 And Absence Of Mutations In Human Tumors, *Cancer Research*, 55, pp. 1211-1214.

Porter, P.L., et al., (1997), Expression Of Cell-Cycle Regulators P27$^{kip1}$ And Cyclin E, Alone And In Combination, Correlate With Survival In Young Breast Cancer Patients, *Nature Medicine*, 3(2), pp. 222-225.

Purdie, C.A., et al., (1994), Tumour Incidence, Spectrum And Ploidy In Mice With A Large Deletion In The P53 Gene, *Oncogene*, 9, pp. 603-609.

Rathmell, W.K., et al., (1994), Involvement Of The Ku Autoantigen In The Cellular Response To DNA Double-Strand Breaks, *Proc. Natl. Acad. Sci.*, 91, pp. 7623-7627.

Roncucci, L., et al., (1993), Cell Kinetic Evaluation Of Human Colonic Aberrant Crypts, *Cancer Research*, 53, pp. 3726-3729.

Roth, D.B., et al., (1993), Characterization Of Broken DNA Molecules Associated With V(D)J Recombination, *Proc. Natl. Acad. Sci. USA*, 90, pp. 10788-10792.

Roth, D.B., et al., (1995), How To Make Ends Meet, *Current Biology*, 5, pp. 496-499.

Sanger, F., et al., (1977), DNA Sequencing With Chain-Terminating Inhibitors, *Proc. Natl. Acad. Sci.*, 74 (12), pp. 5463-5467.

Sarnow, P. et al., (1982), Adenovirus Elb-58kd Tumor Antigen And Sv40 Large Tumor Antigen Are Physically Associated With The Same 54 Kd Cellular Protein In Transformed Cells, *Cell*, 28, pp. 387-394.

Serrano, M., et al., (1996), Role Of The INK4a Locus In Tumor Suppression And Cell Mortality, *Cell*, 85, pp. 27-37.

Sipley, J.D., et al., (1995), Gene For The Catalytic Subunit Of The Human DNA-Activated Protein Kinase Maps To The Site Of The XRCC7 Gene On Chromosome 8, *Proc. Natl. Acad. Sci.*, 92, pp. 7515-7519.

Smider, V., et al., (1994), Restoration Of X-Ray Resistance And V(D)J Recombination In Mutant Cells By Ku Cdna, *Science*, 266, pp. 288-291.

Smith, C.A., et al., (1989), Antibodies To CD3/T-Cell Receptor Complex Induce Death By Apoptosis In Immature T Cells In Thymic Cultures, *Nature*, 337, pp. 181-184.

Southard-Smith, E.M., et al., (1998), Sox10 Mutation Disrupts Neural Crest Development In Dom Hirschsprung Mouse Model, *Nature Genetics*, 18, pp. 60-64.

Strasser, A., et al., (1994), Bcl-2 Expression Promotes B-But Not T-Lymphoid Development In Scid Mice, *Nature*, 368, pp. 457-460.

Suwa, A., et al., (1994), Dna-Dependent Protein Kinase (Ku Protein-P350 Complex) Assembles On Double-Stranded Dna, *Proc. Natl. Acad. Sci. USA*, 91, pp. 6904-6908.

Taccioli, G., et al., (1993), Impairment Of V(D)J Recombination In Double-Strand Break Repair Mutants, *Science*, 260, pp. 207-210.

Taccioli, G., et al., (1994), Ku80: Product Of The Xrcc5 Gene And Its Role In Dna Repair And V(D)J Recombination, *Science*, vol. 265, pp. 1442-1445.

Taccioli, G., et al., (1998), Targeted Disruption Of The Catalytic Subunit Of The Dna-Pk Gene In Mice Confers Severe Combined Immunodeficiency And Radiosensitivity, *Immunity*, 9, pp. 355-366.

Takiguchi, Y., et al., (1996), Genomic Structure And Chromosomal Assignment Of The Mouse Ku70 Gene, *Genomics*, 35, pp. 129-135.

Thompson, L.H., (1995), Nomenclature Of Human Genes Involved In Ionizing Radiation Sensitivity, *Mutation Research*, 337, pp. 131-134.

Tsukada, T., et al., (1993), Enhanced Proliferative Potential In Culture Of Cells From P53-Deficient Mice, *Oncogene*, 8, pp. 3313-3323.

Van Zant, G., et al., (1983), The Effect Of Hyperthermia On Hemopoietic Progenitor Cells Of The Mouse, *Radiation Research*, 95, pp. 142-149.

Vogelstein, B., et al., (1993), The Multistep Nature Of Cancer, *Tig*, 9, pp. 138-141.

Weaver, D.T., et al., (1995), What To Do At An End: Dna Double-Strand-Break Repair, *Tig*, 11, pp. 388-392.

Werness, B.A., et al., (1989), Association Of Human Papillomavirus Types 16 And 18 E6 Proteins With P53, *Science*, 248, pp. 76-79.

Whyte, P., et al., (1988), Association Between An Oncogene And An Anti-Oncogene: The Adenovirus E1A Proteins Bind To The Retinoblastoma Gene Product, *Nature*, 334 (14), pp. 124-129.

Yaneva, M., et al., (1997), Interaction Of DNA-Dependent Protein Kinase With DNA And With Ku: Biochemical And Atomic-Force Microscopy Studies, *The EMBO Journal*, 16, pp. 5098-5112.

Yumoto, Y., et al., (1998), High Mobility Group Proteins 1 And 2 Can Function As DNA-Binding Regulatory Components For DNA-Dependent Protein Kinase In Vitro, *J. Biochem.*, 124, pp. 519-527.

Zhu, C., et al., (1996), Ku86-Deficient Mice Exhibit Severe Combined Immunodeficiency And Defective Processing Of V(D)J Recombination Intermediates, *Cell*, vol. 86, pp. 379-389.

Jackson, Stephen P., DNA-dependent Protein Kinase. *International Journal of Biochemistry & Cell Biology*, (1997) vol. 29, No. 7, pp. 935-938.

Li, Gloria C. et al., Ku70: A Candidate Tumor Suppressor Gene for Murine T Cell Lymphoma. *Molecular Cell*, (Jul. 1998) vol. 2, pp. 1-8.

Shin, Euy Kyun et al., Evaluation of a Test for Identification of Arabian Horses Heterozygous for the Severe Combined Immunodeficiency Trait. *Journal of the American Veterinary Medical Association*, (Nov. 15, 1997) vol. 211, No. 10, pp. 1268-1270.

Tseng, B.Y., and K.D. Brown, Antisense Oligonucleotide Technology in the Development of Cancer Therapeutics. *Cancer Gene Therapy*, (1994) vol. 1, No. 1, pp. 65-71.

Uhlmann, Eugen, and Anusch Peyman, Antisense Oligonucleotides: A New Therapeutic Principle. *Chemical Reviews, American Chemical Society*, (Jun. 1990) vol. 90, No. 4, pp. 543-584.

Gu, Yansong et al., (1997) "Ku70-deficient embryonic stem cells have increased ionizing radiosensitivity, defective DNA end-binding activity, and inability to support V(D)J recombination," Proc. Natl. Acad. Sci. USA, 94:15, pp. 8076-8081.

Jackson, Stephen, (1997) "DNA-dependent protein kinase," Int. J. Biochem. Cell Biol., 29:7, pp. 935-938.

Jin, Shengfang et al., (1998) "Differential etoposide sensitivity of cells deficient in the Ku and DNA-PKcs components of the DNA-dependent protein kinase," Carcinogenesis, 19:6, pp. 965-971.

Ouyang, Honghari et al., (1997) "Ku70 is required for DNA repair but not for T cell antigen receptor gene recombination in vivo," J. Exp. Med, 186:6, pp. 921-929.

Shen, Hongxie et al., (1998) "Increased expression of DNA-dependent protein kinase confers resistance to adriamycin," Biochemica et Biophysica Acta, 1381:2, pp. 131-138.

Tseng, B.Y. et al., (1994) "Antisense oligonucleotide technology in the development of cancer therapeutics," Cancer Gene Therapy, 1:1, pp. 65-71.

Ulmann, Eugen et al., (1990) "Antisense oligonucleotides: a new therapeutic principle," Chemical Reviews, 90:4, pp. 543-584.

* cited by examiner

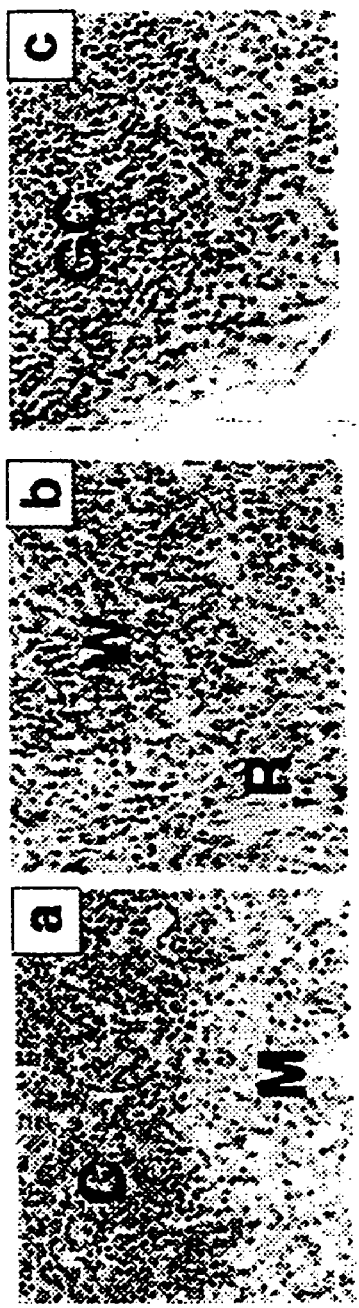
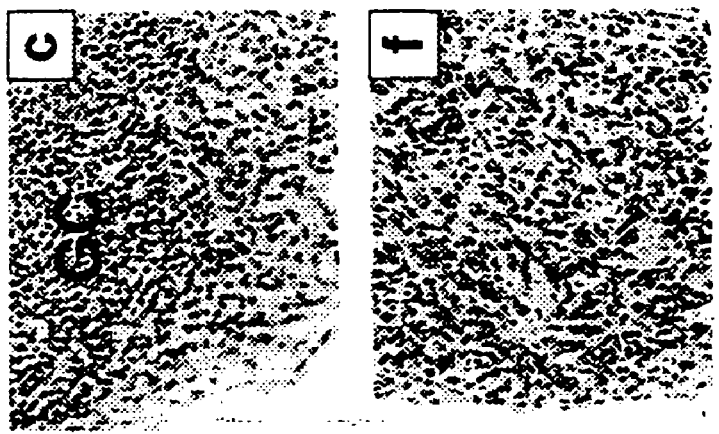
FIG. 2A-1 Thy  FIG. 2A-2 Spl  FIG. 2A-3 LN
FIG. 2A-4     FIG. 2A-5      FIG. 2A-6
wild type (HE)
Ku80-/- (HE)

FIG. 2A-7
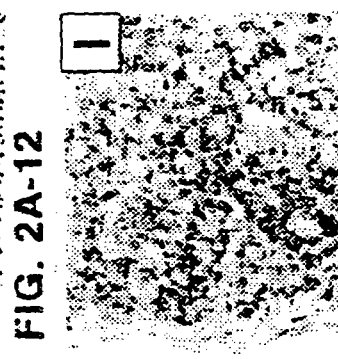
FIG. 2A-8
FIG. 2A-9
FIG. 2A-10
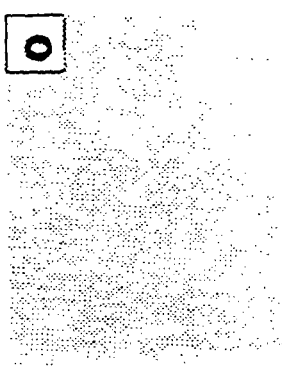
FIG. 2A-11
FIG. 2A-12
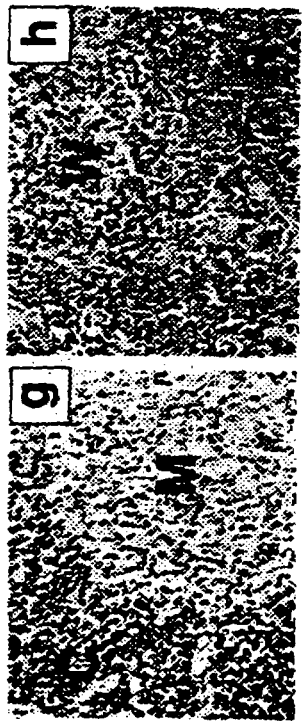
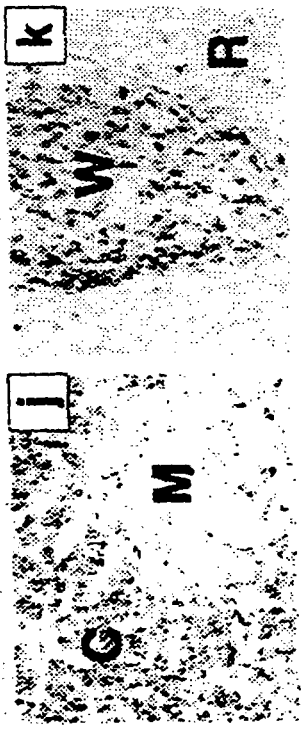
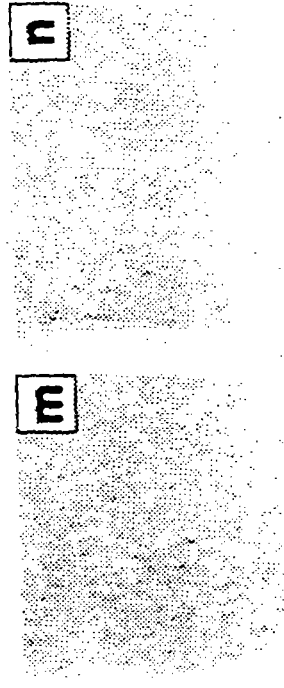
FIG. 2A-13
FIG. 2A-14
FIG. 2A-15
Ku70-/- (HE)
Ku70-/- (CD3)
Ku70-/- (CD19)

FIG. 2C-1  FIG. 2C-2  FIG. 2C-3
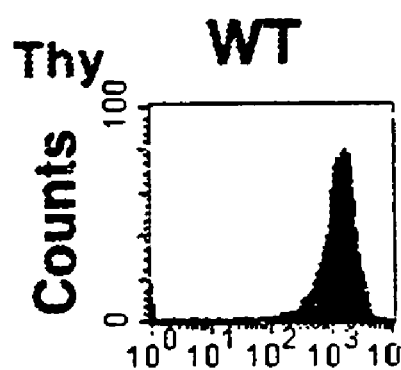 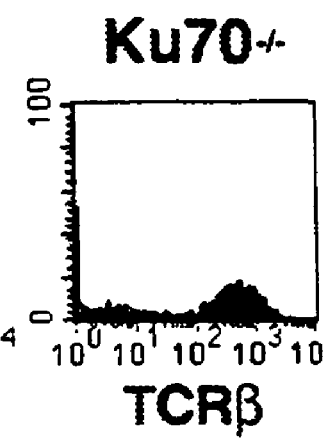 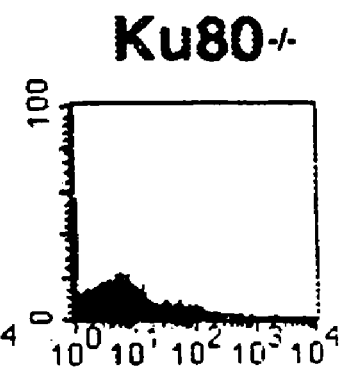
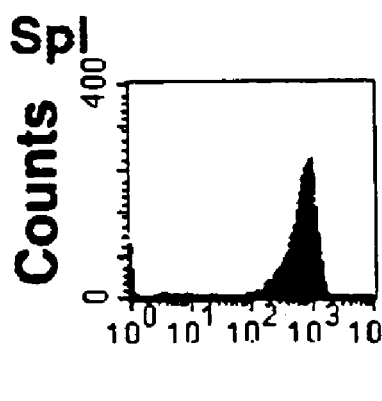 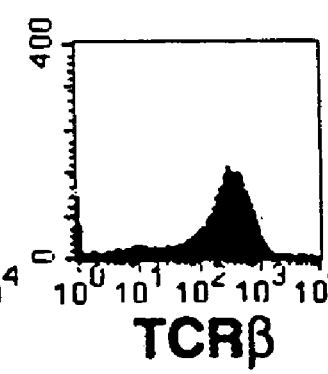 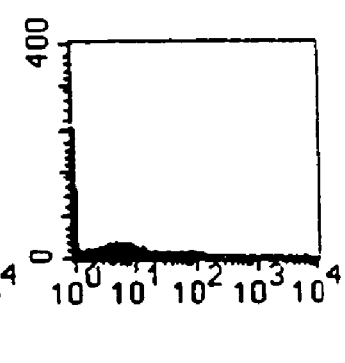
FIG. 2C-4  FIG. 2C-5  FIG. 2C-6

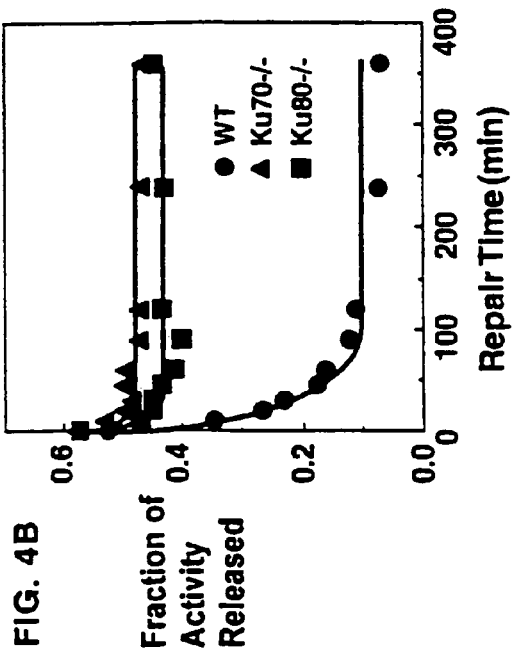
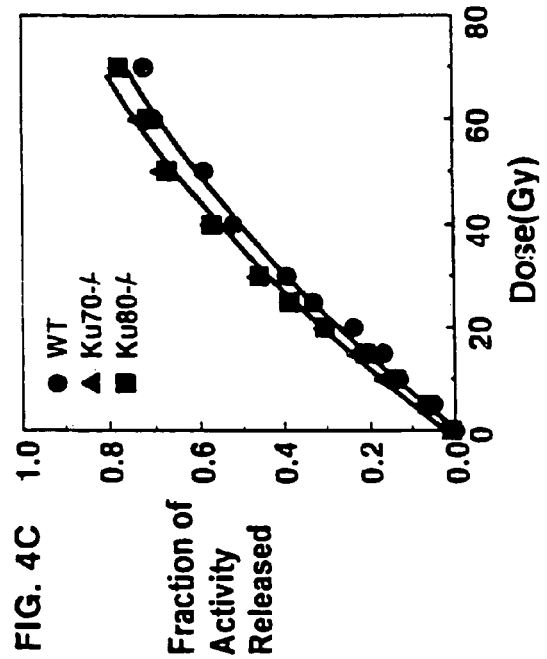
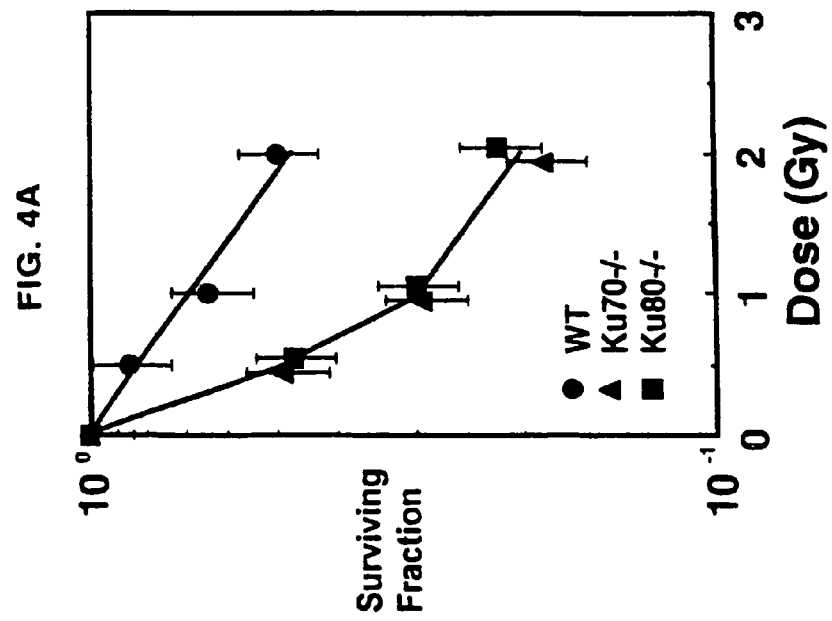
FIG. 4B
FIG. 4C
FIG. 4A

FIG. 5D
 
Ku70 +/+         Ku70 -/- wt (+/+)   70 (+/-)   70 (-/-)

wt (+/+)   70 (-/-)   focus T1   focus C2

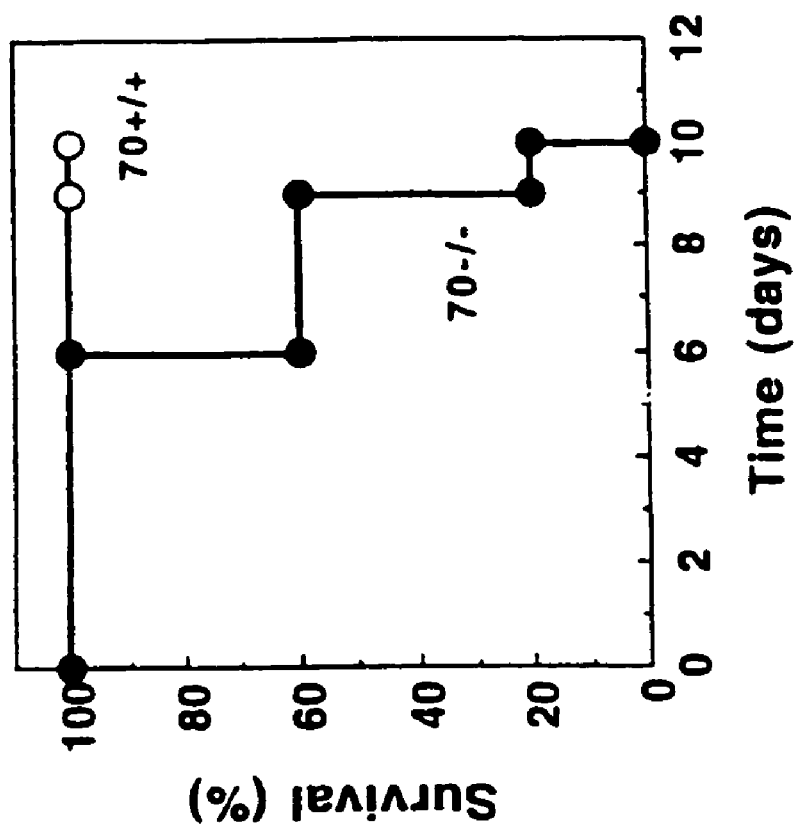
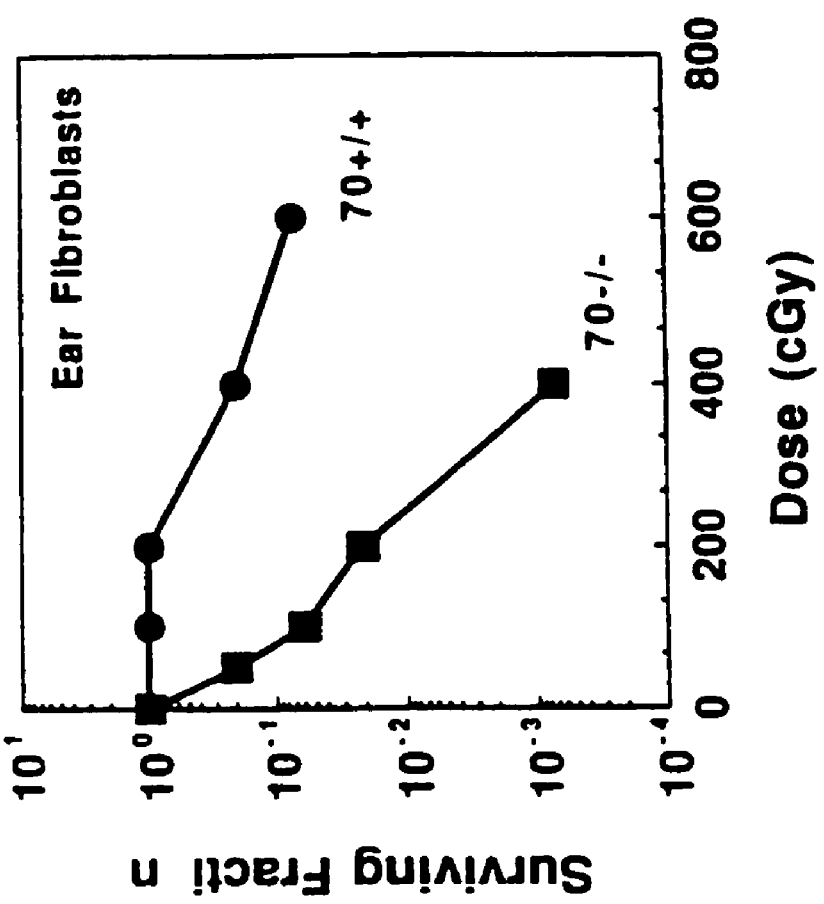
FIG. 9B
FIG. 9A

C T G A

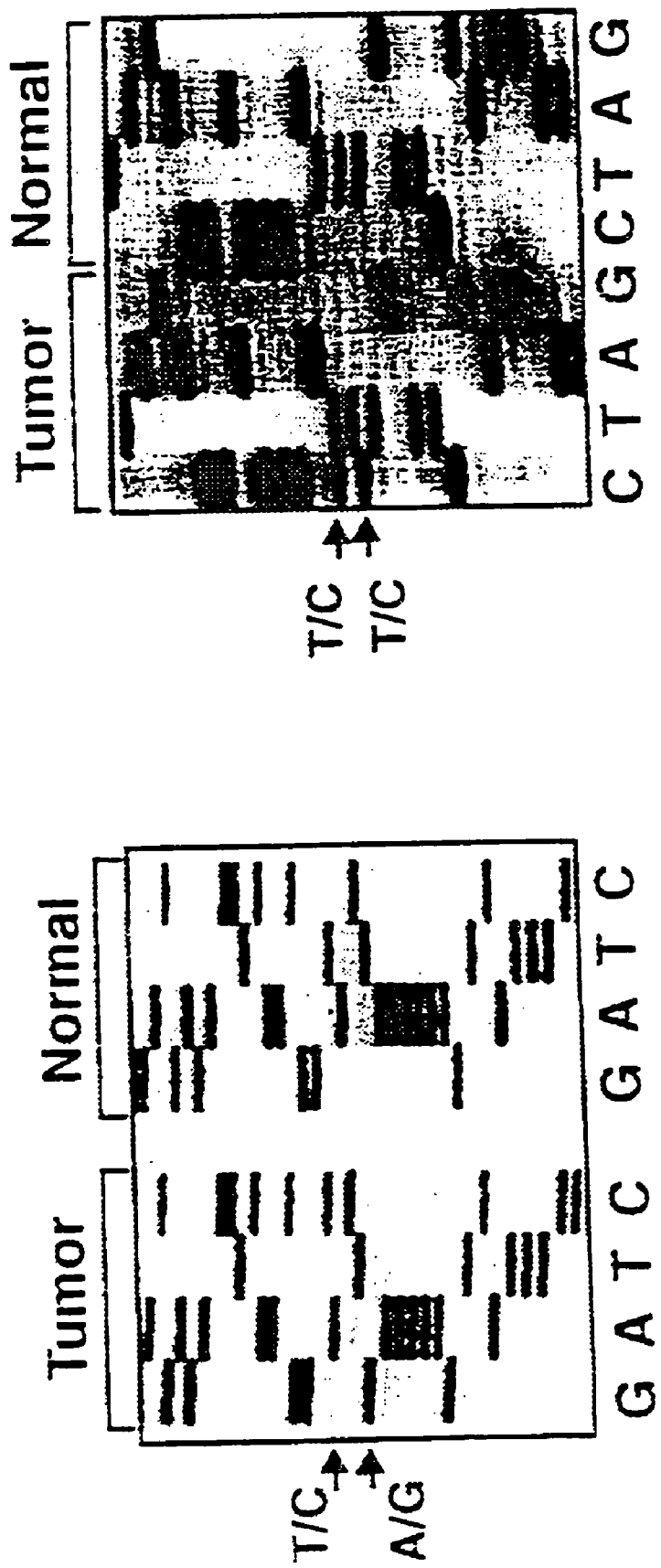

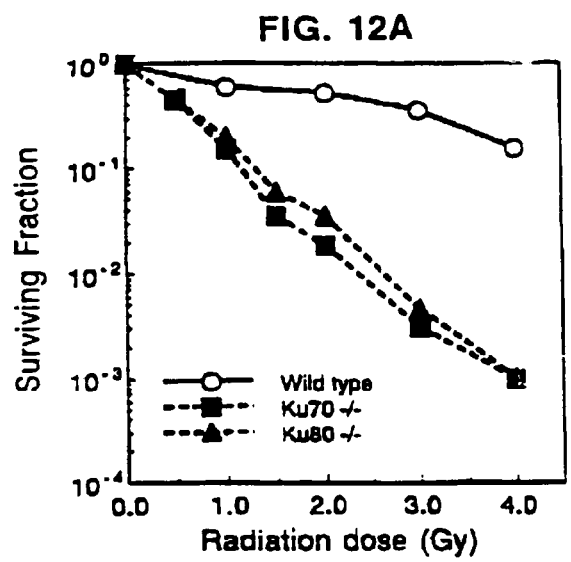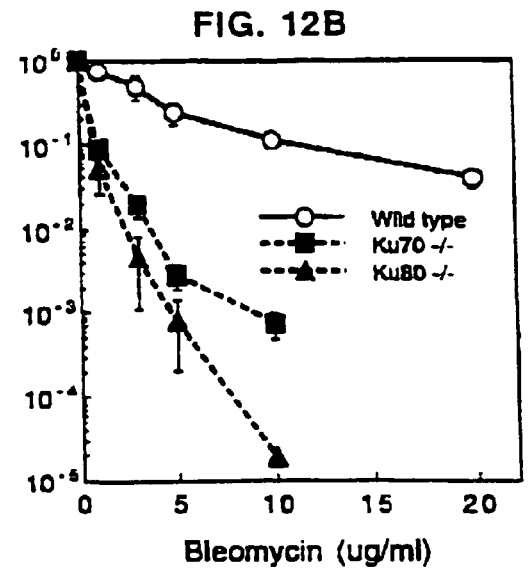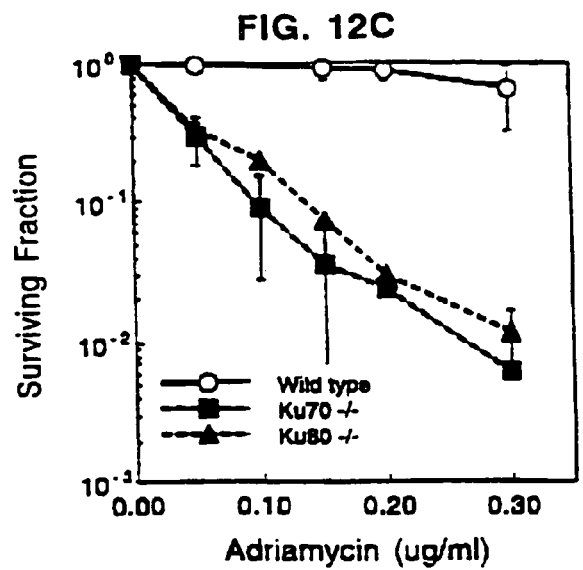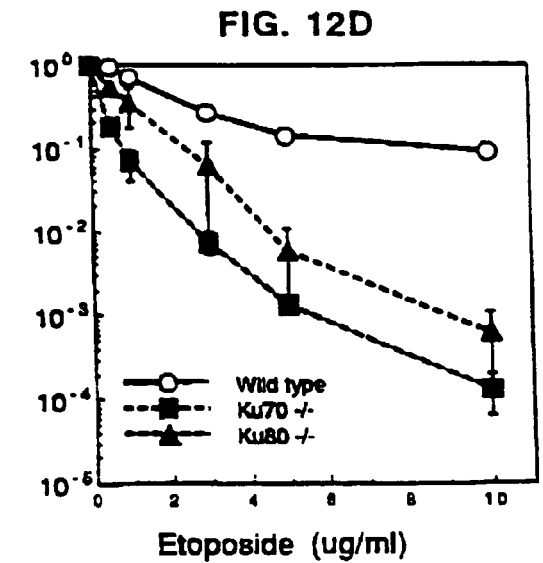

FIG. 14

| Vβ | P | N | Dβ2.1 | N | P | Jβ2.6 |
|---|---|---|---|---|---|---|
| Vβ8.1 <br> AGCTGTATATTCTGTGCCAGCAGTGATG | | | GGGACTGGGGGGC | | | CTCCTATGAACAGTACTTCGGTCCCGGCACCA |
| AGCTGTATATTCTGTGCCAGCAGTG | | | | AGT | | TGAACAGTACTTCGGTCCCGGCACCA(2) |
| AGCTGTATATTCTGTGCCAGC | | CGACA | GGAC | | | CTCCTATGAACAGTACTTCGGTCCCGGCACCA |
| AGCTGTATATTCTGTGCCAGC | | CTG | GG | | | CTATGAACAGTACTTCGGTCCCGGCACCA |
| AGCTGTATATTCTGTGCCAGCAGTGA | | | GGGA | | | GAACAGTACTTCGGTCCCGGCACCA |
| Vβ8.2 <br> ATCAGTGTACTTCTGTGCCAGCGGTGATC | | | | | | |
| ATCAGTGTACTTCTGTGCCAGCGGTG | | | C | | | |
| ATCAGTGTACTTCTGTGCCAGCGG | | | GGGGGGC | TT | | TGAACAGTACTTCGGTCCCGGCACCA |
| ATCAGTGTACTTCTGTGCCAGCGGTA | | GCC | | | | GAACAGTACTTCGGTCCCGGCACCA |
| ATCAGTGTACTTCTGTGTGCCAGC | | | GG | | | GTACTTCGGTCACGGCTCCA |
| ATCAGTGTACTTCTGTGTGCCAGC | | | GG | T | | CTCCTATGAACAGTACTTCGGTCCCGGCACCA |
| ATCAGTGTACTTCTGTGCCAGC | | | GG | | | TGAACAGTACTTCGGTCCCGGCACCA |
| ATCAGTGTACTTCTGTGCCAGCGGTGA | | CA | GGGA | | AG | CTCCTATGAACAGTACTTCGGTCCCGGCACCA |
| Vβ8.3 <br> ATCTTTGTACTTCTGTGCCAGCAGTGATG | | | | | | |
| ATCTTTGTACTTCTGTGCCAGCAGTGATG | CA | | | | | CCTATGAACAGTACTTCGGTCCCGGCACCA |
| ATCTTTGTACTTCTGTGCCAGC | | | GGGG | | | TACTTCGGTCCCGGCACCA |
| ATCTTTGTACTTCTGTGCCAGCAGCAGTGAT | | | TG | | | CCTATGAACAGTACTTCGGTCCCGGCACCA |
| ATCTTTGTACTTCTGTGCCAGCAGCAGTGAT | | | | C | | CCTATGAACAGTACTTCGGTCCCGGCACCA |
| ATCTTTGTACTTCTGTGCCAGCAGTGAT | | | TGGG | | | CCTATGAACAGTACTTCGGTCCCGGCACCA |
| ATCTTTGTACTTCTGTGCCAGCAGTGA | | | | | | CCTATGAACAGTACTTCGGTCCCGGCACCA |

FIG. 16A-1
Wild Type
FIG. 16A-2
PKcs-/-
Thy
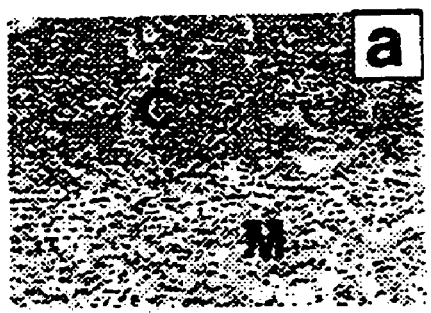 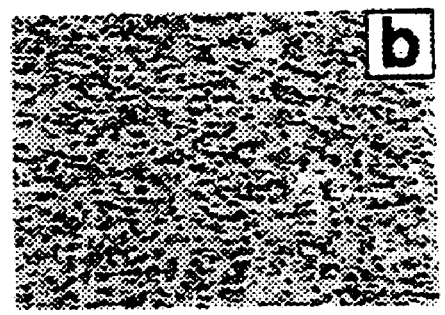
Spl
 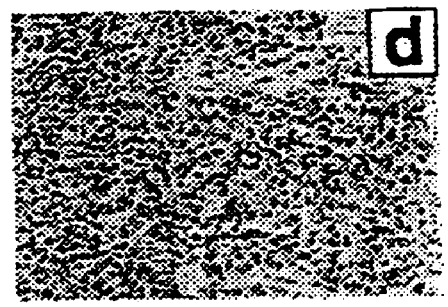
FIG. 16A-3
FIG. 16A-4
LN
 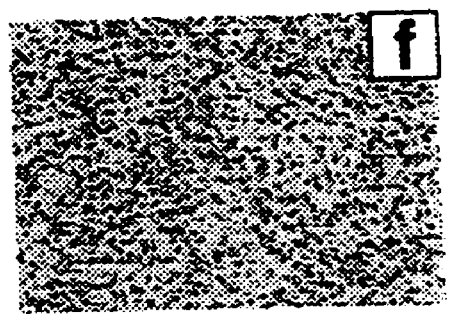
FIG. 16A-5
FIG. 16A-6

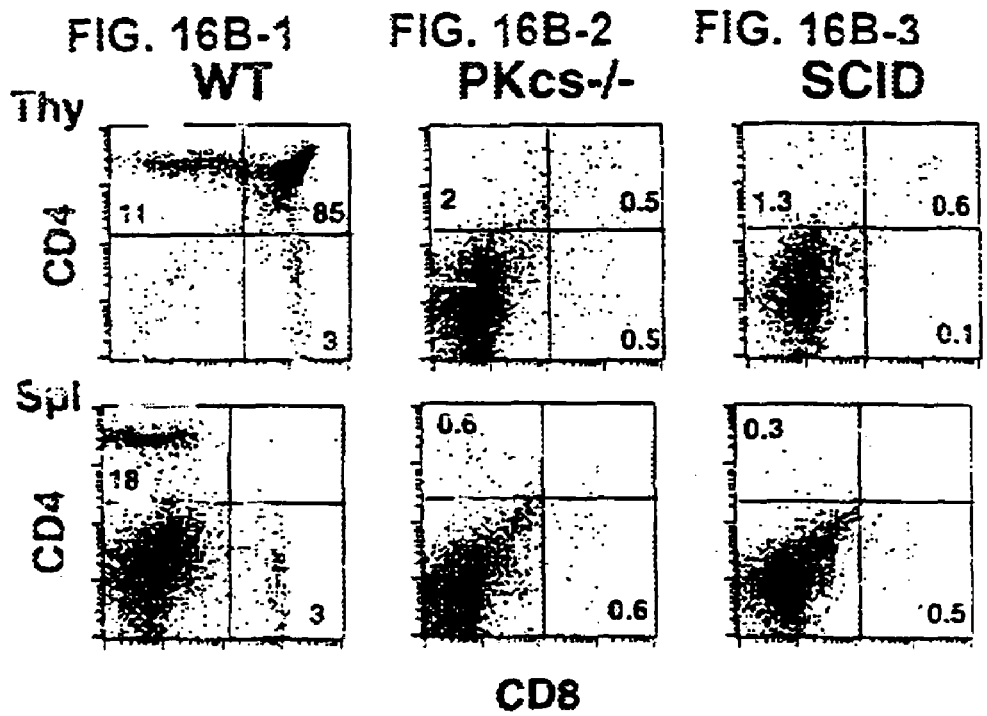
FIG. 16B-1 WT  FIG. 16B-2 PKcs-/-  FIG. 16B-3 SCID
FIG. 16B-4  FIG. 16B-5  FIG. 16B-6
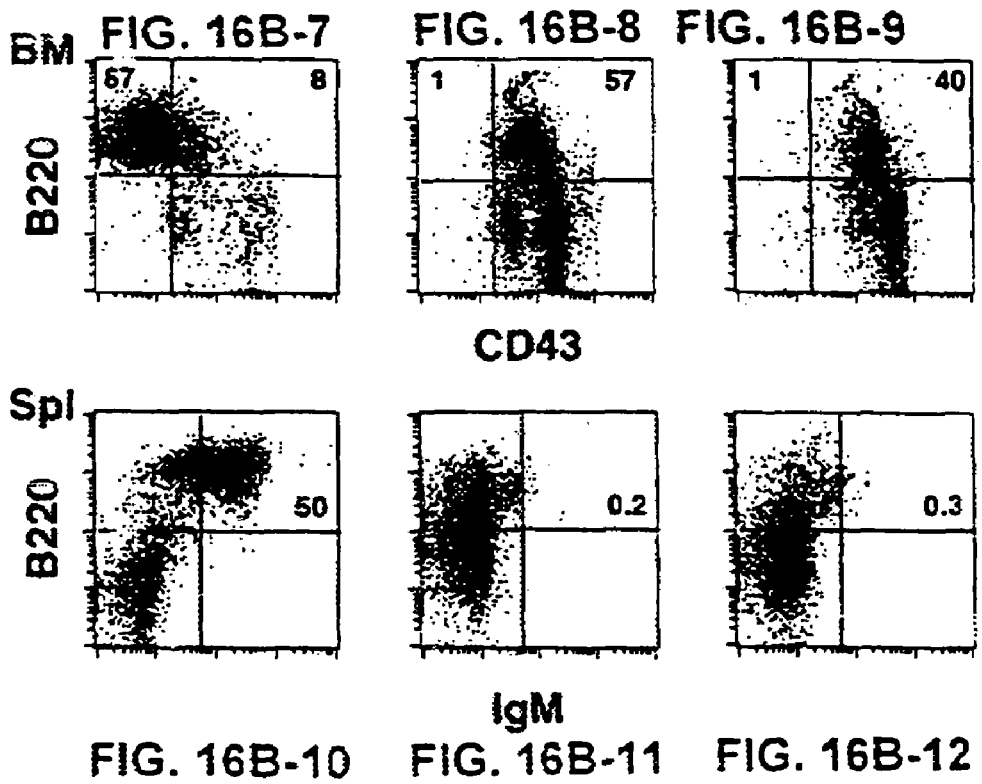
FIG. 16B-7  FIG. 16B-8  FIG. 16B-9
FIG. 16B-10  FIG. 16B-11  FIG. 16B-12

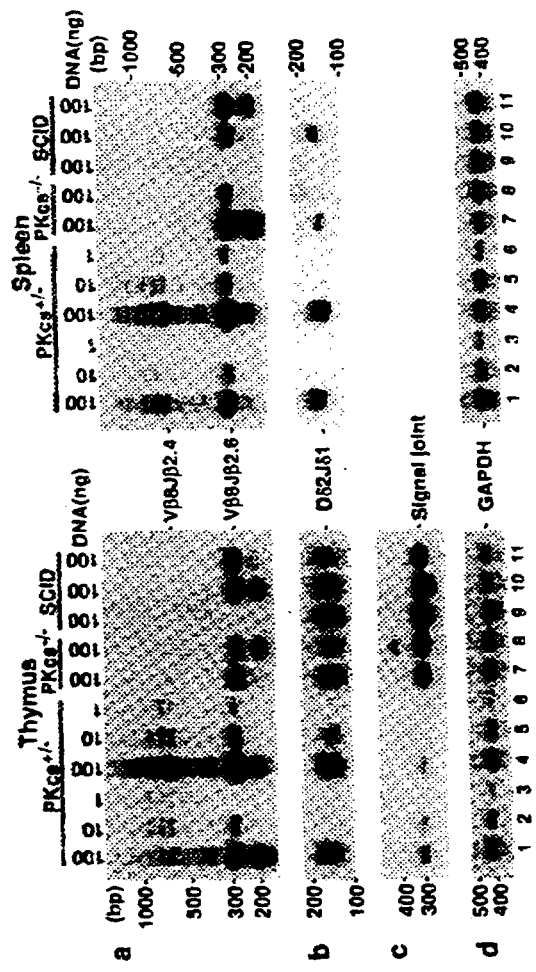
FIG. 16C-1
FIG. 16C-2
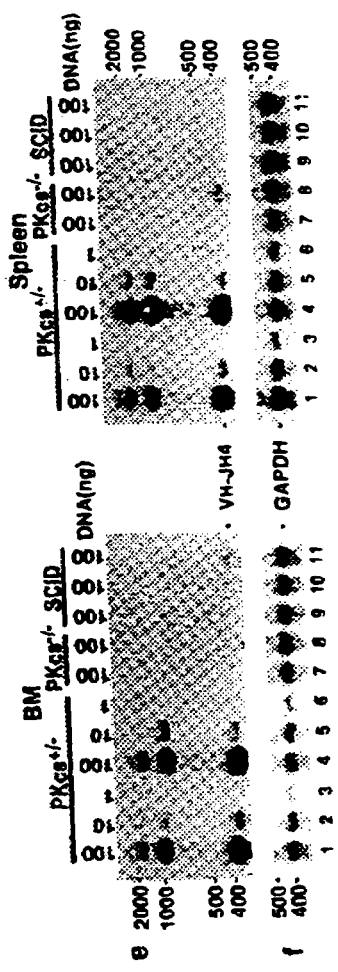
FIG. 16C-3
FIG. 16C-4

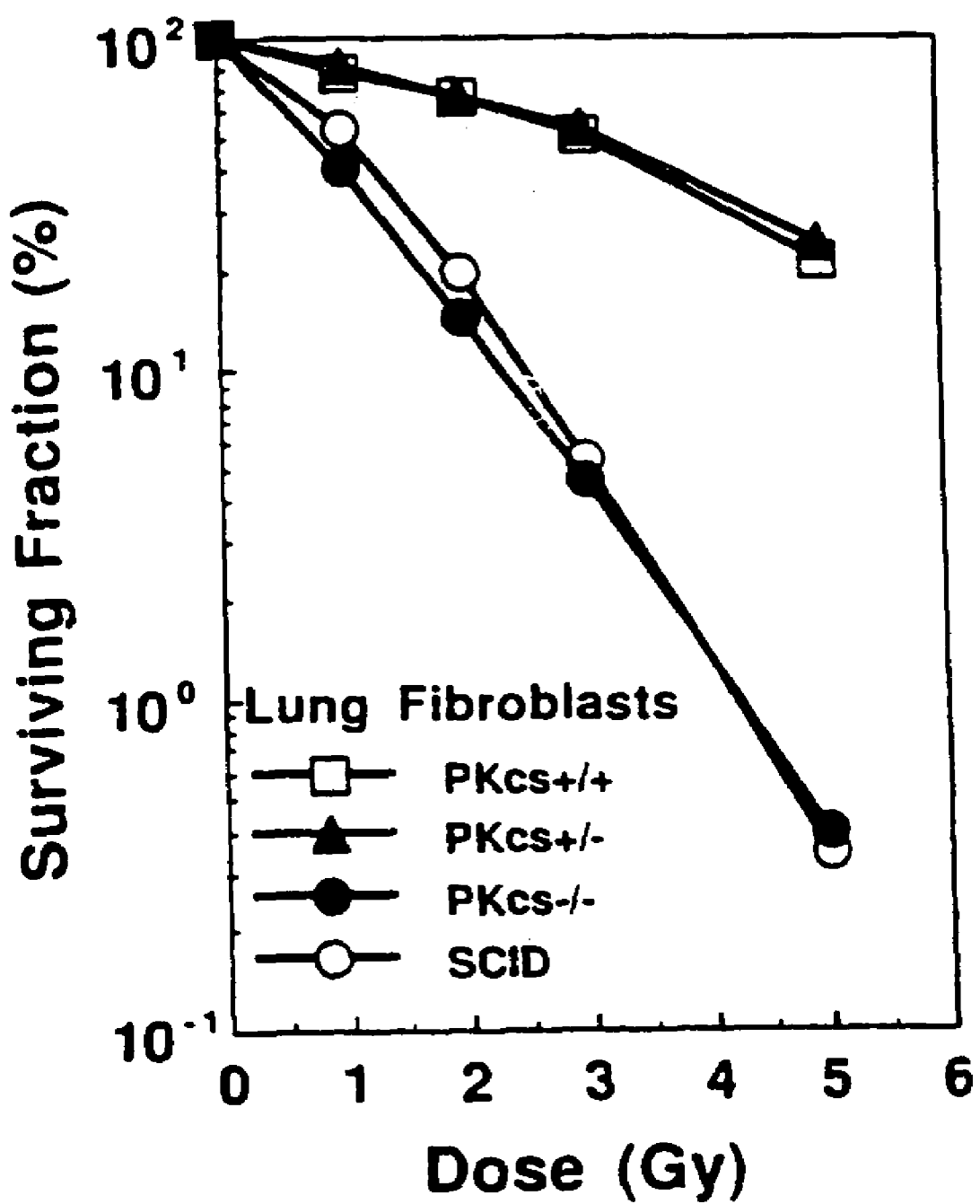

FIG. 18A
FIG. 18C
FIG. 18B
FIG. 18D
FIG. 18E

```
SEQUENCE LISTING

<160> NUMBER OF SEQ ID NOS: 59

<210> SEQ ID NO 1
<211> LENGTH: 29
<212> TYPE: DNA
<213> ORGANISM: Mouse

<400> SEQUENCE: 1
agctgtatat ttctgtgcca gcagtgatg                              29

<210> SEQ ID NO 2
<211> LENGTH: 26
<212> TYPE: DNA
<213> ORGANISM: Mouse

<400> SEQUENCE: 2
agctgtatat ttctgtgcca gcagtg                                 26
```

<210> SEQ ID NO 3
<211> LENGTH: 22
<212> TYPE: DNA
<213> ORGANISM: Mouse

<400> SEQUENCE: 3
agctgtatat tctgtgcca gc                                    22

<210> SEQ ID NO 4
<211> LENGTH: 27
<212> TYPE: DNA
<213> ORGANISM: Mouse

<400> SEQUENCE: 4
agctgtatat tctgtgcca gcagtga                               27

<210> SEQ ID NO 5
<211> LENGTH: 29
<212> TYPE: DNA
<213> ORGANISM: Mouse

<400> SEQUENCE: 5
atcagtgtac ttctgtgcca gcggtgatg                            29

<210> SEQ ID NO 6
<211> LENGTH: 26
<212> TYPE: DNA
<213> ORGANISM: Mouse

<400> SEQUENCE: 6
atcagtgtac ttctgtgcca gcggtg                               26

<210> SEQ ID NO 7
<211> LENGTH: 24
<212> TYPE: DNA
<213> ORGANISM: Mouse

<400> SEQUENCE: 7
atcagtgtac ttctgtgcca gcgg                                 24

<210> SEQ ID NO 8
<211> LENGTH: 26
<212> TYPE: DNA
<213> ORGANISM: Mouse

<400> SEQUENCE: 8
atcagtgtac ttctgtgcca gcggta                               26

<210> SEQ ID NO 9
<211> LENGTH: 22
<212> TYPE: DNA
<213> ORGANISM: Mouse

<400> SEQUENCE: 9
atcagtgtac ttctgtgcca gc                                   22

<210> SEQ ID NO 10
<211> LENGTH: 22
<212> TYPE: DNA
<213> ORGANISM: Mouse

<400> SEQUENCE: 10

| | |
|---|---|
| atcagtgtat ttctgtgcca gc | 22 |

<210> SEQ ID NO 11
<211> LENGTH: 27
<212> TYPE: DNA
<213> ORGANISM: Mouse

<400> SEQUENCE: 11

| | |
|---|---|
| atcagtgtac ttctgtgcca gcggtga | 27 |

<210> SEQ ID NO 12
<211> LENGTH: 29
<212> TYPE: DNA
<213> ORGANISM: Mouse

<400> SEQUENCE: 12

| | |
|---|---|
| atctttgtac ttctgtgcca gcagtgatg | 29 |

<210> SEQ ID NO 13
<211> LENGTH: 22
<212> TYPE: DNA
<213> ORGANISM: Mouse

<400> SEQUENCE: 13

| | |
|---|---|
| atctttgtac ttctgtgcca gc | 22 |

<210> SEQ ID NO 14
<211> LENGTH: 28
<212> TYPE: DNA
<213> ORGANISM: Mouse

<400> SEQUENCE: 14

| | |
|---|---|
| atctttgtac ttctgtgcca gcagtgat | 28 |

<210> SEQ ID NO 15
<211> LENGTH: 27
<212> TYPE: DNA
<213> ORGANISM: Mouse

<400> SEQUENCE: 15

| | |
|---|---|
| atctttgtac ttctgtgcca gcagtga | 27 |

<210> SEQ ID NO 16
<211> LENGTH: 14
<212> TYPE: DNA
<213> ORGANISM: Mouse

<400> SEQUENCE: 16

| | |
|---|---|
| gggactgggg gggc | 14 |

<210> SEQ ID NO 17
<211> LENGTH: 32
<212> TYPE: DNA
<213> ORGANISM: Mouse

<400> SEQUENCE: 17

| | |
|---|---|
| ctcctatgaa cagtacttcg gtcccggcac ca | 32 |

<210> SEQ ID NO 18
<211> LENGTH: 26
<212> TYPE: DNA
<213> ORGANISM: Mouse

<400> SEQUENCE: 18

```
tgaacagtac ttcggtcccg gcacca                                          26

<210> SEQ ID NO 19
<211> LENGTH: 29
<212> TYPE: DNA
<213> ORGANISM: Mouse

<400> SEQUENCE: 19
ctatgaacag tacttcggtc ccggcacca                                       29

<210> SEQ ID NO 20
<211> LENGTH: 25
<212> TYPE: DNA
<213> ORGANISM: Mouse

<400> SEQUENCE: 20
gaacagtact tcggtcccgg cacca                                           25

<210> SEQ ID NO 21
<211> LENGTH: 20
<212> TYPE: DNA
<213> ORGANISM: Mouse

<400> SEQUENCE: 21
gtacttcggt cacggctcca                                                 20

<210> SEQ ID NO 22
<211> LENGTH: 30
<212> TYPE: DNA
<213> ORGANISM: Mouse

<400> SEQUENCE: 22
cctatgaaca gtacttcggt cccggcacca                                      30

<210> SEQ ID NO 23
<211> LENGTH: 19
<212> TYPE: DNA
<213> ORGANISM: Mouse

<400> SEQUENCE: 23
tacttcggtc ccggcacca                                                  19

<210> SEQ ID NO 24
<211> LENGTH: 25
<212> TYPE: DNA
<213> ORGANISM: Unknown
<220> FEATURE:
<223> OTHER INFORMATION: Oligonucleotide Primer

<400> SEQUENCE: 24
gggccagctc attcctccac tcatg                                           25

<210> SEQ ID NO 25
<211> LENGTH: 25
<212> TYPE: DNA
<213> ORGANISM: Unknown
<220> FEATURE:
<223> OTHER INFORMATION: Oligonucleotide Primer

<400> SEQUENCE: 25
cctacagtgt acccggacct atgcc                                           25

<210> SEQ ID NO 26
```

```
<211> LENGTH: 24
<212> TYPE: DNA
<213> ORGANISM: Unknown
<220> FEATURE:
<223> OTHER INFORMATION: Oligonucleotide Primer

<400> SEQUENCE: 26
cggaacagga ctggtggttg agcc                                            24

<210> SEQ ID NO 27
<211> LENGTH: 28
<212> TYPE: DNA
<213> ORGANISM: Unknown
<220> FEATURE:
<223> OTHER INFORMATION: Oligonucleotide

<400> SEQUENCE: 27
gggccaagaa tcttccagca gtttcggg                                        28

<210> SEQ ID NO 28
<211> LENGTH: 20
<212> TYPE: DNA
<213> ORGANISM: Unknown
<220> FEATURE:
<223> OTHER INFORMATION: Oligonucleotide

<400> SEQUENCE: 28
gaggaaaggt gacattgagc                                                 20

<210> SEQ ID NO 29
<211> LENGTH: 22
<212> TYPE: DNA
<213> ORGANISM: Unknown
<220> FEATURE:
<223> OTHER INFORMATION: Oligonucleotide

<400> SEQUENCE: 29
gcctggtgcc gggaccgaag ta                                              22

<210> SEQ ID NO 30
<211> LENGTH: 20
<212> TYPE: DNA
<213> ORGANISM: Unknown
<220> FEATURE:
<223> OTHER INFORMATION: Oligonucleotide Probe

<400> SEQUENCE: 30
gggctgaggc tgatccatta                                                 20

<210> SEQ ID NO 31
<211> LENGTH: 25
<212> TYPE: DNA
<213> ORGANISM: Unknown
<220> FEATURE:
<223> OTHER INFORMATION: Oligonucleotide

<400> SEQUENCE: 31
tggcttgaca tgcagaaaac acctg                                           25

<210> SEQ ID NO 32
<211> LENGTH: 24
<212> TYPE: DNA
<213> ORGANISM: Unknown
<220> FEATURE:
<223> OTHER INFORMATION: Oligonucleotide

<400> SEQUENCE: 32
```
tgaattccac agtcacttgg cttc                     24

<210> SEQ ID NO 33
<211> LENGTH: 25
<212> TYPE: DNA
<213> ORGANISM: Unknown
<220> FEATURE:
<223> OTHER INFORMATION: Oligonucleotide Probe

<400> SEQUENCE: 33
gacacgtgat acaaagccca gggaa                    25

<210> SEQ ID NO 34
<211> LENGTH: 21
<212> TYPE: DNA
<213> ORGANISM: Unknown
<220> FEATURE:
<223> OTHER INFORMATION: Oligonucleotide

<400> SEQUENCE: 34
gtcaagggat ctactactgt g                        21

<210> SEQ ID NO 35
<211> LENGTH: 34
<212> TYPE: DNA
<213> ORGANISM: Unknown
<220> FEATURE:
<223> OTHER INFORMATION: Oligonucleotide

<400> SEQUENCE: 35
gagagaattc agagacaatc ccaagaacac cctg          34

<210> SEQ ID NO 36
<211> LENGTH: 31
<212> TYPE: DNA
<213> ORGANISM: Unknown
<220> FEATURE:
<223> OTHER INFORMATION: Oligonucleotide

<400> SEQUENCE: 36
gagagaattc tcctccagca cagcctacat g              31

<210> SEQ ID NO 37
<211> LENGTH: 31
<212> TYPE: DNA
<213> ORGANISM: Unknown
<220> FEATURE:
<223> OTHER INFORMATION: Oligonucleotide

<400> SEQUENCE: 37
gagagaattc ggctcccaat gacccttct g               31

<210> SEQ ID NO 38
<211> LENGTH: 21
<212> TYPE: DNA
<213> ORGANISM: Unknown
<220> FEATURE:
<223> OTHER INFORMATION: Oligonucleotide

<400> SEQUENCE: 38
gtaagaatgg cctctccagg t                        21

<210> SEQ ID NO 39
<211> LENGTH: 21
<212> TYPE: DNA

```
<213> ORGANISM: Unknown
<220> FEATURE:
<223> OTHER INFORMATION: Oligonucleotide

<400> SEQUENCE: 39
gactcaatca ctaagacagc t                                              21

<210> SEQ ID NO 40
<211> LENGTH: 25
<212> TYPE: DNA
<213> ORGANISM: Unknown
<220> FEATURE:
<223> OTHER INFORMATION: Oligonucleotide Primer

<400> SEQUENCE: 40
gggccagctc attcctccac tcatg                                          25

<210> SEQ ID NO 41
<211> LENGTH: 24
<212> TYPE: DNA
<213> ORGANISM: Unknown
<220> FEATURE:
<223> OTHER INFORMATION: Oligonucleotide  Primer

<400> SEQUENCE: 41
cggaacagga ctggtggttg agcc                                           24

<210> SEQ ID NO 42
<211> LENGTH: 23
<212> TYPE: DNA
<213> ORGANISM: Unknown
<220> FEATURE:
<223> OTHER INFORMATION: Oligonucleotide Primer

<400> SEQUENCE: 42
tatccggaag tcgcttagca ttg                                            23

<210> SEQ ID NO 43
<211> LENGTH: 23
<212> TYPE: DNA
<213> ORGANISM: Unknown
<220> FEATURE:
<223> OTHER INFORMATION: Oligonucleotide Primer

<400> SEQUENCE: 43
aagacggttg aagtcagaag tcc                                            23

<210> SEQ ID NO 44
<211> LENGTH: 24
<212> TYPE: DNA
<213> ORGANISM: Unknown
<220> FEATURE:
<223> OTHER INFORMATION: Oligonucleotide Primer

<400> SEQUENCE: 44
ttcacataca ccttgtctcc gacg                                           24

<210> SEQ ID NO 45
<211> LENGTH: 23
<212> TYPE: DNA
<213> ORGANISM: Unknown
<220> FEATURE:
<223> OTHER INFORMATION: Oligonucleotide Primer

<400> SEQUENCE: 45
atcagaaggt ctaaggctgg aat                                            23
```

<210> SEQ ID NO 46
<211> LENGTH: 20
<212> TYPE: DNA
<213> ORGANISM: Unknown
<220> FEATURE:
<223> OTHER INFORMATION: Oligonucleotide Primer

<400> SEQUENCE: 46
cgtacggtgt tggctactgc                                          20

<210> SEQ ID NO 47
<211> LENGTH: 23
<212> TYPE: DNA
<213> ORGANISM: Unknown
<220> FEATURE:
<223> OTHER INFORMATION: Oligonucleotide Primer

<400> SEQUENCE: 47
cactgagggc tttccgctct tgt                                      23

<210> SEQ ID NO 48
<211> LENGTH: 23
<212> TYPE: DNA
<213> ORGANISM: Unknown
<220> FEATURE:
<223> OTHER INFORMATION: Oligonucleotide Primer

<400> SEQUENCE: 48
gctcttgtgc acgaatgttg tag                                      23

<210> SEQ ID NO 49
<211> LENGTH: 20
<212> TYPE: DNA
<213> ORGANISM: Unknown
<220> FEATURE:
<223> OTHER INFORMATION: Oligonucleotide Primer

<400> SEQUENCE: 49
agaagactgt ggatggcccc                                          20

<210> SEQ ID NO 50
<211> LENGTH: 19
<212> TYPE: DNA
<213> ORGANISM: Unknown
<220> FEATURE:
<223> OTHER INFORMATION: Oligonucleotide Primer

<400> SEQUENCE: 50
aggtccacca ccctgttgc                                           19

<210> SEQ ID NO 51
<211> LENGTH: 20
<212> TYPE: DNA
<213> ORGANISM: Unknown
<220> FEATURE:
<223> OTHER INFORMATION: Oligonucleotide

<400> SEQUENCE: 51
gaggaaaggt gacattgagc                                          20

<210> SEQ ID NO 52
<211> LENGTH: 20
<212> TYPE: DNA
<213> ORGANISM: Unknown
<220> FEATURE:

<223> OTHER INFORMATION: Oligonucleotide Probe

<400> SEQUENCE: 52
gggctgaggc tgatccatta                                                    20

<210> SEQ ID NO 53
<211> LENGTH: 24
<212> TYPE: DNA
<213> ORGANISM: Unknown
<220> FEATURE:
<223> OTHER INFORMATION: Oligonucleotide

<400> SEQUENCE: 53
tgaattccac agtcacttgg gttc                                               24

<210> SEQ ID NO 54
<211> LENGTH: 25
<212> TYPE: DNA
<213> ORGANISM: Unknown
<220> FEATURE:
<223> OTHER INFORMATION: Oligonucleotide

<400> SEQUENCE: 54
gtcatatctt gtccagtcaa cttcc                                              25

<210> SEQ ID NO 55
<211> LENGTH: 25
<212> TYPE: DNA
<213> ORGANISM: Unknown
<220> FEATURE:
<223> OTHER INFORMATION: Oligonucleotide Primer

<400> SEQUENCE: 55
gatgagccag ctggatgagt aacac                                              25

<210> SEQ ID NO 56
<211> LENGTH: 24
<212> TYPE: DNA
<213> ORGANISM: Unknown
<220> FEATURE:
<223> OTHER INFORMATION: Oligonucleotide Probe

<400> SEQUENCE: 56
gccctctagc catgacatca gagc                                               24

<210> SEQ ID NO 57
<211> LENGTH: 26
<212> TYPE: DNA
<213> ORGANISM: Unknown
<220> FEATURE:
<223> OTHER INFORMATION: Oligonucleotide

<400> SEQUENCE: 57
cgcgaagctt cgtggagtct ggggga                                             26

<210> SEQ ID NO 58
<211> LENGTH: 26
<212> TYPE: DNA
<213> ORGANISM: Unknown
<220> FEATURE:
<223> OTHER INFORMATION: Oligonucleotide

<400> SEQUENCE: 58
ggggaattcc tgaggagacg gtgact                                             26

```
<210> SEQ ID NO 59
<211> LENGTH: 26
<212> TYPE: DNA
<213> ORGANISM: Unknown
<220> FEATURE:
<223> OTHER INFORMATION: Oligonucleotide Probe

<400> SEQUENCE: 59
accccagtag tccatagcat agtaat                                          26
```

USES OF DNA-PK

This application is a continuation of U.S. Ser. No. 09/750,410, filed Dec. 28, 2000, a continuation of PCT International Application No. PCT/US99/14702, filed Jun. 30, 1999, on behalf of Sloan Kettering Institute for Cancer Research, claiming priority of U.S. Provisional Application No. 60/091,181, filed Jun. 30, 1998, the contents of which are hereby incorporated into this application by reference.

Within this application publications are referenced within parentheses. Full citations for these references may be found at the end of each series of experiments. The disclosures of these publications in their entireties are hereby incorporated by reference into this application in order to more fully describe the state of the art to which this invention pertains.

The invention disclosed herein was made with Government support under NIH Grant Nos. CA-31397, CA-56909 and CA-78497 from the Department of Health and Human Services. Accordingly, the U.S. Government has certain rights in this invention.

BACKGROUND OF THE INVENTION

Two distinct processes involving DNA double-strand breaks (DSB) have been identified in mammalian cells: the repair of DNA damage induced by ionizing radiation and V(D)J recombination during T- and B-cell development. So far, all mammalian cell mutants defective in DNA DSB repair share the common phenotype of hypersensitivity to radiation, and impaired ability to undergo V(D)J recombination (1-6). Cell fusion studies using DSB repair mutants of human-rodent somatic hybrids have defined four complementation groups: IR4, IR5, IR6, and IR7. Genetic and biochemical analyses have revealed that cells of IR5 (e.g., xrs-6) and IR7 (e.g., scid) are defective in components of the DNA-dependent protein kinase (DNA-PK) (2, 7-9). DNA-PK is a serine/threonine kinase comprised of a large catalytic subunit (DNA-PK$_{cs}$) and a DNA-targeting component termed Ku, which itself is a heterodimer of a 70-kDa (Ku70) and a 86-kDa (Ku80) polypeptide (10-12). Recently, DNA-PK$_{cs}$ has been shown to be the gene responsible for the murine scid (severe combined immunodeficiency) defect (13-15); and Ku80 has been identified to be XRCC5 (16-18), the X-ray-repair cross-complementing gene for IR5. Ku80 knockout mice were found to exhibit severe combined immunodeficiency, defective processing of V(D)J recombination intermediates, and growth retardation (19, 20).

Though Ku70 has been designated as XRCC6 (7, 8) and is an important component of the DNA-PK complex, the function of Ku70 in vivo is hitherto unknown. To define the role of Ku70 in DNA repair and V(D)J recombination, we targeted the Ku70 gene in mice. Ku70 homozygotes exhibit proportional dwarfism, a phenotype of Ku80−/−, but not of scid mice. Absence of Ku70 confers hypersensitivity to ionizing radiation and deficiency in DNA DSB repair, which are characteristics of both Ku80−/− and scid mice.

Surprisingly, in contrast to Ku80−/− and scid mice, in which both T- and B-lymphocyte development are arrested at early stage, lack of Ku70 is compatible with T cell receptor gene recombination and the development of mature CD4$^+$ CD8$^−$ and CD4$^−$CD8$^+$ T cells. Our data, for the first time, provide direct evidence supporting that Ku70 plays an essential role in DNA DSB repair, but is not required for TCR gene recombination. These results suggest that distinct but overlapping repair pathways may mediate DSB repair and V(D)J rejoining; furthermore, it suggests the presence of a Ku70-independent rescue pathway in TCR V(D)J recombination. The distinct phenotype of Ku70−/− mice should make them valuable tools for unraveling the mechanism(s) of DNA repair and recombination.

Ku is a complex of two proteins, Ku70 and Ku80, that functions as a heterodimer to bind DNA double-strand breaks (DSB) and activate DNA-dependent protein kinase (DNA-PK). The role of the Ku70 subunit in DNA DSB repair, hypersensitivity to ionizing radiation and V(D)J recombination was examined in mice that lack Ku70(Ku70−/−). Like Ku80−/− mice, Ku70$^{−/−}$ mice showed a profound deficiency in DNA DSB repair and were proportional dwarfs. Surprisingly, in contrast to Ku80 $^{−/−}$ mice, in which both T- and B-lymphocyte development were arrested at early stage, lack of Ku70 was compatible with T cell receptor gene recombination and the development of mature CD4$^+$CD8$^−$ and CD4$^−$CD8$^+$ T cells. Our data shows, for the first time, that Ku70 plays an essential role in DNA DSB repair, but is not required for TCR V(D)J recombination. These results suggest that distinct but overlapping repair pathways may mediate DNA DSB repair and V(D)J recombination.

SUMMARY OF THE INVENTION

This invention provides a method for increasing the susceptibility of a cell to DNA-damaging agents, comprising introducing into the cell an antisense oligonucleotide that specifically hybridizes to a nucleic acid encoding a DNA dependent protein kinase subunit so as to prevent expression of the DNA dependent protein kinase subunit; wherein the antisense oligonucleotide is in an amount sufficient to increase the sensitivity of the cell to heat, chemical, or radiation-induced DNA damage; and wherein the DNA dependent protein kinase subunit is a DNA dependent protein kinase catalytic subunit, a Ku70, or a Ku80.

This invention also provides a method of treating a tumor in a subject, comprising administering to the subject an antisense oligonucleotide that specifically hybridizes to a nucleic acid encoding a DNA dependent protein kinase subunit so as to prevent expression of the DNA dependent protein kinase subunit; wherein the antisense oligonucleotide is in an amount sufficient to increase the sensitivity of the tumor to heat, chemical or radiation-induced DNA damage; and wherein the DNA dependent protein kinase subunit is a DNA dependent protein kinase catalytic subunit, a Ku70, or a Ku80.

In addition, this invention provides a method for treating cancer in a subject, comprising: introducing into the subject an expression vector comprising a heat shock promoter and an antisense oligonucleotide that specifically hybridizes to a nucleic acid encoding a DNA dependent protein kinase subunit so as to prevent expression of the DNA dependent protein kinase subunit; and inducing expression of the antisense oligonucleotide, wherein the antisense oligonucleotide is in an amount sufficient to increase the sensitivity of the cell to heat, chemical, or radiation-induced DNA damage; and wherein the DNA dependent protein kinase subunit is a DNA dependent protein kinase catalytic subunit, a Ku70, or a Ku80.

This invention provides an antisense oligonucleotide that specifically hybridizes to a nucleic acid encoding a DNA dependent protein kinase subunit, wherein the DNA dependent protein kinase subunit is a DNA dependent protein kinase catalytic subunit, Ku70, or Ku80, so as to prevent expression of the DNA dependent protein kinase subunit.

This invention provides a pharmaceutical composition comprising the the above-described antisense oligonucleotides and a carrier.

Figure 1A:
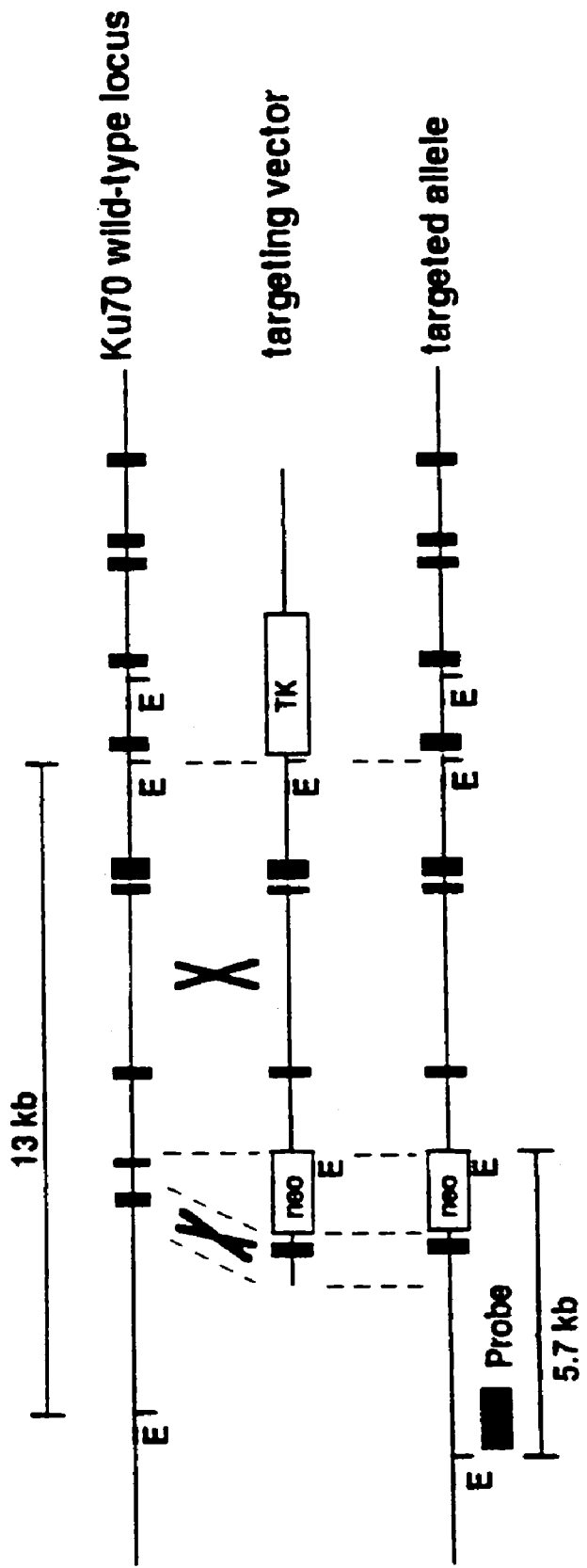
FIG. 1

Inactivation of Ku70 by homologous recombination. (A) Diagrammatic representation of the Ku70 locus (top), the targeting construct (middle), and the targeted allele and hybridization probe (bottom). EcoRI restriction sites used to detect the targeted gene are indicated (21). (B) Southern blot of EcoRI-digested tail DNA from control wild type (WT), heterozygous (+/−) and homozygous (−/−) Ku70-targeted mice. The wild-type and mutant fragments are 13 and 5.7 kb respectively. (C) Western blot analysis showing that Ku70 protein is not expressed in Ku70−/− cells. Whole-cell lysates prepared from mouse ear fibroblasts (50 µg) and mouse embryo fibroblasts (100 µg) were separated by 10% SDS-PAGE, transferred to a nitrocellulose membrane, and probed with polyclonal antibodies against full-length rodent Ku80 (top) and Ku70(bottom), respectively. (D) Gel mobility shift assay (22) showing the lack of DNA-end binding activity in Ku70−/− cells. Ku-DNA binding complex is indicated by arrow on the right.

FIG. 2

Development of B lymphocyte, but not T lymphocyte, is blocked at an early stage in Ku70−/− mice. (A) Histology of thymus (Thy), lymph nodes (LN) and spleens (Spl) from wild type control mice, Ku70−/− mice, and Ku80−/− mice (23). Cortex (C) and medulla (M) are indicated. W, white pulp; R. red pulp; GC, germinal center. Panels a to i, tissue sections were stained with haematoxylin and eosin (HE); panels j to l, tissue sections were stained with anti-CD3 (CD3); and panels m to o, tissues were stained with anti-CD19 (CD19). Anti-CD3 and anti-CD19 antibodies were tested in both frozen and paraffin sections of wild-type lymphoid organs and showed the expected specific patterns of staining. (B) Flow cytometric analysis of thymocytes (Thy) bone marrow (BM) and spleen (Spl) cells from Ku70−/− mice, Ku70+/+ littermates, and Ku80−/− mice. CD4, anti-CD4 monoclonal antibody; CD8, anti-CD8 monoclonal antibody; B220, anti-B220 monoclonal antibody; CD43, anti-CD43 monoclonal antibody; IgM, anti-1 gµ-heavy-chain monoclonal antibody. The data were gated for live lymphoid cells based on forward and side scatter properties; 10,000-20,000 cells were analyzed per sample. (C) Analysis of TCRβ chain expression in Ku70−/− mice. Thymocytes and spleen cells were obtained from Ku70−/−, Ku80−/−, and wild type littermates and analyzed for expression of CD4, CD8 and TCRβ by 3-color flow cytometry. The TCRβ expression of both $CD4^+$ and $CD8^+$ single-positive T cells were shown.

FIG. 3

T-cell antigen receptor and immunoglobulin gene rearrangement in Ku70−/− mice. (A) Recombination of V558L, V7183 to $DJ_H$, and $D_H$ to $J_H$ gene segments (26). 100 ng DNA was used for Ku70−/− (lanes 7 and 8), Ku80−/− (lanes 1, 2, and 3), and SCID mice (lanes 4, 5, and 6), and 1, 10 and 100 ng for WT mice (lanes 9-11). For IVS controls, DNA was diluted 100-fold before PCR. (B) PCR analysis of TCR gene rearrangements. Thymus DNA was assayed for recombination of Vβ8-Jβ2 and Dδ2 to Jδ1 rearrangements (20, 27, 28). 100 ng DNA was used for Ku70−/− (lanes 2 and 7), Ku80−/− (lane 1), and Ku70+/− mice (lane 7) and 1, 10 and 100 ng for WT mice (lanes 4-6). Controls include a 1-kb germline interval amplified in the Dδ2 to Jδ1 intervening region (germline), and a non-recombining segment of the Ig locus between $J_H$ Hand $C_H1$. The same thymus DNA samples were examined for Vβ8-Jβ2 and Dδ2 to Jδ1 recombination. Abbreviations: $DJ_H$, $D_H$ to $J_H$ rearrangements; $V7183J_H$ and $V558LJ_H$, V7183 and V558L to $DJ_H$ rearrangements (26); Vβ8Jβ2.1 to Vβ8-Jβ2.6, Vβ8 to DJβ2 rearrangements (28); germline, unrecombined DNA from the Dδ2 to Jδ1 interval; Dδ2Jδ1, Dδ2 to Jδ1 rearrangements (20, 27); IVS, non-recombining segment of the Ig locus between $J_H$ and $C_H1$ (26). Multiple lanes underneath each genotype label (Ku70−/−, Ku80−/−, and SCID) represent different individual animals.

FIG. 4

Disruption of Ku70 confers radiation hypersensitivity and a deficiency in DNA DSB repair. (A) Radiation survival curves for the granulocyte/macrophage colony-forming units (CFU-GM) in the bone marrow of wild type (WT), Ku70−/−, and Ku80−/− mice (30, 32). (B) Deficiency in the repair of radiation-induced DSB in Ku70−/− and Ku80−/− cells (31). Upper panel shows rejoining of DNA DSB produced by 40 Gy X-ray; (C) Induction of DNA DSB as a function of the radiation dose in WT, Ku70−/− and Ku80−/− cells. Symbols are • for WT, ▲ for Ku70−/−, and ■ for Ku80−/− cells, respectively.

FIG. 5

Disruption of the Ku70 locus in mouse ES cells and generation of Ku70−/− mice. (A) Diagrammatic representation of the Ku70 locus (top), the targeting construct (middle), the targeted allele (bottom) and the PCR primers. EcoRI (E) restriction sites used to detect the targeted genes are indicated. (B) PCR analysis of tail DNA from Ku70+/+, Ku70+/−, and Ku70−/− mice. The wild type sequence which was amplified using HO-4/HO-3 primers was not present in Ku70−/− mouse tail while the disrupted sequence primed by HO-4/HO-2 was not expressed in: Ku70+/+mouse. (C) Postnatal growth of Ku70+/+ and Ku70−/− littermates. Average weights of seven animals from each genotype are plotted against time. There was no significant difference in the body weight between Ku70+/+ and Ku70+/−mice. (D) Photograph of 5-week-old Ku70+/+ and Ku70−/− littermates.

FIG. 6

Survival curves of Ku70+/+, Ku70+/−, and Ku70−/− mice. Sample sizes used for the statistical analysis (Kaplan and Meier, 1958) are: n (+/+)=102, n (+/−)=326, and n (−/−)=185.

FIG. 7

Histological analysis of the spontaneous tumors that developed in Ku70−/− mice. (A & D) Photomicrographs of sections of a thymic lymphoma processed as follows: (A), hematoxylin and eosin staining; (D), positive immunohistochemical surface staining against T-cell surface marker CD3. (B, C, E and F) Photomicrographs of sections of lung tissues showing tumor involvement. (B) and (C), hematoxylin and eosin; (E) and (F), positive immunohistochemical surface staining against T-cell surface marker CD3. B, bronchial lumen; V, blood vessel. (G) Flow cytometric analysis of tumor cells. Cells were labeled with PE-conjugated anti-CD4 and FITC-conjugated anti-CD8 antibodies. Original magnifications: A, C, D and F, 400×; B and E, 100×.

FIG. 8

Neoplastic transformation of Ku70−/− early-passage mouse ear fibroblasts (MEFs). (A) Focus-formation assay. (B) Morphology of transformed foci (type III). (C) Colony-formation assay in soft agar. Left, wild type (Ku70+/+ MEFs untransformed; middle left, Ku70−/− MEFs untransformed; middle right (focus T1), cells from a focus produced by spontaneous transformation of Ku70−/− MEFs (passage 7); and right (focus C2), cells from a focus produced by transformation of E6/E7 co-transfected $Ku70^{-/-}$ MEFs. Cells from other randomly chosen foci were also able to produce colonies in soft agar.

FIG. 9

Radiation sensitivity of Ku70−/− fibroblasts and $Ku70^{-/-}$ 0 mice. (A) Ku70−/− and wild-type Ku70+/+ primary ear fibroblasts (passage 7) were exposed to graded doses of γ-irradiation. Ku70-deficient cells show significantly decreased ability to form colonies after ionizing radiation as compared with the wild-type cells. (B) Survival of Ku70−/− and wild-type mice irradiated with 400 cGy. Five adult mice (4 months old) from each genotype were irradiated simultaneously and monitored for 2 weeks. Whereas all of the wild-type mice survived, 100% of the Ku70−/− mice died within this period.

FIG. 10

Histological appearance of segmental gastrointestinal abnormalities of Ku70−/− mice. Gastrointestinal tissues from a three-month-old Ku70−/− mouse were stained with hematoxylin and eosin and photographed. (A) Normal appearance of the intestine showing the presence of ganglions (400×). (B) Section of intestine from the same animal showing absence of ganglion neurons (400×). (C) At a lower magnification (100×) segmental aganglionosis that developed in a Ku70−/− mouse is demonstrated. The left portion of the specimen shows complete absence of ganglion neurons. This phenotype is associated with the effacement of the typical morphology of the intestinal villi, dilation of intestinal lumen, and denudation of the mucosa, as well as segmental distention of the intestine. In contrast, the right portion of the specimen shows a normal appearance as observed in the wild-type littermates.

FIG. 11

Ku70 alteration in human tumors. Immunohistochemical analysis of Ku70 expression in human T-cell lymphomas. (A-C), B-cell lymphomas (D-F) and in human normal spleen (G). The photomicrograph of the spleen (paraffin) illustrates the nuclear staining against Ku70(G). (A) Photomicrograph illustrating a T-cell lymphoma (sample #T2—paraffin) with positive nuclear staining against Ku70, (B and C) Photomicrographs of T-cell lymphomas (samples #T13 and T9—paraffin and frozen, respectively) showing negative immunohistochemical staining against Ku70. In panel (C), the arrows point to endothelial cells with positive nuclear staining for Ku70, which served as internal positive controls. (D) Photomicrograph illustrating a B-cell lymphoma (sample #B4—paraffin) with positive nuclear staining against Ku70. (E) Photomicrograph of a B-cell lymphoma (sample #B8—paraffin) showing negative immunohistochemical staining against. Ku70. (F) Photomicrograph of a B-cell lymphoma (sample #B9—frozen) showing cytoplasmic staining of Ku70. Original magnification: A to G, 400×. (H) Representative PCR-SSCP analysis. Lane 3 illustrates the Ku70 band shift identified by PCR-SSCP corresponding to sample #T3. Lane 1, internal control (normal); lane 2, tumor corresponding to sample #T8, showing no band shift. Direct sequencing results of the PCR product obtained from tumor sample #T3 are shown below. The single base pair substitution (ACA→ATA) was found to be tumor-specific (absent in normal tissue) affecting codon 292, changing a threonine to isoleucine. (I) Representative RT-PCR direct sequencing from a T-cell lymphoma (sample #T3) and its corresponding normal tissue. Single base substitutions are indicated at codons 452 (ATC→GTC) and 453 (ATG→ACG), changing isoleucine to valine and methionine to threonine, respectively. These alterations were found to be tumor-specific and were absent in normal tissue. (J) Representative RT-PCR direct sequencing from a neuroblastoma (sample #N10) and its corresponding normal tissue. Single base substitutions are indicated at codon 530 (TAC→CAC) and codon 529 (GTT→GTC), changing tyrosine to histidine at codon 530, and producing a silent mutation at codon 529 (valine to valine), respectively. These mutations were also found to be tumor-specific and were absent in corresponding normal tissue.

FIG. 12

Effect of (A) radiation, (B) bleomycin, (C) Adriamycin, and (D) Etoposide on Ku70 and Ku80 deficient mouse cells.

FIG. 13

Effect of (A) radiation, and (B) adriamycin on different cell types. ○=HeLa controls cells; □=HeLa cells expressing antisense Ku70; ▲=HeLa cell expressing antisense Ku80.

FIG. 14

Nucleotide sequences of Vβ8Dβ2.1Jβ2.6 junctions from the thymus of a 4 week old Ku70−/− mouse (SEQ ID NOS: 1-23). Products corresponding to Vβ8.1, Vβ8.2 or Vβ8.3 rearrangement with Jβ2.6 were cloned and sequenced. TCR Vβ8-Jβ2 joints were amplified by PCR (20, 27, 28) as described (see FIG. 3B). PCR cycling conditions were 94° C. for 45", 68° C. for 30", and 72° C. for 30" (30 cycles). The band corresponding to Vβ8-Jβ2.6 was purified, reamplified for 20 cycles and then subcloned into the pCRII vector (Invitrogen). DNA was extracted from individual colonies and sequenced using the universal T7 and M13 reverse primers. Germline sequences are written in bold case, 'N' and 'P' denote nucleotides not present in the germline sequences.

FIG. 15

Inactivation of DNA-PKcs by homologous recombination. (A) Schematic diagram of the murine DNA-PKcs locus from exon 1 to 10 and hybridization probe (top), the targeting construct (middle), and the targeted allele. BamHI(B), EcoRI (E) and HindIII(H) restriction sites are indicated. (B) Southern blot of the BamHI-digested tail DNA from control wild-type (WT), heterozygous (+/−) and homozygous (−/−) DNA-PKcs-targeted mice. The wild-type and mutant fragments are 10 and 2.2 kb respectively. (C) RT-PCR of 5'-(exon 1-4) and 3'-(PI-3 kinase domain) regions of DNA-PKcs RNA from wild type, DNA-PKcs targeted, and SCID mouse cells. Total RNA was isolated from SV40 transformed lung fibroblast cells. PCR reactions were performed with (+) or without (−) reverse transcriptase (RT). RT-PCR for GAPDH was performed to ensure the RNA integrity. (D) Western blot analysis of the various cells. Whole cell extracts were prepared from primary and SV40 transformed lung fibroblast cells. Anti-DNA-PKcs monoclonal antibody and anti-Ku70 polyclonal antibody were used for detection. Note that there is another gene, MCM4, which is located about 700 bp upstream of DNA-PKcs. The transcription of DNA-PKcs and MCM4 are independently controlled by two distinct promoters located in this 700 bp region. We have carefully designed the DNA-PKcs knockout vector in exon 3, which is about 10 kb away from the promoter region, thus to avoid any possibility of interferring with the expression of MCM4 gene. Furthermore, we have also shown that truncated DNA-PKcs mRNA is expressed in DNA-PKcs−/− mice, confirming that the promoter region of the DNA-PKcs gene is not affected by our knockout construct.

FIG. 16

Development of lymphocytes is blocked at early stages in DNA-PKcs−/− mice. (A) Histological analysis of thymus (Thy), spleen (Spl) and lymph node (LN) from wild type and DNA-PKcs−/− mice (×200 magnification). Tissue sections were stained with hematoxylin and eosin. In tissue samples from DNA-PKcs-deficient mice, we observed effacement of normal histology and replacement by immature cells. The abbreviations are as follows: C, cortex; M, medulla; W, white pulp; R, red pulp; GC, germinal center. (B) Flow cytometric analysis of cells from the thymus (Thy), bone marrow (BM) and spleen (Spl) for the presence of precursor and mature T cells and B cells. Thymocytes and splenocytes were stained with fluorochrome-conjugated antibodies to CD4 and CD8; splenocytes and bone marrow cells were stained with fluorochrome-conjugated antibodies to B220 and IgM or CD43. Profiles shown are representative results from a 4- to 5-week-old DNA-PKcs−/− mouse, its heterozygous littermate, and an age-matched CB-17 SCID mouse. (C) TCR and Immunoglobulin gene rearrangement in DNA-PKcs−/− mice. (a) TCRβ rearrangement by PCR analysis. Thymus and Spleen DNA were assayed for recombination of $V_\beta 8$-$J_\beta 2.6$.

Both the quantity and the diversity of $TCR_\beta$ rearrangement were reduced in DNA-PKcs−/− and SCID mice. (b) Coding joint of $TCR_\beta$ rearrangement. Thymus and spleen DNA were assayed for recombination of $D_\delta 2$-$J_\delta 1$. (c) Signal joint of $TCR_\delta$ rearrangement. Thymus DNA was assayed for $D_\delta 2$-$J_\delta 1$ circular signal joint products. There is more amplified signal for both DNA-PKcs−/− and SCID mice than heterozygous control mice. (e) Immunoglobulin heavy chain rearrangement by PCR analysis. Bone marrow(BM) and spleen DNA were used for recombination of $V_H 7183$-$J_H 4$. Rearrangement in DNA-PKcs−/− and SCID is severely reduced in both BM and spleen. (d) and (f) Control GAPDH amplification from thymus, spleen and bone marrow (BM) DNA. DNA (100, 10 or 1 ng) from the thymus, spleen and bone marrow (BM) or a 5-week-old DNA-PKcs+/−mouse (lane 1-3), of a 9-week-old DNA-PKcs+/−mouse (lane 4-6), and 100 ng DNA of three individual DNA-PKcs−/− mice (lane 7-9) and three individual SCID mice (lane 10-12). DNA-PKcs−/− and SCID mice analyzed were also between 4-9 weeks of age.

FIG. 17

Radiation dose response of DNA-PKcs−/− cells. Clonogenic survival were measured on SV40-transformed mouse lung fibroblasts irradiated with graded doses of ionizing radiation. DNA-PKcs−/− cells show similar sensitivity tp ionizing radiation as SCID and are much more sensitive than wild type (+/+) and heterozygous (+/−) cells.

FIG. 18

Preneoplastic lesions in DNA-PKcs−/− mice. Intestinal tissue samples from 6-week to 6-month old DNA-PKcs−/− mice were sectioned, stained with hematoxylin and eosin, and photographed. (A) Section of intestinal tissue showing inflammation and mild epithelial hyperplasia (×100 magnification). (B) Photomicrograph of colonic mucosa showing crypt hyperplasia with mild to moderate dysplasia (×200 magnification). (C) Adenomatous polyp of the colon showing areas of severe dysplasia (×400 magnification). (D) Aberrant crypt foci along the intestinal mucosa showing severe dysplasia (×400 magnification). (E) Section of intestinal tissue from a wild-type mouse showing-normal morphology (×250 magnification).

DETAILED DESCRIPTION OF THE INVENTION

This invention provides a method for increasing the susceptibility of a cell to DNA-damaging agents, comprising introducing into the cell an antisense oligonucleotide that specifically hybridizes to a nucleic acid encoding a DNA dependent protein kinase subunit so as to prevent expression of the DNA dependent protein kinase subunit; wherein the antisense oligonucleotide is in an amount sufficient to increase the sensitivity of the cell to heat, chemical, or radiation-induced DNA damage; and wherein the DNA dependent protein kinase subunit is a DNA dependent protein kinase catalytic subunit, a Ku70, or a Ku80.

Methods to introduce a nucleic acid into cells have been well known in the art. Naked nucleic acid may be introduced into the cell by direct transformation. Alternatively, the nucleic acid molecule may be embedded in liposomes. Accordingly, this invention provides the above methods wherein the nucleic acid is introduced into the cells by naked DNA technology, adenovirus vector, adeno-associated virus vector, Epstein-Barr virus vector, Herpes virus vector, attenuated HIV vector, retroviral vectors, vaccinia virus vector, liposomes, antibody-coated liposomes, calcium phosphate coprecipitation, mechanical or electrical means (i.e. electroporation). The above recited methods are merely served as examples for feasible means of introduction of the nucleic acid into cells. Other methods known may be also be used in this invention.

This invention also provides the above-described method, wherein the antisense oligonucleotide is enclosed in a liposome prior to introduction into the cell.

This invention also provides a method of treating a tumor in a subject, comprising administering to the subject an antisense oligonucleotide that specifically hybridizes to a nucleic acid encoding a DNA dependent protein kinase subunit so as to prevent expression of the DNA dependent protein kinase subunit; wherein the antisense oligonucleotide is in an amount sufficient to increase the sensitivity of the tumor to heat, chemical or radiation-induced DNA damage; and wherein the DNA dependent protein kinase subunit is a DNA dependent protein kinase catalytic subunit, a Ku70, or a Ku80.

As used herein, administering may be effected or performed using any of the various methods known to those skilled in the art. The administering may comprise administering intravenously. The administering may also comprise administering intramuscularly. The administering may further comprise administering subcutaneously. The administering may also comprise administering orally.

This invention also provides the above-described method, wherein the antisense oligonucleotide is enclosed in a liposome prior to being administered to the subject.

This invention further provides the above-described methods, wherein the administering to the subject an antisense oligonucleotide comprises: administering to the subject an expression vector for the antisense oligonucleotide; and inducing the expression of the antisense oligonucleotide.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MOMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation. Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells.

Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk⁻ cells and COS cells. Mammalian cells may be transfected by methods well known in the art such as calcium phosphate precipitation, electroporation and microinjection.

In an embodiment, inducible promoters may be fused with the coding region of the DNA to provide an experimental means to regulate expression. Alternatively or in addition, tissue specific regulatory elements may be Fused with the coding region to permit tissue-specific expression.

This invention provides the above-described methods, further comprising administering to the subject one or more DNA-damaging agents.

This invention also provides the above-described methods, wherein the DNA-damaging agents are adriamycin, bleomycin, or etoposide.

This invention further provides the above-described methods, wherein the DNA-damaging agents induce double strand breaks.

This invention also provides a method for treating cancer in a subject, comprising: introducing into the subject an expression vector comprising a heat shock promoter and an antisense oligonucleotide that specifically hybridizes to a nucleic acid encoding a DNA dependent protein kinase subunit so as to prevent expression of the DNA dependent protein kinase subunit; and inducing expression of the antisense oligonucleotide, wherein the antisense oligonucleotide is in an amount sufficient to increase the sensitivity of the cell to heat, chemical, or radiation-induced DNA damage; and wherein the DNA dependent protein kinase subunit is a DNA dependent protein kinase catalytic subunit, a Ku70, or a Ku80.

In an embodiment, the heat shock promoter may have some activity at 37° C. but will become more active at some higher temperature (i.e. 45° C.). In another embodiment the heat shock promoter may have no activity at 37° C. but will become active at some higher temperature (i.e. 43° C.).

This invention also provides the above-described methods, wherein the antisense oligonucleotide is introduced selectively at sites of cancer.

Sites of cancer include sites at or near cells exhibiting a malignant transformation phenotype.

This invention provides the above-described methods, further comprising directing heat, radiation, or chemotherapy at sites of cancer.

This invention further provides the above-described methods, further comprising applying electric field energy to sites of cancer.

This invention also-provides the above-described methods, wherein the electric field energy comprises radiofrequency radiation.

This invention provides the above-described methods, further comprising implanting a reservoir of chemotherapeutic agents near sites of cancer, wherein the chemotherapeutic agents are releasable over a period of time of at least eight hours.

In an embodiment, the chemotherapeutic agents are encapsulated before implantation.

This invention provides an antisense oligonucleotide that specifically hybridizes to a nucleic acid encoding a DNA dependent protein kinase subunit, wherein the DNA dependent protein kinase subunit is a DNA dependent protein kinase catalytic subunit, Ku70, or Ku80, so as to prevent expression of the DNA dependent protein kinase subunit.

This invention also provides the above-described antisense oligonucleotide linked to a substance which inactivates mRNA.

In addition, this invention provides the above-described antisense oligonucleotides, wherein the substance which inactivates mRNA is a ribozyme.

This invention provides the above-described antisense oligonucleotides linked to a regulatory element.

Regulatory elements include, but are not limited to, promoter sequences to bind RNA polymerase and transcription initiation sequences for ribosome binding.

Additional elements may also be needed for optimal synthesis of mRNA. These additional elements may include, but are not limited to, splice signals, as well as enhancers and termination signals.

This invention also provides the above-described antisense oligonucleotides, wherein the regulatory element is an inducible promoter.

This invention provides the above-described antisense oligonucleotides, wherein the regulatory element is a heat shock promoter.

In addition, this invention provides an expression vector adapted for the expression of the above-described antisense oligonucleotides.

This invention also provides a pharmaceutical composition comprising any of the above-described antisense oligonucleotides and a carrier.

Pharmaceutically acceptable carriers are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention further provides the above-described pharmaceutical composition, wherein the carrier is adapted for passage through a plasma cell membrane.

This invention will be better understood from the examples which follow. However, one skilled in the art will readily appreciate that the specific methods and results discussed are merely illustrative of the invention as described more fully in the claims which follow thereafter.

EXPERIMENTAL DETAILS

First Series of Experiments

Material and Methods

Target Disruption of Ku70 and Generation of Ku70$^{-/-}$ Mice

Mouse genomic Ku70 gene was isolated from a sCos-I cosmid library constructed from a mouse strain 129 embryonic stem cell lines (21). The replacement vector was constructed using a 1.5 kb 5'-fragment which contains the promoter locus with four GC-box and exon 1, and a 8 kb EcoRV-EcoRI fragment extending from intron 2 to intron 5 as indicated in FIG. 1a. Homologous replacement results in a deletion of 336-bp exon 2 including the translational initiation codon.

The targeting vector was linearized with NotI and transfected into CJ7 embryonic stem (ES) cells by electroporation using a Bio-Rad Gene Pulser. Three hundred ES cell clones were screened, and 5 clones carrying the mutation in Ku70 were identified by Southern blotting. Positive ES clones were injected separately into C57BL/6 blastocysts to generate chimeric mice. One clone was successfully transmitted through the germline after chimeras were crossed with C57 BL/6 females. Homozygous Ku70–/– mice were generated by crossing Ku70+/–heterozygotes.

The genotype of the mice was first determined by tail PCR analysis which distinguishes endogenous from the targeted Ku70 allele, and subsequently confirmed by Southern blot analysis. The PCR reaction contained 1 μg genomic DNA; 0.6 μM (each) of primers HO-2: GGGCCAGCTCATTCCTC-CACTCATG, (SEQ ID NO: 24), HO-3: CCTACAGTGTAC-CCGGACCTATGCC (SEQ ID NO: 25) and HO-4: CGGAA-CAGGACTG-GTGGTTGAGCC (SEQ ID NO: 26); 0.2 mM (each) dNTP; 1.5 mM MgCl$_2$ and 2.5 U of Taq polymerase. Cycling conditions were 94° C. for 1 min, 64° C. for 1 min, 72° C. for 1 min (30 cycles), followed by an extension at 72° C. for 10 min. Primers HO-2 and HO-4 give a product of the targeted allele that is –380 bp; primers HO-3 and HO-4 yield a wild type product of 407 bp.

Western Blot Analysis and Gel Mobility Shift Assay

To confirm that the disruption of Ku70 produces a null mutation, Ku70 protein expression was measured by Western blotting using polyclonal antisera against intact mouse Ku70. The lack of Ku70 was also verified by a Ku-DNA-end binding assay (gel mobility shift analysis). Cell extracts were prepared and gel mobility shift assays were performed as described (22). Equal amounts of cellular protein (50 μg) from Ku70+/+(WT), Ku70+/–, and Ku70–/– mouse embryo fibroblasts were incubated with a $^{32}$P-labeled double-stranded oligonucleotide, 5'-GGGCCAAGAATCTTCCAG-CAGTTTCGGG-3'(SEQ ID NO: 27). The protein-bound and free oligonucleotides were electrophoretically separated on a 4.5% native polyacrylamide gel. Gel slabs are dried and autoradiographed with Kodak X-Omat film.

Immunohistochemistry

To determine the pathological changes, histological sections of various organs of Ku70–/–, Ku80–/– and wild type littermate mice were prepared and examined as previously described (23). Lymph nodes, spleens and thymuses from 4- to 5-week-old mice were fixed in 10% buffered formalin and embedded in paraffin, or embedded in OCT compound (Miles Laboratories) and frozen in liquid nitrogen at −70° C. Sections (5 μm) were stained with hematoxylin and eosin, and representative samples were selected for immunohistochemical analysis. Immunophenotyping was performed using an avidin-biotin immunoperoxidase technique (24). Primary antibodies included anti-CD3 (purified rabbit serum, 1:1000, Dako), anti-B220 (rat monoclonal, 1:1000, Pharmingen) anti-CD19 (rat monoclonal, 1:1000, Pharmingen), and were incubated overnight at 4° C. Samples were subsequently incubated with biotinylated secondary antibodies (Vector Laboratories) for 30 min (goat anti-rabbit, 1:100; rabbit anti-rat, 1:100), and then with avidin-biotin peroxidase (1:25 dilution, Vector Laboratories) for 30 min. Diaminobenzadine was used as the chromogen and hematoxylin as the counter stain. Wild type lymphoid organs including thymus, spleen and lymph nodes from different mice were used for titration of the antibodies and positive controls. Anti-CD3 and anti-CD19 antibodies were tested in both frozen and paraffin sections of wild-type lymphoid organs and showed the expected specific patterns of staining. For negative controls, primary antibodies were substituted with class-matched but unrelated antibodies at the same final working dilutions.

Cell Preparation and Flow Cytometric Analysis

For flow cytometry, single cell suspensions from lymphoid organs of 4- to 6-week-old mutant and littermate control mice were prepared for staining as described previously (19) and analyzed on a Becton Dickinson FACs Scan with Cell Quest software. Cells were stained with combinations of phycoerythrin-(PE) labeled anti-CD4, and fluorescein (FITC)-labeled anti-CD8, or PE labeled anti-B220, and FITC-labeled anti-CD43, or FITC anti-μ and PE anti-B220 (Pharmingen), as needed. Bone marrow cells were harvested from femurs by syringe lavage, and cells from thymus and spleen were prepared by homogenization. Cells were collected and washed in PBS plus 5% FCS and counted using a hemacytometer. Samples from individual mice were analyzed separately. Dead cells were gated out by forward and side scatter properties. Experiments were performed at least three times and yielded consistent results.

DNA Preparation and Analysis of V(D)J Recombination Products

To determine whether a null mutation in Ku70 affects the recombination of antigen-receptor genes in T and B lymphocytes in vivo, we measured the immunoglobulin and T-cell antigen receptor (TCR) rearrangements by PCR. DNA from bone marrow was amplified with primers specific to immunoglobulin D-J$_H$ and V-DJ$_H$ rearrangements, and DNA from thymus was amplified with primers that detect V-DJ$_\beta$ and D$_\delta$-J$_\delta$-rearrangement (20, 25-28). Oligonucleotides for probes and PCR primers specific to TCR Vβ-Jβ rearrangements and immunoglobulin D-J$_H$ and V-DJ$_H$ rearrangements are as follows. For TCRβ Vβ8-Jβ2 rearrangements (28): Vβ8.1: 5'-GAGGAAAGGT-GACATTGAGC-3'(SEQ ID NO: 28), Jβ2.6: 5'-GCCTGGTGCCGGGACCGAAGTA-3' (SEQ ID NO: 29), Vβ8 probe: 5'-GGGCTG AGGCTG ATC-CATTA-3'(SEQ ID NO: 30). For D$_{\delta 2}$-J$_{\delta 1}$ rearrangement (20, 27): DR6: 5'-TGGCTTGACATGCAGAAAACACCTG-3' (SEQ ID NO: 31), DR53: 5'-TGAATTCCACAG-TCACT-TGGCTTC-3'(SEQ ID NO: 32), and DR2 probe: 5'-GA-CACGTGATACAAAGCCCAGGGAA-3'(SEQ ID NO: 33). For immunoglobulin D-J$_H$ and V-DJ$_H$ rearrangements (26): 5'D: 5'-GTCAAGGGATCTACTACTGTG-3'(SEQ ID NO: 34), V7183: 5'-GAGAGAATTCAGAGACAATC-CCAA-GAACACCCTG-3'(SEQ ID NO: 35), VJ558L: 5'-GAGAGAATTCTCCTCCAGCACAG-CCTACATG-3' (SEQ ID NO: 36), J2: 5'-GAGAGAATTCGGCTCCCAAT-GACCCTTTCTG-3', 5'(SEQ ID NO: 37)5-IVS: 5'-GTAA-GAATGGCCTCTCCAGGT-3'(SEQ ID NO: 38), 3'-IVS:

5'-GACTCAATCACTAAGACA-GCT-3'(SEQ ID NO: 39), and probe: a 6 kb EcoR I fragment covering the J region of mouse IgM.

Cell Survival Determination 8- to 10-week-old Ku70−/− and Ku80−/− mice and wild type littermates were used for our studies. Bone marrow cell suspensions were prepared by flushing the femur with MEM supplemented with 15% fetal calf serum (FCS). The cell suspension was then counted using a hemacytometer and centrifuged at 1000 rpm for 12 min. The resulting pellet was resuspended and diluted to approximately $1 \times 10^6$ cells/ml in MEM plus 15% FCS for further experiments.

To measure the survival of granulocyte-macrophage progenitors, the method of Van Zant et al. (29) was used with minor modifications (30). Briefly, α-MEM contained 30% heat-inactivated FCS and 1% bovine serum albumin; in addition, 0.5 ng/ml GM-CSF (R & D Systems) was used as a source of colony-stimulating factor. One day before each experiment, 2.0 ml of the above media containing 0.5% noble agar (DIFCO Laboratories) was added to individual 60-mm petri dishes. Immediately after radiation exposure, cells were diluted in 2 ml of the above media with 0.3% noble agar and poured over the prepared dishes with 0.5% noble agar underlayer. The cells were then incubated at 37° C. with 5% $CO_2$ and 95 to 98% humidity. The colonies were counted on Day 8 with a dissecting microscope. Macrophage and granulocyte colonies were counted separately and then summed together for survival calculations of granulocyte-macrophage progenitors (CFU-GM). Only colonies containing 50 or more cells were scored. The colony forming efficiency of CFU-GMs was 60 to 100/105 nucleated cells for untreated controls. Surviving fraction was defined as the cloning efficiency of irradiated marrow cells relative to that of untreated controls. All experiments were performed at least twice and yielded consistent results.

Asymmetric Field Inversion Gel Electrophoresis

To determine the rate and extent of DNA DSB repair in Ku-deficient cells after exposure to ionizing radiation, primary embryo fibroblasts derived from Ku70−/−, Ku80−/− and wild type littermate mice were used. Mouse embryo fibroblasts from 13.5-day embryos growing in replicate cultures for 3 days in the presence of 0.01 μCi/ml $^{14}$C-thymidine (NEN) and 2.5 μM cold thymidine were exposed to 40 Gy of X-rays and returned to 37° C. At various times thereafter, one dish was removed and trypsinized on ice; single cell suspensions were made and embedded in an agarose plug at a final concentration of $3 \times 10^6$ cells/ml. AFIGE (Asymmetric Field Inversion Gel Electrophoresis) was carried out in 0.5% Seakem agarose. (FMC, cast in the presence of 0.5 μg/ml ethidium bromide) in 0.5×TBE (45 mM Tris, pH 8.2, 45 mM boric acid, 1 mM EDTA) at 10° C. for 40 h, by applying cycles of 1.25 V/cm for 900 sec in the direction of DNA migration, and 5.0 V/cm for 75 sec in the reverse direction as described (31). Quantification and analysis for DNA DSB present were carried out in a PhosphorImager (Molecular Dynamics). Levels of DNA double-strand breaks (DSB) were quantified by calculating the FAR (fraction of activity released from the well into the lane) in irradiated and unirradiated samples, which equals the ratio of the radioactivity signal in the lane versus that of the entire sample (well plus lane)

EXPERIMENTAL RESULTS

Targeted Disruption of Ku70 Gene

To study the role of Ku70 in vivo, we generated mice containing a germline disruption of the Ku70 gene. Murine genomic Ku70 gene was isolated and a targeting vector was constructed (FIG. 1a). Homologous replacement results in a deletion of 336-bp exon 2 including the translational imitation codon. Two targeted ES clones carrying the mutation in Ku70 were injected into C57BL/6 blastocysts to generate chimeric mice. One clone was successfully transmitted through the germline after chimeras were crossed with C57BL/6 females. No obvious defects were observed in Ku70+/−heterozygotes, and these Ku70+/−mice were subsequently used to generate Ku70−/− mice (FIG. 1b). 25% of the offspring born from Ku70+/−×Ku70+/−crosses were Ku70−/−. Adult Ku70−/− mice are fertile, but give reduced litter size (2 to 4 pups) as compared to the $Ku70^{+/-}$ or $Ku70^{+/+}$ mice (about 8 pups).

Figure 1D:
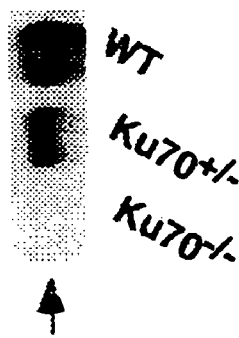
Figure 1C:
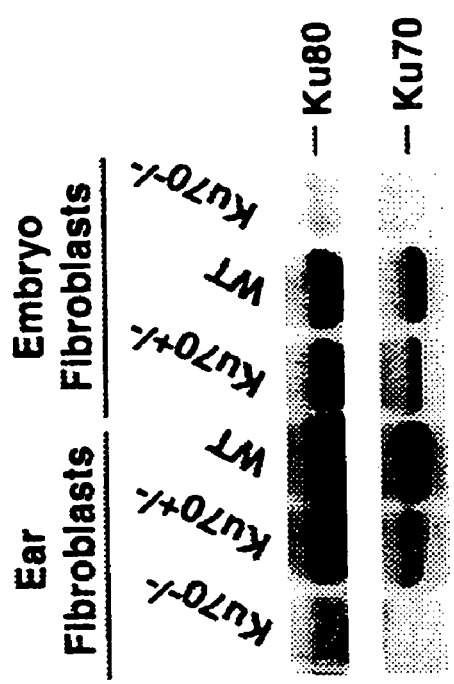
Figure 1B:
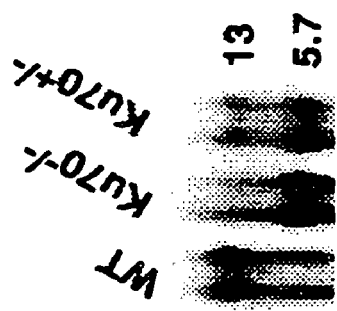

To confirm that the disruption produced a null mutation, Ku70 protein expression was analyzed by both Western blotting (FIG. 1C) and a DNA end binding assay (FIG. 1D). Ku70 immunoreactivity was undetectable (FIG. 1C), and there was no Ku DNA-end binding activity in Ku70−/− fibroblasts (FIG. 1D). The Ku80 subunit of the Ku heterodimer was found, but at much reduced levels (FIG. 1C), suggesting that the stability of Ku80 is compromised by the absence of Ku70. Those observations are consistent with the finding that the level of Ku70 was significantly reduced in Ku80−/− fibroblasts and Ku80−/− ES cells (19). Taken together, these data suggest that the stability of either component of Ku is compromised by the absence of the other.

Newborn Ku70−/− mice were 40-60% smaller than their Ku70+/−and Ku70+/+littermates. During a 5-month observation period, Ku70−/− mice grew and maintained body weight at 40-60% of controls. Thus Ku70−/− mice, like Ku80−/− mice are proportional dwarfs (19).

Development of B Lymphocyte, but not T Lymphocyte, is Blocked at Early Stage in Ku70$^{-/-}$ Mice Examination of various organs from Ku70−/− mice showed abnormalities only in the lymphoid system (FIG. 2A). Spleen and lymph nodes were disproportionately smaller by 5-10 fold relative to controls. In particular, splenic white pulp nodules were significantly reduced. Immunohistochemistry on deparaffinized tissue sections revealed that the splenic white pulp contained cells that stained with anti-CD3 (i.e., CD3 positive T cells), but there were no CD19 positive B cells (FIG. 2A, panels k and n). The Ku70−/− thymus was also disproportionately smaller and contained 100-fold fewer lymphocytes than Ku70+/+littermates ($2 \times 10^6$ in the former versus $2 \times 10^8$ in the latter; measured in 3 mice of each genotype). In contrast to the Ku80−/− mice, the Ku70−/− thymus displayed normal appearing cortical-medullary junctions (FIG. 2A, panels g and j). Overall, the lymphoid tissues and organs of Ku70−/− mice are somewhat disorganized and much smaller than Ku70+/+mice (Table I); yet, they are relatively more developed and slightly larger than in Ku80$^{-/-}$ mice.

TABLE I

| | Lymphoid Cellularity of Ku70$^{-/-}$ Mice | | |
|---|---|---|---|
| Tissue and genotype | Cell content (×1 million) Total | Cell content (×1 million) B220+ | Cell content (×1 million) CD4 + CD8+ |
| Thymus | | | |
| wild type (n = 4) | 155 +/− 42 | — | 104 +/− 28 |
| Ku70−/− (n = 3) | 2.98 +/− 0.91 | — | 0.6 +/− 0.2 |
| Ku80−/− (n = 2) | 1.0 +/− 0.5 | — | — |

TABLE I-continued

Lymphoid Cellularity of Ku70−/− Mice

| Tissue and genotype | Cell content (×1 million) Total | Cell content (×1 million) B220+ | Cell content (×1 million) CD4 + CD8+ |
|---|---|---|---|
| Bone Marrow | | | |
| wild type (n = 4) | 11.9 +/− 3.3 | 5.5 +/− 1.5 | — |
| Ku70−/− (n = 3) | 7.2 +/− 2.9 | 1.1 +/− 0.4 | — |
| Ku80−/− (n = 2) | 9.0 +/− 3.0 | — | — |
| Spleen | | | |
| wild type (n = 4) | 53 +/− 20 | 29 +/− 11 | — |
| Ku70−/− (n = 3) | 6.5 +/− 1.3 | 0.4 +/− 0.2 | — |
| Ku80−/− (n = 2) | 1.2 +/− 0.5 | — | — |

Data shown are arithmetic means ± standard deviations from 2-4 individuals of each genotype analyzed at 4 to 6 weeks of age. Cell numbers are shown per femur for bone marrow, and per whole organ for spleen and thymus.

Figures 1, 2, 2B, 3:
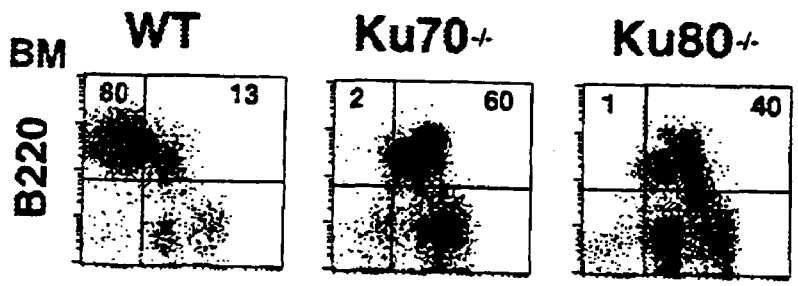

To further examine the immunological defect in Ku70−/− mice, cells from thymus, bone marrow and spleen were analyzed using monoclonal antibodies specific for lymphocyte surface markers and flow cytometry (19). Consistent with the immunohistological data there was a complete block in B-cell development at the B220$^+$CD43$^+$ stage in the bone marrow, and there were no mature B cells in the spleen (FIG. 2B). In contrast, thymocytes developed through the CD4$^+$CD8$^+$ double-positive (DP) stage and matured into CD4$^+$CD8$^-$ and CD4$^-$CD8$^+$ single-positive (SP), TCRβ positive cells (FIG. 2B, C). In six four-week old Ku70−/− mice analyzed the percentage of CD4$^-$CD8$^-$ double-negative thymocytes ranged from 11-62%, and the CD4$^+$CD8$^-$ DP cells varied from 35, 73%. CD4$^-$CD8$^+$ (1-11%) and CD4$^+$CD8$^-$ (1-3%) SP cells were also detected in the thymus. Furthermore, CD4$^+$ CD8$^-$ or CD4$^-$CD8$^+$, single-positive T cells were found in the spleen in 67% of the mice studied (FIG. 2B), which expressed surface TCRβ (FIG. 2C) and CD3. Thus, in contrast to the early arrest of both T- and B-cell development in Ku80−/− mice (FIG. 2B), lack of Ku70 is compatible with the maturation of T cells.

T-Cell Receptor and Immunoglobulin Gene Rearrangement

To determine whether a null mutation in Ku70 affects antigen-receptor gene recombination, DNA from bone marrow was amplified with primers specific to immunoglobulin D-J$_H$ and V-DJ$_H$ rearrangements and DNA from thymus was amplified with primers that detected V-DJ$_H$ and D-J$_H$ rearrangements (20, 25-28). FIG. 3A shows that Ku70−/− B cells do undergo D-J$_H$ recombination, at a level which is similar to Ku80−/− B cells, but is 2- to 3-fold lower than the level found in scid mice, and 10-50-fold lower than wild type littermates. It is possible that some, but not all, of the decrease in D-J$_H$ rearrangement is due to a lower fraction of B-lineage cells in the mutant sample, since the wild littermate mice have only ~5-fold more B220$^+$ cells than the Ku70−/− mice (see Table I). V-DJ$_H$ rearrangements were not detected in either Ku70−/−, Ku80−/−, or scid bone marrow samples, possibly accounting for the absence of mature B cells in these mutant mice (FIG. 3A).

Figure 3B:
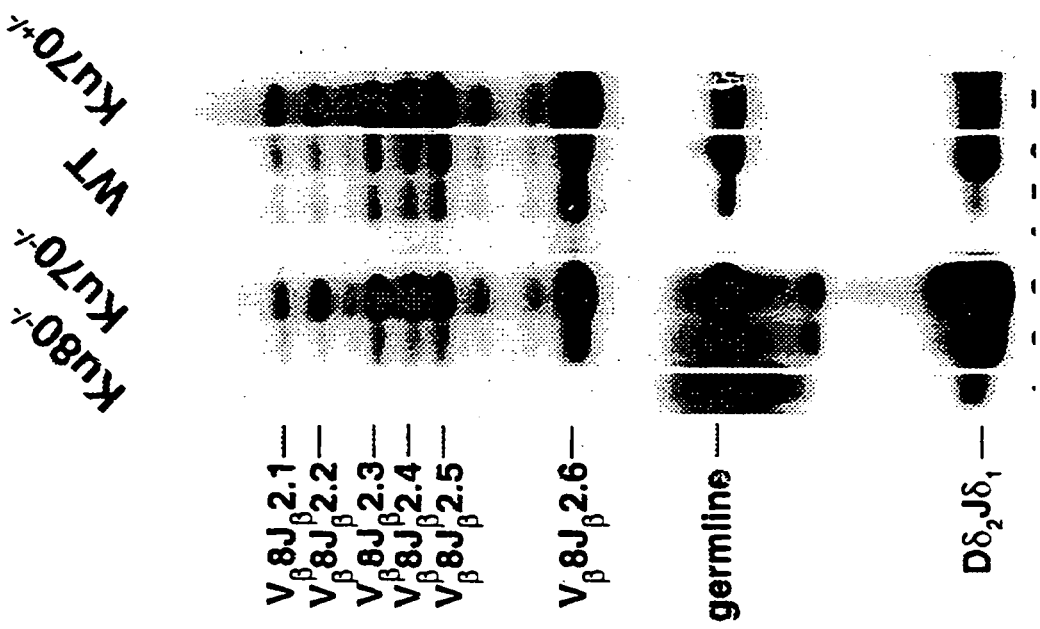
Figure 3A:
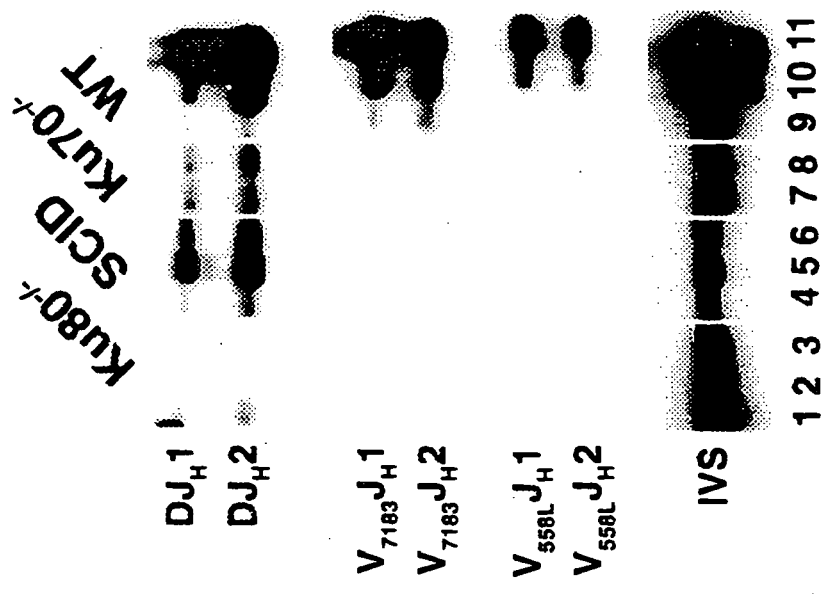

In contrast to the immunoglobulin heavy chain gene recombination, semiquantitative PCR analysis of thymocyte DNA for V-DJ$_β$ joints showed normal levels of TCR$_β$ rearrangements on a per cell basis (FIG. 3B). Similarly, D$_δ$2 and J$_δ$1 coding joints were found in Ku70−/− thymocytes at levels that resembled the wild type. To determine the molecular nature of the amplified coding joints, cloned V$_δ$8-DJ$_δ$2.6 joints were sequenced. We found normal numbers of N, and P nucleotides as well as normal levels of coding end deletions (FIG. 14). Thus, coding joints in Ku70−/− thymocytes differ from coding joints produced in xrs6 Ku80-deficient cells in that there were no large aberrant deletions (4, 18). We conclude that TCR V(D)J recombination in vivo does not require Ku70.

Absence of Ku70 Confers Radiation Hypersensitivity and Deficiency in DNA DSB Repair To assess radiation sensitivity in the absence of Ku70, cells from the bone marrow were exposed to ionizing radiation, and were assayed for colony formation (30, 32). FIG. 4A shows the survival curves of the granulocyte/macrophage colony forming units (CFU-GM) from Ku70−/−, Ku80−/− and wild type control mice. CFU-GM from Ku70-deficient mice were more sensitive to ionizing radiation than those from Ku-proficient control mice (FIG. 4A). Similar hypersensitivity to radiation was seen for Ku80$^{-/-}$ CFU-GM (FIG. 4A).

The rate and extent of rejoining of X-ray-induced DNA DSB in Ku70−/−, Ku80−/− and Ku70+/+cells were measured using asymmetric field inversion gel electrophoresis (AFIGE) (31). Fibroblasts derived from 13.5-day embryos were exposed to 40 Gy of X-rays and returned to 37° C. for repair. At various times thereafter cells were prepared for AFIGE to quantitate DNA DSB (FIG. 4B, upper panel). DNA DSB were nearly completely rejoined in wild type cells within about 2 h after radiation exposure. However, fibroblasts derived from Ku70−/− mice showed a drastically reduced ability to rejoin DNA DSB. A similar deficiency in DNA DSB rejoining was also observed in fibroblasts derived from Ku80−/− embryos. Despite the large differences observed in rejoining of DNA DSB between wild type fibroblasts and fibroblasts derived from Ku70−/− or Ku80−/− mouse embryos, dose-response experiments showed that Ku70−/−, Ku80−/− and wild type fibroblasts were equally susceptible to X-ray-induced damage (FIG. 4B, lower panel). Thus, Ku deficiency affects primarily the ability of cells to rejoin radiation-induced DNA DSB without significantly affecting the induction of DNA damage.

EXPERIMENTAL DISCUSSION

Absence of Ku70 results in radiation hypersensitivity, proportional dwarfism, as well as deficiencies in DNA DSB repair and V(D)J recombination. Thus, Ku70−/− mice resemble Ku80−/− mice in several respects but the two mutations differ in their effects on T and B cell development. Lack of Ku70 was compatible with TCR gene rearrangement and development of mature CD4$^+$CD8$^-$ and CD4$^-$ CD8$^+$ T cells, whereas mature T cells were absent in Ku80−/− mice. In contrast, B cells failed to complete antigen receptor gene rearrangement and did not mature in either Ku70−/− or Ku80−/− mice.

What could account for the differences we find in TCR and immunoglobulin gene rearrangements in the Ku70−/− mice? One implication of our findings is that there are alternative Ku70-independent rescue pathways that are compatible with completion of V(D)J recombination in T cells. It is likely at the critical phase of T cell maturation, other DNA repair activity may be stimulated (33, 34) and can functionally complement the Ku70 gene in T cell-specific V(D)J recombination. Since Ku80−/− mice are deficient in both T and B lymphocyte development, it is plausible that these yet to be identified alternative DNA repair pathways include Ku80. The much reduced level of Ku80 protein in Ku70−/− cells may in part account for the hypocellularity of Ku70$^{-/-}$ thymii Although the role of Ku in V(D)J recombination is not molecularly defined, Ku has been proposed to protect DNA ends from degradation (18, 35), to activate DNA-PK (10, 11), and to dissociate the RAG/DNA complex to facilitate the joining reaction (20). These functions are not mutually exclusive, and they are all dependent on the interaction of Ku with DNA. Thus, the finding that Ku70 is not required for TCR gene rearrangement is particularly unexpected, because the Ku70 subunit is believed to be the DNA-binding subunit of the Ku complex (36), and DNA-end binding activity was not detected in Ku70-deficient cells (FIG. 1D).

In summary, our studies provide direct evidence supporting the involvement of Ku70 in the repair of DNA DSB and V(D)J recombination, and the presence of a Ku70-independent rescue pathway(s) in TCR V(D)J rearrangement. The distinct phenotype of Ku70−/− mice should make them valuable tools for unraveling the mechanism(s) of DNA repair and recombination.

References of the First Series of Experiments

1. Li, Z., T. Otevrel, Y. Gao, H.-L. Cheng, B. Sneed, T. Stamato, G. Taccioli, and F. W. Alt. 1995. The XRCC4 gene encodes a novel protein involved in DNA double-strand break repair and V(D)J recombination. *Cell* 83: 1079-1089.
2. Hendrickson, E. A., X.-Q. Qin, E. A. Bump, D. G. Schatz, M. Oettinger, and D. T. Weaver. 1991. A link between double-strand break-related repair and V(D)J recombination: The scid mutation. *Proc. Natl. Acad. Sci. USA* 88:<4061-4065.
3. Pergola, F., M. Z. Zdzienicka, and M. R. Lieber. 1993. V(D)J recombination in mammalian cell mutants defective in DNA double-strand break repair. *Mol. Cell. Biol.* 13: 3464-3471.
4. Taccioli, G. E., G. Rathbun, E. Oltz, T. Stamato, P. A. Jeggo, and F. W. Alt. 1993. Impairment of V(D)J recombination in double-strand break repair mutants. Science 260: 207-210.
5. Roth, D. B., T. Lindahl, and M. Gellert. 1995. *Curr. Biol.* 5: 496.
6. Bogue, M., and D. B. Roth. 1996. *Current Opinions in Cell Biol* 8: 175.
7. Jeggo, P. A., G. A. Taccioli, and S. P. Jackson. 1995. Menage a trois: double strand break repair, V(D)J recombination and DNA-PK. *BioEssays* 17: 949-956.
8. Weaver, D. T. 1995. What to do at an end: DNA double-strand-break repair. TIGS 11: 388-392.
9. Biedermann, K. A., J. Sun, A. J. Giaccia, L. M. Tosto, and J. M. Brown. 1991. scid mutation in mice confers hypersensitivity to ionizing radiation and a deficiency in DNA double-strand break repair. *Proc. Natl. Acad. Sci. USA* 88: 1394-1397.
10. Dvir, A., S. R. Peterson, M. W. Knuth, H. Lu, and W. S. Dynan. 1992. Ku autoantigen is the regulatory component of a template-associated protein kinase that phosphorylates RNA polymerase II. *Proc. Natl. Acad. Sci. USA* 89: 11920-11924.
11. Gottlieb, T. M., and S. P. Jackson. 1993. The DNA-dependent protein kinase: requirement for DNA ends and association with Ku antigen. *Cell* 72: 131-142.
12. Lees-Miller, S. P. 1996. The DNA-dependent protein kinase, DNA-PK: 10 years and no ends in sight. *Biochem. Cell Biol.* 74: 503-512.
13. Peterson, S. R., A. Kurimasa, M. Oshimura, W. S. Dynan, E. M. Bradbury, and D. J. Chen. 1995. Loss of the catalytic subunit of the DNA-dependent protein kinase in DNA double-strand-break-repair mutant mammalian cells. *Proc. Natl. Acad. Sci. USA* 92: 3171-3174.
14. Kirchgessner, C. U., C. K. Patil, J. W. Evans, C. A. Cuomo, L. M. Fried, T. Carter, M. A. Oettinger, and J. M. Brown. 1995. DNA-dependent kinase (p350) as a candidate gene for the murine SCID defect. *Science* 267: 1178-1183.
15. Blunt, T., N. J. Finnie, G. E. Taccioli, G. C. M. Smith, J. Demengeot, T. M. Gottlieb, R. Mizuta, A. J. Varghese, F. W. Alt, P. A. Jeggo, and S. P. Jackson. 1995. Defective DNA-dependent protein kinase activity is linked to V(D)J recombination and DNA repair defects associated with the murine scid mutation. Cell 80: 813-823.
16. Boubnov, N. V., K. T. Hall, Z. Wills, S. E. Lee, D. M. He, D. M. Benjamin, C. R. Pulaski, H. Band, W. Reeves, E. A. Hendrickson, and D. T. Weaver. 1995. Complementation of the ionizing radiation sensitivity, DNA end binding, and V(D)J recombination defects of double-strand break repair mutants by the p86 Ku autoantigen. *Proc. Natl. Acad. Sci. USA* 92: 890-894.
17. Smider, V., W. K. Rathmell, M. R. Lieber, and G. Chu. 1994. Restoration of x-ray resistance and V(D)J recombination in mutant cells by Ku cDNA. *Science* 266: 288-291.
18. Taccioli, G. E., T. M. Gottlieb, T. Blunt, A. Priestly, J. Demengeot, R. Mizuta, A. R. Lehmann, F. A. Alt, S. P. Jackson, and P. A. Jeggo. 1994. Ku80: product of the XRCC5 gene and its role in DNA repair and V(D)J recombination. *Science* 265: 1442-1445.
19. Nussenzweig, A., C. Chen, V. da Costa Soares, M. Sanchez, K. Sokol, M. C. Nussenzweig, and G. C. Li. 1996. Requirement for Ku80 in growth and immunoglobulin V(D)J recombination. *Nature (London)* 382: 551-555.
20. Zhu, C., M. A. Bogue, D.-S. Lim, P. Hasty, and D. B. Roth. 1996. Ku86-deficient mice exhibit severe combined immunodeficiency and defective processing of V(D)J recombination intermediates. Cell 86: 379-389.
21. Takiguchi, Y., A. Kurimasa, F. Chen, P. E. Pardington, T. Kuriyama, R. T. Okinaka, R. Moyzis, and D. J. Chen. 1996. Genomic structure and chromosomal assignment of the mouse Ku70 gene. *Genomics* 35: 129-135.
22. Kim, D., H. Ouyang, S.-H. Yang, A. Nussenzweig, P. Burgman, and G. C. Li. 1995. A constitutive heat shock element-binding factor is immunologically identical to the Ku-autoantigen. *J. Biol. Chem.* 270: 15277-15284.
23. Serrano, M., H.-W. Lee, L. Chin, C. Cordon-Cardo, D. Beach, and R. A. DePinho. 1996. Role of the INK4a in tumor suppression and cell mortality. *Cell* 85: 27-37.
24. Cordon-Cardo, C., and V. M. Richon. 1994. Expression of the retinoblastoma protein is regulated in normal human tissue. *Am. J. Pathol.* 144: 500-510.
25. Ausubel, F. M., R. Brent, R. E. Kingston, D. D. Moore, J. G. Seidman, J. A. Smith, and K. Struhl. 1997. Current Protocols in Molecular Biology. John Wiley & Sons, New York.
26. Costa, T. E. F., H. Suh, and M. Nussenzweig. 1992. Chromosomal position of rearranging gene segments influences allelic exclusion in transgenic mice. *Proc. Natl. Acad. Sci. USA* 89: 2205-2208.
27. Roth, D. B., C. Zhu, and M. Gellert. 1993. Characterization of broken DNA molecules associated with V(D)J recombination. *Proc. Natl. Acad. Sci. USA* 90: 10788-10792.
28. Bogue, M. A., C. Zhu, E. Aguilar-Cordova, L. A. Donehower, and D. B. Roth. 1996. p53 is required for both radiation-induced differentiation and rescue of V(D)J rearrangement in scid mouse thymocytes. *Gencs Dev.* 10: 553-565.

29. Van Zant, G., D. Flentje, and M. Flentje. 1983. The effect of hyperthermia on hemopoietic progenitor cells of the mouse. *Radiat. Res.* 95: 142-149.
30. Mivechi, N. F., and G. C. Li. 1985. Thermotolerance and profile of protein synthesis in murine bone marrow cells after heat shock. *Cancer Res.* 45: 3843-3849.
31. Illiakis, G., L. Metzger, N. Denko, and T. D. Stamato. 1991. Detection of DNA double-strand breaks in synchronous cultures of CHO cells by means of asymmetric field inversion gel electrophoresis. *Int. J. Radiat. Biol.* 59: 321-341.
32. Fulop, G. M., and R. A. Phillips. 1990. The scid mutation in mice causes a general defect in DNA repair. *Nature (London)* 347: 479-482.
33. Strasser, A., A. W. Harris, L. M. Corcoran, and S. Cory. 1994. Bcl-2 expression promotes B- but not T-lymphoid development in scid mice. *Nature (London)* 368: 457-460.
34. Danska, J. S., F. Pflumio, C. J. Williams, 0. Huner, J. E. Dick, and C. J. Guidos. 1994. Rescue of T cell-specific V(D)J recombination in SCID mice by DNA-damaging agents. *Science* 266: 450-455.
35. Liang, F., and M. Jasin. 1996. Ku80-deficient cells exhibit excess degradation of extrachromosomal DNA. *J. Biol. Chem.* 271: 14405-14411.
36. Chou, C. H., J.-Wang, M. W. Knuth, and W. H. Reeves. 1992. Role of a major autoepitope in forming the DNA binding site of the p70 (Ku) antigen. *J. Exp. Med.* 175: 1677-1684.

Second Series of Experiments

The data presented herein shows that evidence that inactivation of the Ku70 gene leads to a propensity for malignant transformation, both in vitro and in vivo.

Ku70−/− mouse fibroblasts displayed an increased rate of sister chromatid exchange and a high frequency of spontaneous neoplastic transformation. Ku70−/− mice, known to be defective in B- but not T-lymphocyte maturation, developed thymic and disseminated T-cell lymphomas at a mean age of 6 months, with CD4$^+$CD8$^+$ tumor cells. A plausible link between Ku70 abnormality and human lymphomas was supported by the lack of Ku70 expression in tumor specimens from thirteen out of twenty-six patients analyzed. In preliminary screens, tumor-specific mutations of Ku70 were detected in 35% (6/17) of human lymphomas and in 30% (11/38) of neuroblastomas. These findings directly demonstrate that Ku70-deficiency facilitates neoplastic growth and suggest that the Ku70 locus is a candidate tumor suppressor gene.

Recent investigations have linked the molecular mechanisms of two processes, the repair of radiation-induced DNA double-strand breaks (DSB) and V(D)J recombination during T- and B-cell development. The mammalian DNA-dependent protein kinase DNA-PK has emerged as a key molecule in these pathways. DNA-PK is a serine/threonine kinase that consists of a 465-kDa catalytic subunit (DNA-PKcs), and a DNA-targeting heterodimer consisting of a 70-kDa and an 86-kDa polypeptides (termed the Ku70 and Ku80, respectively). When assembled on double-stranded DNA in vitro, the DNA-PK holoenzyme phosphorylates transcription factors and other proteins, including Sp1, Oct1, c-fos, c-jun, p53 and the 34-kDa subunit of replication protein A (Anderson, 1993, Pan, et al., 1994). Genetic and biochemical studies strongly suggest a critical role for DNA-PK in DSB repair and V(D)J recombination (Jackson and Jeggo, 1995, Jeggo, et al., 1995, Lees-Miller, 1996). Cell lines lacking either Ku80 or DNA-PKcs are defective in both DSB repair and V(D)J recombination, and are hypersensitive to ionizing radiation (Blunt, et al., 1995, Jackson and Jeggo, 1995, Jeggo, et al., 1995, Kirchgessner, et al., 1995, Peterson, et al., 1995, Rathmell and Chu, 1994, Smider, et al., 1994, Taccioli, et al., 1994). Genes encoding each of the subunits of DNA-PK have been mapped to loci that complement the defect in x-ray-sensitive mutant cells (Jeggo, et al., 1995, Thompson and Jeggo, 1995). The gene encoding DNA-PKcs maps to human chromosome 8q11, which is also identified as the locus of the SCID gene (severe combined immune deficiency) (Blunt, et al., 1995, Kirchgessner, et al., 1995, Sipley, et al., 1995). Cells derived from SCID mice are hypersensitive to x-ray, defective in DSB repair and V(D)J recombination (Biedermann, et al., 1991), and lack DNA-PKcs expression (Blunt, et al., 1995, Kirchgessner, et al., 1995, Peterson, et al., 1995). Consistent with these findings, a radiosensitive human glioma cell line was found to be defective in DSB repair and devoid of DNA-PKcs mRNA and proteins (Lees-Miller, et al., 1995).

The Ku heterodimer was first discovered as an autoantigen in patients with autoimmune disorders (Mimori, et al., 1981). Genes encoding Ku70 and Ku80 have been cloned and cytogenetically mapped to the human chromosomes 22q13 and 2q33-35 (Cai, et al., 1994). The groups of Dynan and Jackson have provided evidence that Ku is the DNA-targeting subunit of DNA-PK (Dvir, et al., 1992, Gottlieb and Jackson, 1993). Alone, neither DNA-PKcs nor Ku has kinase activity, and DNA-PK activity requires the assembly of approximately equimolar amounts of Ku70, Ku80 and DNA-PKcs on double-stranded DNA (Chan and Lees-Miller, 1996, Suwa, et al., 1994). However, recent data reveals that DNA-PKcs can itself bind to linear DNA fragments and becomes activated for kinase activity (Hammarstein and Chu, 1998, Yaneva, et al., 1997).

Despite the rapid advances in our understanding of the genetics of the DNA-PK subunits, the precise function of each of these proteins in vivo, and their roles in DSB repair and V(D)J recombination remain unclear. Several models have been postulated (Jackson and Jeggo, 1995, Lees-Miller, 1996). After localization to a DSB, DNA-PK may signal via phosphorylation to activate enzymes or other factors involved in the rejoining of DNA ends. Alternatively, perhaps in addition to its function in signaling, DNA-PK may structurally tether adjacent DNA ends in a conformation suitable for subsequent end rejoining (Jeggo, et al., 1995, Roth, et al., 1995). Although it remains to be proven, it is very likely that the protein kinase activity of DNA-PK plays a critical role in DNA repair and recombination (Jackson and Jeggo, 1995, Lees-Miller, 1996). The in vivo function of Ku is also not well defined at the molecular level. Ku has been proposed to protect DNA ends from degradation (Liang and Jasin, 1996, Taccioli, et al., 1994), to activate DNA-PK (Dvir, et al., 1992, Gottlieb and Jackson, 1993) and to dissociate the RAG/DNA complex to facilitate DNA joining reaction (Zhu, et al., 1996). These functions are not mutually exclusive, and they all appear to depend on the interaction of Ku with DNA molecules.

To facilitate studies on the function of the Ku subunits of DNA-PK in vivo, we have recently carried out targeted disruption of Ku70 and Ku80 genes in mice (Nussenzweig, et al., 1996, Ouyang, et al., 1997). In Ku80$^{-/-}$ mice, the development of both T- and B-lymphocyte is arrested at early progenitor stages, and there is a profound deficiency in V(D)J rearrangement (Nussenzweig, et al., 1996, Zhu, et al., 1996). Similar to Ku80$^{-/-}$ phenotype, inactivation of Ku70 leads to impaired B-lymphocyte development and deficient DSB repair (Ouyang, et al., 1997). However, in contrast to the Ku80$^{-/-}$ phenotype, absence of Ku70 does not abrogate T-cell receptor (TCR) gene recombination and the development of mature T-cells (Gu, et al., 1997, Ouyanq, et al., 1997). These studies indicate that Ku70 plays an essential role in DSB repair, but is not essential for TCR V(D)J recombination, suggesting that distinct and overlapping pathways may mediate DSB repair and V(D)J recombination. A related implication of these findings is that there may be residual activity or alternate Ku70-independent pathways for V(D)J recombination during T-cell development. Hence, the processing of TCR V(D)J recombination in the Ku70–/– mouse, which is defective in DSB repair, may facilitate the generation of illegitimate recombination events (Cleary, 1991), potentially leading to tumor development.

In the present study, we examined the effect of the $Ku70^{-/-}$ defect relative to malignant transformation and tumor development in mutant mice and derived cell lines. Fibroblasts derived from $Ku70^{-/-}$ mice exhibit significantly higher frequencies of sister chromatid exchanges and spontaneous neoplastic transformation, relative to the wild type controls. Consistent with this cellular phenotype, the majority of $Ku70^{-/-}$ mice developed spontaneous thymic and disseminated T-cell lymphomas by 8 months of age. Lack of Ku70 protein expression was also found in 13 of 26 human lymphomas analyzed. Polymerase chain reaction-single strand conformation polymorphism (PCR-SSCP) analysis of genomic DNA from the human lymphoma samples and DNA sequencing confirmed the presence of Ku70 mutation. Furthermore, in our preliminary screens, tumor-specific mutations of Ku70 coding-region were detected in 35% (6/17) of human lymphomas and in 30% (11/38) of neuroblastomas. Collectively, these findings suggest that the Ku70 locus is a candidate tumor suppressor gene.

Experimental Results

Further Characterization of the Ku70–/– Mouse

We have recently reported the generation of $Ku70^{-/-}$ mice (Ouyang, et al., 1997). The Ku70 gene was inactivated by deleting 336-bp of exon 2, including the translational initiation codon of the mouse Ku70 locus. $Ku70^{+/-}$ heterozygotes exhibited no abnormalities and were used to generate a colony of $Ku70^{-/-}$ mice, used for the current experiments.

Figure 5A:
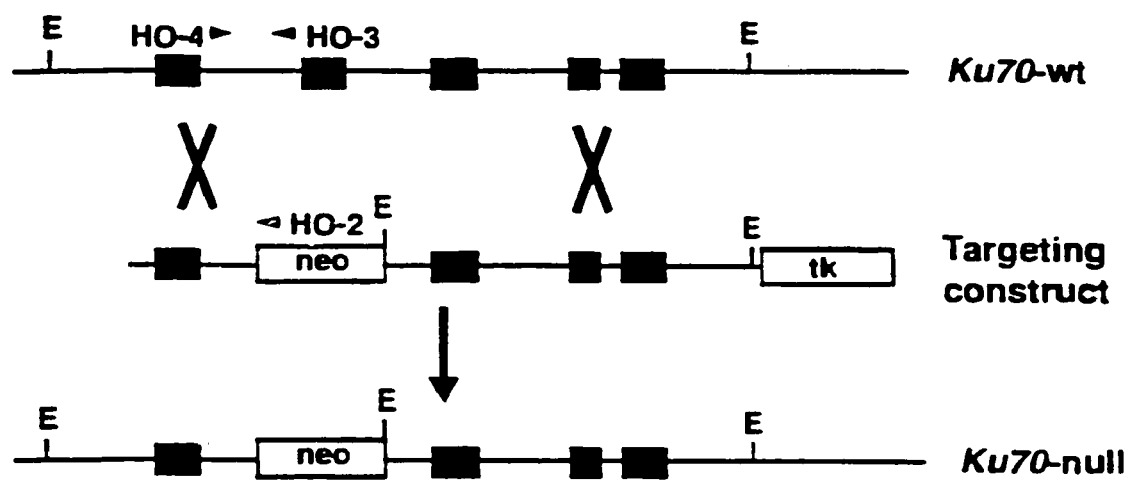
Figure 5B:
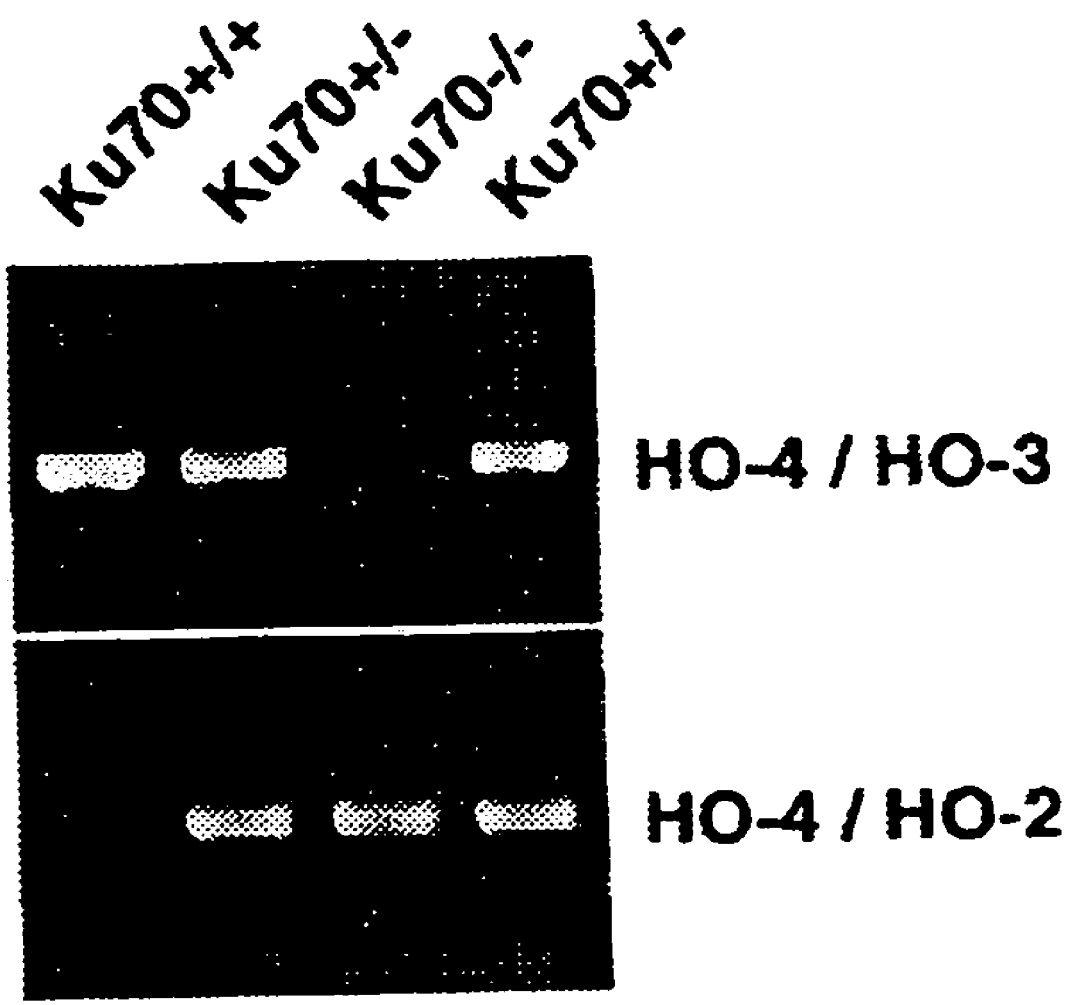
Figure 5C:
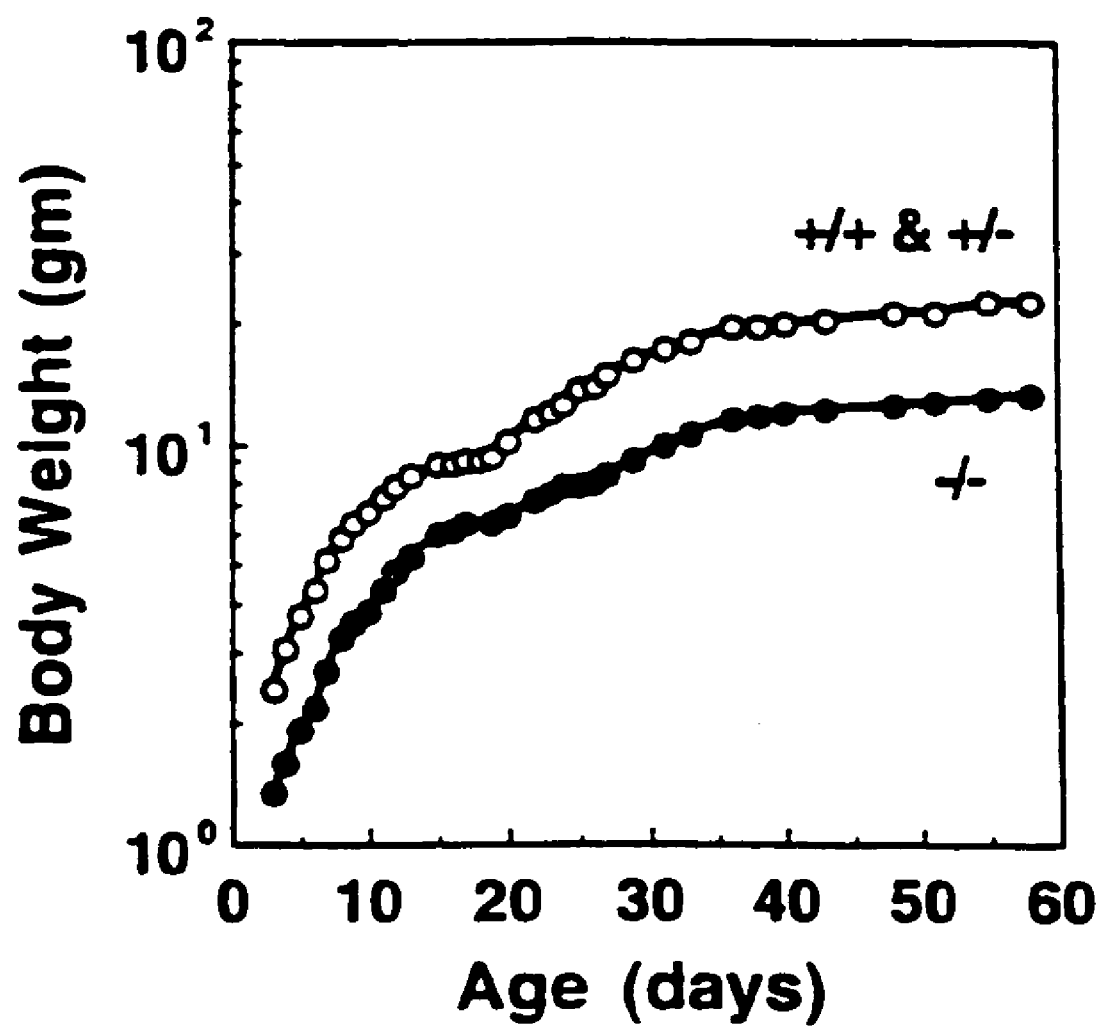
Figure 6:
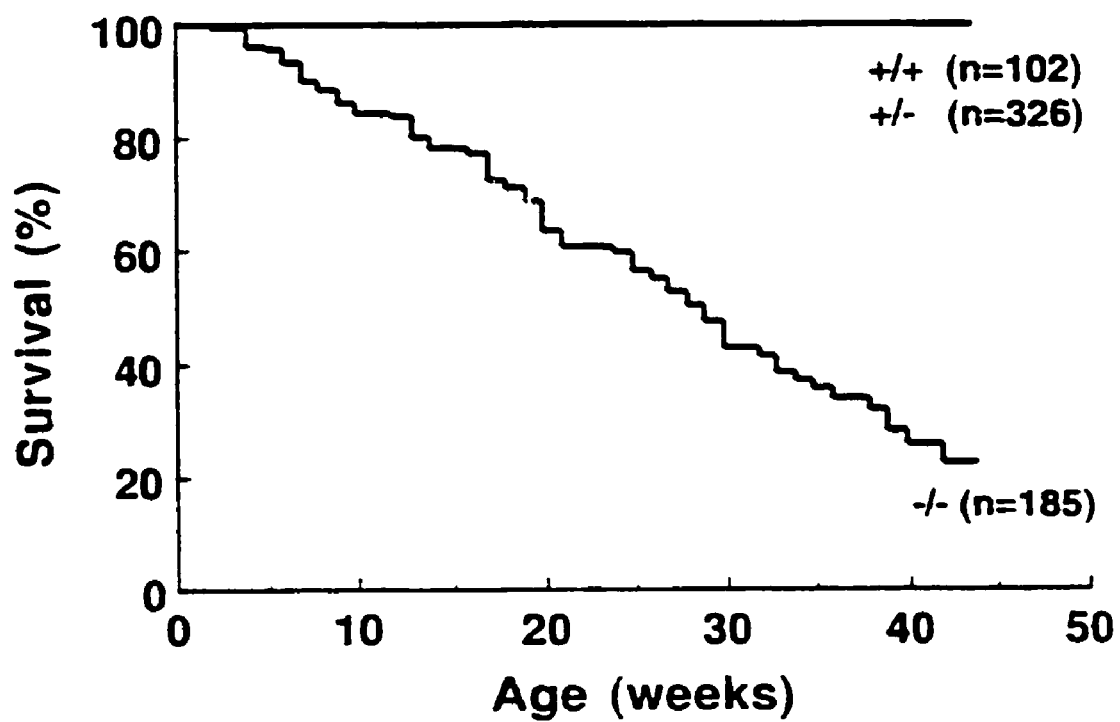

PCR analysis using specific primers confirmed that part of exon 2 was eliminated from the genome of $Ku70^{-/-}$ offsprings, and Western blot analysis with anti-Ku70 antibodies demonstrated the absence of Ku70 protein in $Ku70^{-/-}$ cells. Offsprings from $Ku70^{-/-}$ intercrosses were of all three genotypes with approximately 25% being $Ku70^{-/-}$ homozygotes, as expected from a Mendelian distribution. $Ku70^{-/-}$ mice were fertile, but 40-60% smaller than their $Ku70^{+/-}$ and $Ku70^{+/+}$ littermates (FIGS. 1A and B), a phenotype similar to $Ku80^{-/-}$ mice (Nussenzweig, et al., 1996), but distinctly different from that reported for SCID mice (Bosma, et al., 1983, Bosma and Carroll, 1991). The weight differences from the wild-type phenotype were present at birth and maintained through adulthood (FIG. 5A).

Examination of tissues from $Ku70^{-/-}$ mice revealed abnormalities in lymphatic organs and the gastrointestinal tract. Other organs, including brain, lung, liver, heart, kidney, testis and ovaries were proportionally smaller but with no apparent structural or histological abnormalities. Histological examination of the gastrointestinal tract showed mild to severe segmental aganglionosis affecting small intestine and colon (discussed in a later section). The $Ku70^{-/-}$ thymus was disproportionately smaller and contained 50- to 100-fold fewer thymoctyes than $Ku70^{+/+}$ littermates, but displayed relatively normal appearing cortical-medullary junctions as was previously reported (Ouyang, et al., 1997). The $Ku70^{-/-}$ spleen was also 5- to 10-fold smaller with the splenic white pulp significantly reduced. Immunohistochemical studies and multiparameter flow cytometric analyses revealed that there was a complete block in B-cell development at early progenitor stages. In contrast, absence of Ku70 does not block TCR gene rearrangement and the development of T-cells.

$Ku70^{-/-}$ Mice Develop T-Cell Lymphomas

Figures 2, 2B, 3, 4, 5, 6:
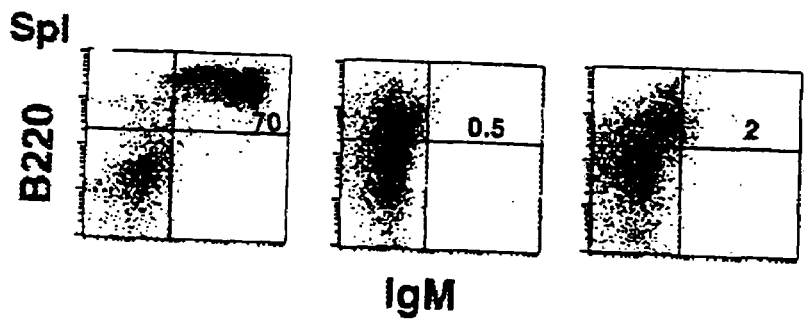

As noted previously, the processing of V(D)J recombination and proliferation of T cell precursors in $Ku70^{-/-}$ mouse, which has an intrinsic defect in DNA DSB repair, may enhance illegitimate recombination and lead to tumor development. To test this hypothesis, the tumor susceptibility of Ku70–/– mice was assessed. We randomly assigned litters arising from heterozygous intercrosses (e.g., $Ku70^{+/+}$, $Ku70^{+/-}$, $Ku70^{-/-}$) for our experiments and monitored the mice daily for tumor development and survival. As shown in FIG. 6, 100% of $Ku70^{+/+}$ (n=102) and $Ku70^{+/-}$ (n=326) littermates remained tumor-free and survived through the first 45 weeks of life. However, the actuarial survival of the Ku70/ mice at risk at 42 weeks was only 22.4%, with a median survival of 28 weeks.

Figures 2, 2B, 3, 4, 5, 6, 7, 8, 9:
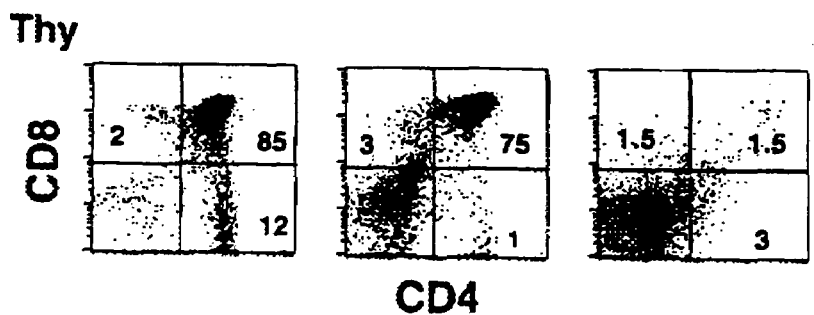

Autopsy examinations showed that, in the first 5-18 weeks of life, 14.2% of $Ku70^{-/-}$ mice died of severe forms of a Hirschprung-like syndrome (see below). Subsequently, animals died of thymic and disseminated T-cell lymphomas (FIG. 7). The youngest animal with a detectable tumor was 14 weeks old, and by 36 weeks of age, the great majority of the remaining $Ku70^{-/-}$ mice died of T-cell lymphoma. Tumors of B lymphoid or non-lymphoid origin were not detected among the 45 tumor-bearing animals examined. In contrast, for the same observation period, no tumors were detected in colonies of $Ku80^{-/-}$ and SCID micE. Histologically, the primary tumors consisted of mononuclear, atypical cells with cleaved nuclei, prominent nucleoli, and many mitotic figures. Immunohistochemical analyses revealed that the tumor cells were CD3+, confirming the diagnosis of T-cell lymphoma (FIG. 7, D, E, and F). In most cases, these tumors involved other organs, such as the lung, heart, kidney, spleen and liver; a CD3+ phenotype was identified in all of these tumors.

Figure 7C:
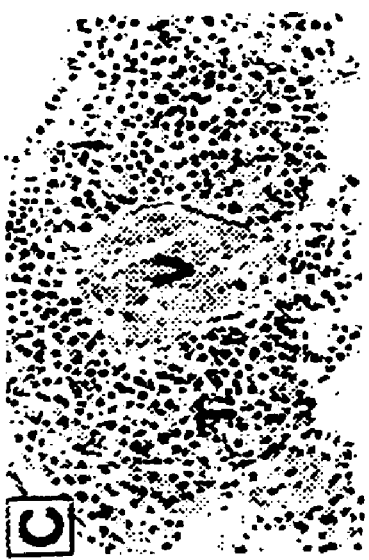
Figure 7B:
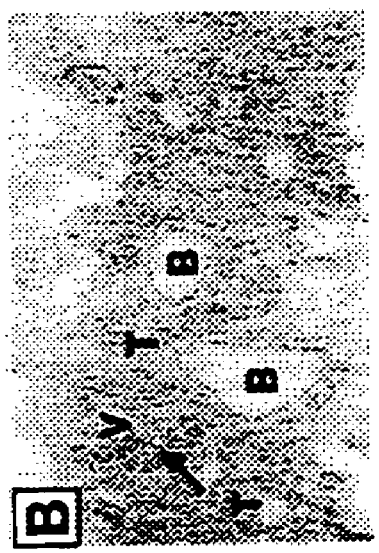
Figure 7A:
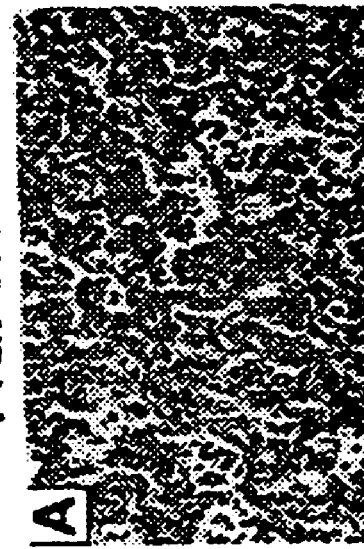
Figure 7F:
Figure 7E:
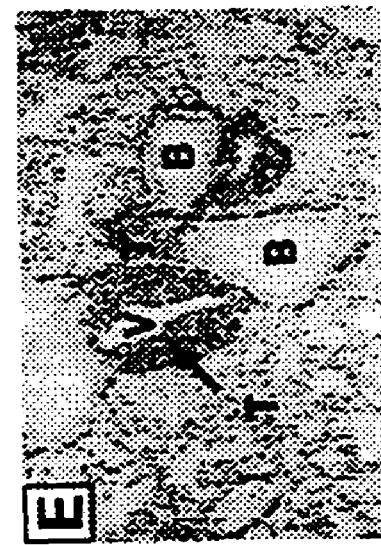
Figure 7D:
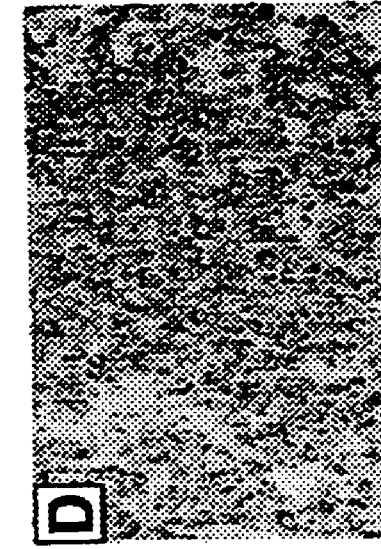
Figures 1, 7G:
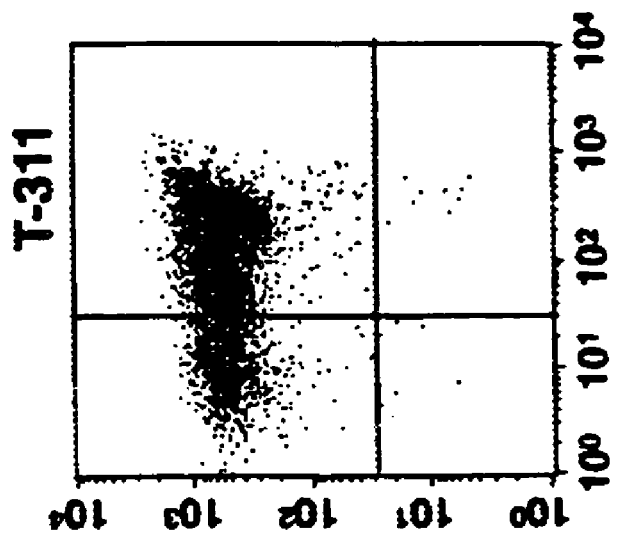
Figures 2, 7G:
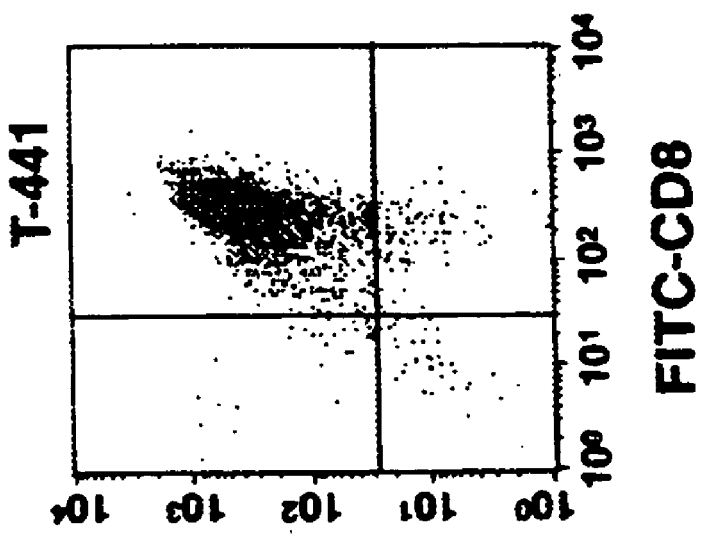
Figures 3, 7G:
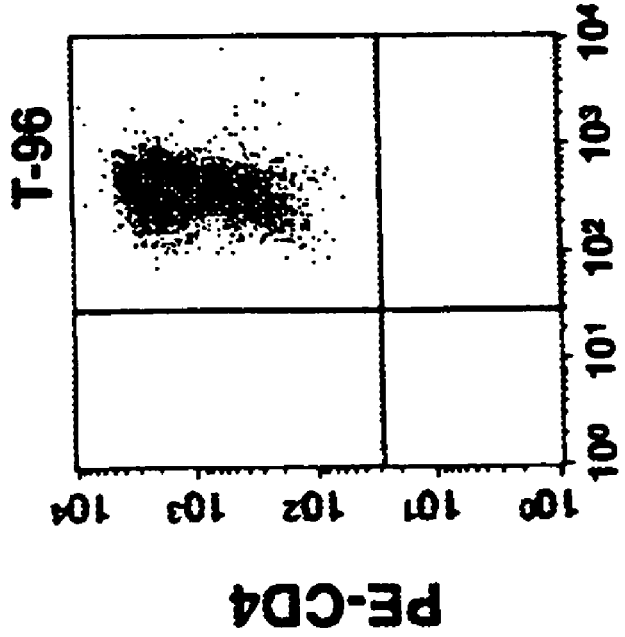

Cell lines were readily established from five thymic tumors, designated T-96, T-49, T-248, T-311, and T-441. These tumor cell lines had a doubling time of 16-18 hr. Flow cytometric analysis of three of these tumor lines at early passages revealed a CD4$^+$CD8+ DP phenotype (FIG. 7G), consistent with immature T cells of thymic origin.

In addition, Southern analysis of cells from these $Ku70^{-/-}$ thymic lymphomas, using a TCR Cβ cDNA probe (Danska, et al., 1994), exhibited only one or two TCRβ rearrangement per tumor, suggesting that the tumors are of clonally derived nature. Karyotyping analyses on cultured cells derived from three primary T-cell lymphomas developed in Ku70-deficient mice revealed multiple chromosomal abnormalities. All three cultured tumor cells showed monosomy of chromosome 8. Two of the three cultured tumor cells displayed trisomy of chromosomes 1 and 13, as well as monosomy of chromosome 12. Other alterations identified included monosomy affecting chromosomes 9, 10, and 16; trisomy of chromosomes 4, 5, 6, and 15; and duplication of chromosome 6, 14, and 15. It is, thus, reasonable to postulate that some DP $Ku70^{-/-}$ cells acquired mutations that enhanced their survival or the ability to proliferate relative to that of short-lived wild type DP thymocytes.

Ku70$^{-/-}$ Fibroblasts also Undergo Malignant Transformation

Spontaneous neoplastic transformation occurs rarely in primary mouse fibroblasts. Consistent with this observation, primary mouse ear fibroblasts (MEFs), derived from Ku70$^{+/+}$ or Ku70$^{+/-}$ and cultured up to passage 10, did not undergo spontaneous malignant transformation. In contrast, the formation of type III transformed foci was observed in Ku70$^{+/+}$ MEFs at a transformation frequency of 4.3×10$^{-2}$/viable cell (FIG. 8, A and B). Co-transfection with HPV16 E6 and E7 into Ku70$^{-/-}$ MEFs further increased the frequency of foci formation, whereas transformation was not observed in E6/E7 co-transfected Ku70$^{+/+}$ or Ku70$^{-/-}$ fibroblasts.

Analysis of chromosomal aberrations in the various cell cultures grown at 37° C. revealed that the Ku70$^{-/-}$ cells contained 0.326 sister chromatid exchanges (SCE) per chromosome (n=30 cells), representing a 2.2-fold increase over that of Ku70$^{+/-}$ cells (0.147 SCE per chromosome, n=34 cells) (p<0.05). Similarly, the E6/E7 co-transfected Ku70$^{-/-}$ cells contained a nearly 3-fold higher frequency of SCE (0.262 SCE per chromosome, n=36 cells) than the E6/E7 co-transfected Ku70$^{+/+}$ or wild type Ku70$^{+/+}$ cells (0.092 SCE per chromosome, n=23 cells) (p<0.05).

Figure 8A:
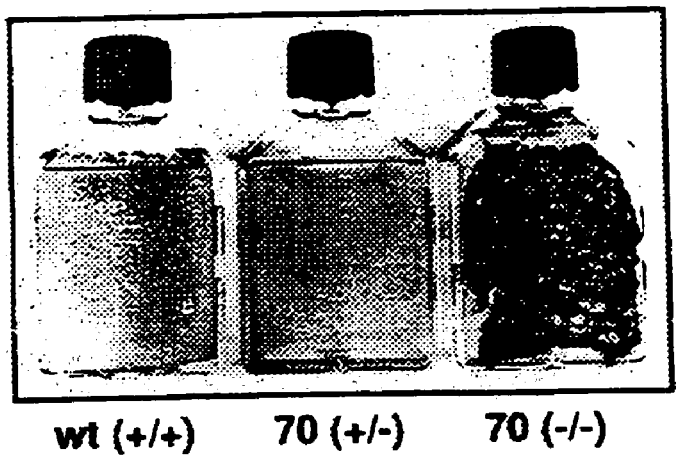
Figure 8B:
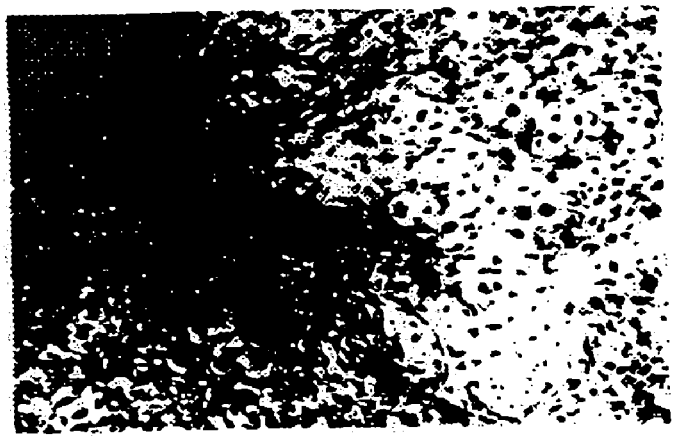
Figure 8C:
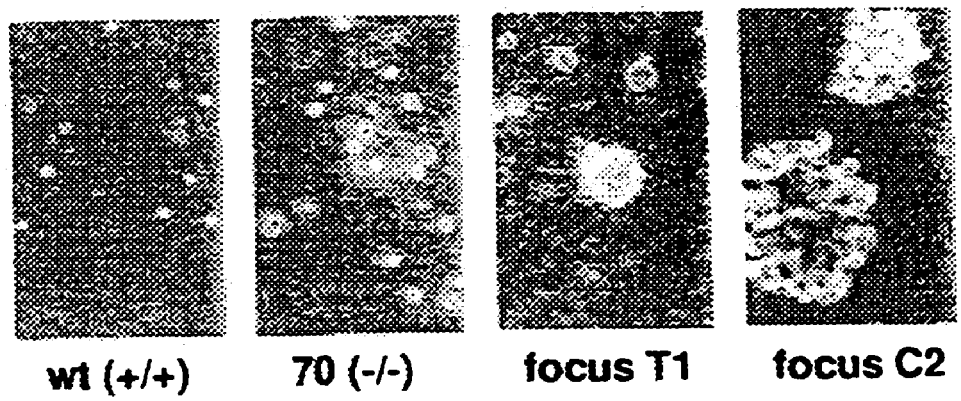
Figure 10A:
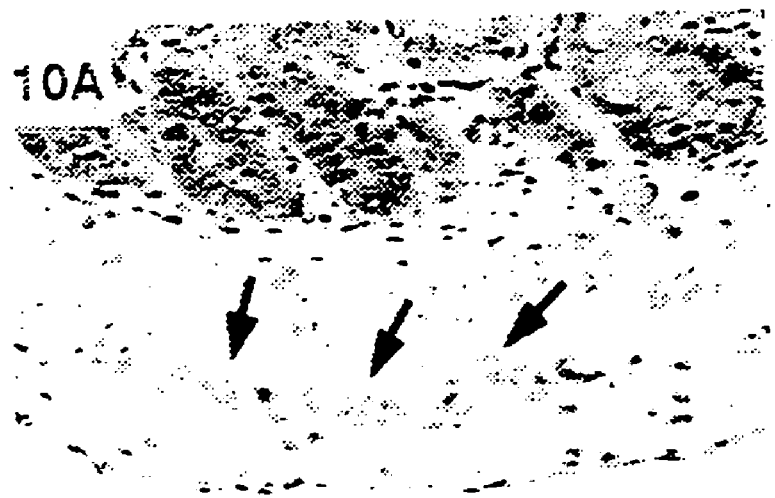
Figure 10B:
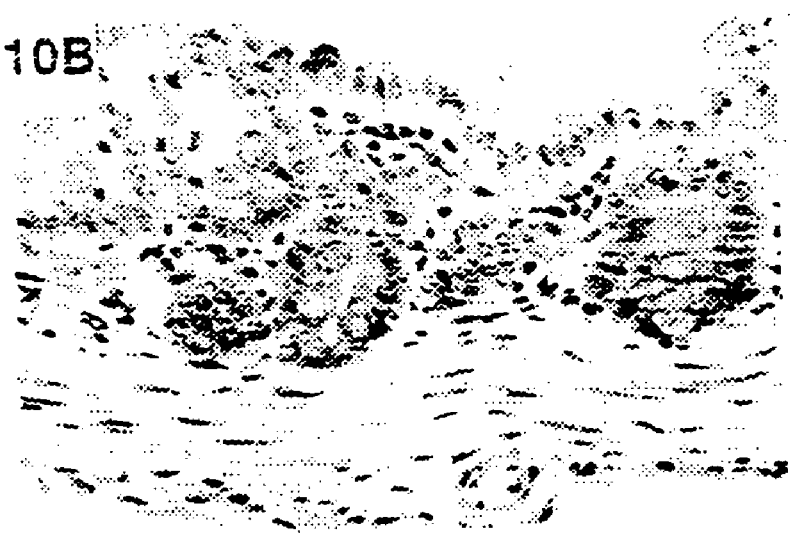
Figure 10C:

The foci derived from the primary and from the E6/E7 co-transfected Ku70$^{-/-}$ cultures were further tested for their ability to grow under anchorage-independent conditions and to produce tumors in nude mice. FIG. 8C shows that Ku70$^{-/-}$ cells derived from the transformed foci readily produced colonies in soft agar, while no anchorage-independent growth was evident for the Ku70$^{+/+}$ +cells. For tumor formation in nude mice (Jackson Laboratory), 5×10$^6$ Ku70$^{-/-}$ cells derived from transformed foci or Ku70$^{+/+}$ fibroblasts were injected into each of the two flanks of two nude mice and tumor formation was scored after 3 weeks. We found that Ku70$^{-/-}$ cells derived from the transformed foci produced tumors in nude mice (100% tumor take), while no tumor was evident for Ku70$^{-/-}$ cells. Taken together, these results indicate that Ku70-deficiency leads to an increased propensity for malignant transformation on of primary mouse fibroblasts.

Extreme Radiation Sensitivity of Ku70$^{-/-}$ Mice and Ku70$^{-/-}$ Fibroblasts

Previous studies have shown that Ku70$^{-/-}$ primary fibroblasts were impaired in the repair of radiation-induced DSB (Ouyang, et al., 1997). To demonstrate that this deficiency in DSB repair leads to the hypersensitivity of Ku70$^{-/-}$ cells to radiation, monolayers of Ku70–/– and Ku70$^{-/-}$ primary ear fibroblasts (passage 7) were exposed to graded doses of g-irradiation (0-6 Gy), and survival was determined by a colony formation assay. FIG. 9A clearly shows that Ku70$^{-/-}$ cells were much more radiosensitive than the wild type controls, with a >100-fold difference in survival after 400 cGy of γ-irradiation.

To assess the radiation-sensitive phenotype in vivo, adult (4 months old) Ku70–/– mice were given 400 cGy of γ-irradiation as were the wild type controls (FIG. 9B). All wild type mice survived. However, all irradiated Ku70–/– mice died within two weeks.

Gastrointestinal Abnormalities in Ku70$^{-/-}$ Mice

Figures 2, 2B, 3, 4, 5, 6, 7, 8, 9, 10, 11, 12:
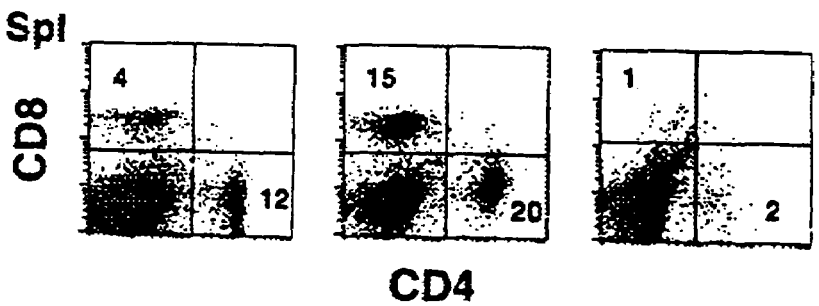

In our experimental group of Ku70$^{-/-}$ mice, we observed that 14.2% died without evidence of lymphoma. Histological examination showed that all these mice, as well as 60% of the lymphoma-bearing Ku70$^{-/-}$ mice, showed unique gastrointestinal abnormalities. Mild to severe segmental aganglionosis was observed, affecting the small intestine and the colon (FIG. 10). These abnormalities were further confirmed by immunohistochemical assays: the number of ganglion cells identified by chromogranin immunostaining was very much reduced or absent in segments of the intestinal tract of the Ku70$^{-/-}$ mice. This phenotype was associated with the effacement of the typical morphology of the intestinal villi, dilatation of intestinal lumens and denudation of the intestinal mucosa, causing functional obstruction and progressive distention of the intestine. In some cases, we observed this alteration even in the esophagus and stomach. These changes were similar to those described in Hirschsprung disease (Badner, et al., 1990). Death caused by the more severe form of this phenotype began around 5 weeks of age and peaked around 12 weeks, much earlier than the onset of lymphoma death at 14 weeks. These abnormalities were not observed in heterozygous and wild type mice up to 8 months of age.

Ku70 Alterations in Human Tumors

Because of the high incidence of T-cell lymphomas in Ku70$^{-/-}$ mice, we evaluate the possibility that abnormal Ku70 expression also occurs in human lymphomas. Tumor samples from fourteen patients with T-cell lymphomas and twelve patients with B-cell lymphomas, classified by a panel of antibodies to specific cell surface markers and molecular probes, were analyzed. Immunohistochemical analysis, using a purified rabbit antiserum specific to Ku70 (Ouyang, et al., 1997), showed an intense nuclear staining pattern of Ku70 protein in human normal lymphocytes of the spleen (FIG. 11G) and of the lymph nodes. Patterns of Ku70 staining was not affected by the method of tissue preparation and were similar in frozen sections and paraffin-embedded samples, with intense nuclear staining on lymphocytes and endothelial cells in both sample types (FIGS. 11C and 11G).

Figure 11A:
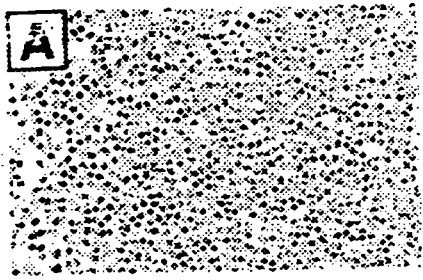
Figure 11B:
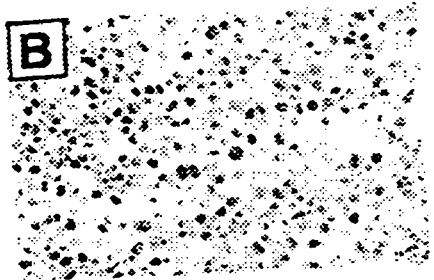
Figure 11C:
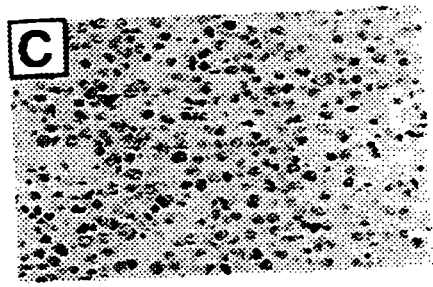
Figure 11D:
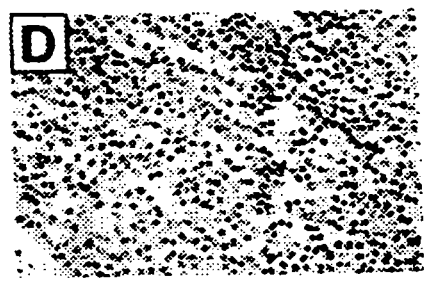
Figure 11E:
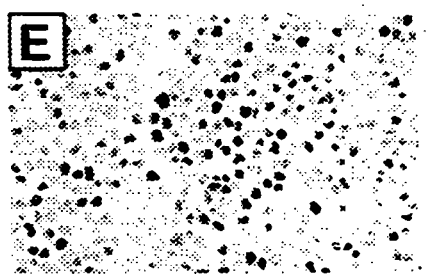
Figure 11F:
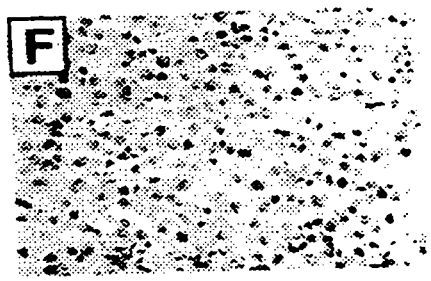
Figure 11G:

However, seven of the fourteen T-cell lymphomas analyzed showed undetectable Ku70 levels in the nuclei (FIGS. 11B and 11C), while the remaining seven cases displayed weak to moderate heterogeneous nuclear immunoreactivities (FIG. 11A). In addition, four of these cases showed an abnormal cytoplasmic Ku70 expression. In the Ku70-negative cases, inflammatory cellular infiltrates, as well as endothelial cells, were found to have a strong nuclear staining, serving as internal positive controls (see FIG. 1C). Similarly, six of the twelve B-cell lymphomas showed undetectable Ku70 staining in the nuclei of tumor cells (FIGS. 11E and 11F). We also observed an abnormal cytoplasmic expression of Ku70 in nine of these twelve B-cell lymphomas (FIG. 11F). Thus, most of the human lymphomas studied showed Ku70 alterations, either lacking completely Ku70 expression, or displaying abnormal Ku70 cytoplasmic localization.

Figures 1, 11H:
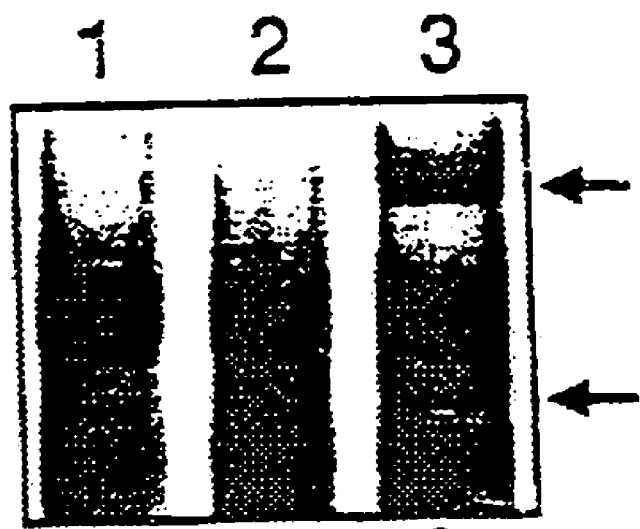
Figures 2, 11H:
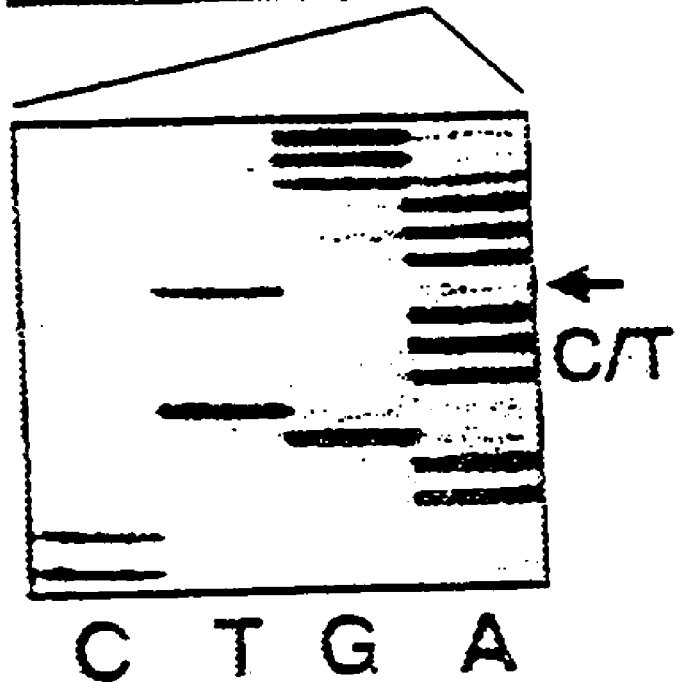

To complement the immunohistochemical data and to further explore the significance of these findings, we carried out PCR-SSCP analysis with 17 of the 26 primary human lymphomas from which frozen tissues were available (7 T-cell and 10 B-cell lymphomas). Search for mutations was first conducted at the genomic level, i.e. using genomic DNA as the substrate. Because the boundaries between the introns and the 13 exons of the human Ku70 gene are not well established, we were limited by the use of nine pairs of primers (for nine of the 13 exons) to amplify about 50% of the coding region of the human Ku70 gene. SSCP analysis of the PCR products (74 to 194 bp in size) exhibited bandshifts in 3 out of the 17 lymphoma samples. Sequence analysis of one case revealed a point mutation of ACA to ATA at codon 292, converting a threonine to isoleucine (FIG. 11H). Mutation could not be confirmed, however, for the other two cases, probably due to the suboptimal conditions of the primers used.

For further corroboration, we characterized the coding sequences of Ku70 in the 17 above referred lymphomas. We also expanded the study to include a panel of 38 well characterized neuroblastomas. Direct PCR-sequencing was performed from the cDNA products of these samples. Using this strategy, the whole coding region of Ku70 was examined. We found that Ku70 sequences were frequently mutated in the tumor samples, but not in their corresponding normal tissues (for examples see FIGS. 11I and 11J). More specifically, 2 out of 7 T-cell lymphomas and 4 out of 10 B-cell lymphomas showed multiple point mutations at codons 292, 344, 452, 453, 460, and 466, with a predicted effect of amino acid substitution from threonine to isoleucine glycine to alanine, isoleucine to valine, methionine to threonine, glycine to aspartic acid, and valine to isoleucine, respectively (FIG. 11I and Table II). In addition, tumor-specific point mutations were identified in 11 of 38 neuroblastomas at codons 529 (silent), 530 (Tyr→His), 549 (Gly→Asp), and 593 (silent) (FIG. 11J and Table II). Representative Ku70 mutations identified in human primary tumors are summarized in Table II and illustrated in FIG. 11.

TABLE II

Representativ Ku70 Mutations Identified in Human Primary Tumors

| Codon | Mutation | Predicted Effect |
|---|---|---|
| T- and B-cell lymphomas | | |
| 344 | GGT→GCT | Gly→Ala |
| 292 | ACA→ATA | Thr→Ile |
| 452 | ATC→GTC | Ile→Val |
| 453 | ATG→ACG | Met→Thr |
| 466 | GTT→ATT | Val→Ile |
| 460 | GGC→GAC | Gly→Asp |
| Neuroblastomas | | |
| 529 | GTT→GTC | silent |
| 530 | TAC→CAC | Tyr→His |
| 549 | GGT→GAT | Gly→Asp |
| 593 | GGT→GGG | silent |

Experimental Discussion

The present study reveals a novel characteristic of the Ku70$^{-/-}$ phenotype, the propensity for malignant transformation, both in vitro and in vivo. In vitro, this is expressed in terms of increased rate of sister chromatid exchange, frequent spontaneous neoplastic transformation of primary fibroblasts, anchorage-independent growth of the transformed foci in soft agar and their ability to produce tumors in nude mice. In vivo, Ku70$^{-/-}$ mice spontaneously develop thymic and disseminated T-cell lymphomas. Concordant with these data, tumor specimens from human T-cell lymphomas also showed a pathological lack of Ku70 protein expression and the presence of tumor-specific mutations. These findings directly demonstrate that inactivation of the Ku70 gene facilitates neoplastic growth, and strongly suggest the Ku70 locus as a candidate tumor suppressor gene for murine and human T-cell lymphoma.

The specificity of the murine Ku70$^{-/-}$ phenotype for the development of T-cell but not B-cell lymphoma is consistent with our recent observation that the development of B-lymphocytes was absent in Ku70$^{-/-}$ mice (Ouyang, et al., 1997). In contrast to SCID and Ku80$^{-/-}$ mice, in which both T- and B-lymphocyte development is arrested at early progenitor stages (Bosma and Carroll, 1991, Carroll and Bosma, 1991, Carroll, et al., 1989, Lieber, et al., 1988, Nussenzweig, et al., 1996, Zhu, et al., 1996), the absence of Ku70 blocks neither TCR gene rearrangement nor the development of mature T cells (Gu, et al., 1997, Ouyang, et al., 1997). Nonetheless, the T-cell specific differentiation was suboptimal in Ku70$^{-/-}$ mice, with a 50- to 100-fold fewer thymocytes compared to the wild type littermates. These results suggest that there may be a residual activity, or an alternate Ku70-independent pathway for TCR V(D)J recombination and maturation of T-cells. However, this pathway may be less efficient, or does not provide all the necessary signals to fully effect the developmental transition. Another possible explanation for the lack of expansion of Ku70$^{-/-}$ DP thymocytes may be associated with the intrinsic propensity of DP cells to undergo apoptosis (Smith, et al., 1989), which may be further enhanced by the absence of Ku70. Consistent with this paradigm, we found that SV40-transfected Ku70$^{-/-}$ cells were extremely susceptible to radiation-induced apoptosis relative to wild type controls. Differences in genetic background are unlikely to contribute to the different phenotypes of Ku70$^{-/-}$ and Ku80$^{-/-}$ mice in the development of tumors. Both of our Ku70$^{-/-}$ and Ku80$^{-/-}$ mice were generated in the transgenic mouse core facility at Memorial Sloan-Kettering Cancer Center using identical protocols, including the same strain of ES cells and the same C57BL/6 mice (Nussenzweig, et al., 1996, Ouyang, et al., 1997). Thus, the Ku70$^{-/-}$ strain used was in a mixed 129/SV×C57BL/6 background like that of our Ku80$^{-/-}$ strain. Furthermore, an independently derived line of Ku70$^{-/-}$ ice had a phenotype essentially identical to that which we describe (Gu, et al., 1997).

The mechanism for the induction of thymic lymphoma in Ku70$^{-/-}$ mice is not clear at present. It is reasonable to hypothesize that a thymocyte maturation defect and thymic malignancies are mechanistically related, and associated with abnormalities in DNA DSB repair, a characteristic of the Ku70$^{-/-}$ cells. Although residual DSB rejoining may be responsible for the apparent TCR V(D)J recombination, alternative DNA repair pathways may exist in the absence of Ku70. Such pathways may functionally complement the Ku70 gene and participate in TCR gene rearrangement. On the other hand, the rescue of TCR gene rearrangement and T-cell proliferation in a global DNA repair-deficient environment may enhance the generation of illegitimate recombination (Cleary, 1991), leading to the development of T-cell malignancies. Consistent with this model is our current observation on the increased frequency of neoplastic transformation in Ku70$^{-/-}$ fibroblasts, suggesting that loss of Ku70 may constitute one critical event in the multistep transformation processes.

The hypothesized link between deficient DSB repair, defective T-cell differentiation and tumor development in Ku70$^{-/-}$ mice is consistent with the experimental results obtained in irradiated SCID mice (Danska, et al., 1994). While SCID cells were shown to be deficient in the repair of radiation-induced DSB and V(D)J recombination (Bosma and Carroll, 1991, Carroll and Bosma, 1991, Carroll, et al., 1989, Lieber, et al., 1988), treatment of newborn SCID mice with a sublethal radiation dose of 100 cGy restored normal T-cell receptor TCRb recombination, T-cell maturation and thymocyte proliferation, but not IgM rearrangement or B-cell development (Danska, et al., 1994). Relevant to this study is the observation that all of the irradiated SCID mice eventually developed T-cell tumors, but not tumors of B-lymphoid or non-lymphoid origin. These data support the notion that the induction of alternative pathways for DSB rejoining, apparently activated by radiation, can restore TCR V(D)J recombination; but because of their deficiency in DSB repair, these activities promote the malignant transformation of T-cells. Therefore, the T-lineage specificity of neoplastic transformation, either induced by low-dose irradiation (as in the case of SCID mice) or occurring spontaneously (as in Ku70$^{-/-}$ mice), may reflect an interaction between defective DNA DSB repair and TCR gene rearrangement.

Although Ku70$^{-/-}$ cells of non-lymphoid lineage, such as primary fibroblasts, can undergo spontaneous transformation in vitro, we observed no spontaneous tumors other than T-cell lymphomas in the Ku70$^{-/-}$ mice. This may be due to the fact that nearly all animals observed up to the age of 8 months died of either T-cell lymphoma or a Hirschsprung like gastrointestinal syndrome. Mild to severe segmental aganglionosis in the gastrointestinal tract was, in fact, detected in the great majority of Ku70$^{-/-}$ mice examined by autopsy. This unexpected phenotype was associated with the effacement of the typical morphology of the intestinal villi, dilatation of the intestinal lumens and denudation of the intestinal mucosa, disorders similar to those described in the Hirschsprung disease (HSCR). Human HSCR is a congenital disorder of the enteric nervous system characterized by the absence of enteric ganglia (Badner, et al., 1990, Pingault, et al., 1997). Three genes for HSCR have been identified, including the RET protooncogene (Angrist, et al., 1995, Attie, et al., 1995), the gene encoding the endothelin B receptor (EDNRB) (Amiel, et al., 1996), and the endothelin 3 gene (EDN3) (Edery, et al., 1996, Hofstra, et al., 1996). In mice, spontaneous and in vitro-induced mutations affecting the RET, EDNRB, and EDN3 genes generate phenotypes similar to human HSCR. Another murine model of HSCR-disease is the Dominant megacolon (Dom), a spontaneous mouse mutation in which the target gene has not yet been fully characterized (Pavan, et al., 1995, Pingault, et al., 1997, Southard-Smith, et al., 1998). Interestingly, the Dom mutation has been mapped to the middle-terminal region of mouse chromosome 15. Using known polymorphisms for conserved human/mouse genes, the homology between the Dom locus and human chromosome 22q12-q13 has been established (Pingault, et al., 1997). Although the mouse Ku70 locus is also mapped to chromosome 15 (Takiguchi, et al., 1996), it is unlikely that the Dom gene is disrupted in the Ku70$^{-/-}$ mice, because of the fact that the homozygous Dom mutation results in a lethal phenotype. However, it would be of great interest to examine whether the expression of Dom gene, or that of the other HSCR genes, are affected by the absence of Ku70 protein.

The spontaneous development of T-cell tumors in the Ku70$^{-/-}$ mice is very different from the Ku80$^{-/-}$ and SCID phenotypes. It is, however, comparable with the development of thymic lymphoblastic lymphomas in Atm-deficient mice (Barlow, et al., 1996) and DNA-PKcs null mice (Jhappan, et al., 1997), the development of thymic tumors in p53-deficient mice (Donehower, et al., 1992, Jacks, et al., 1994, Purdie, et al., 1994, Tsukada, et al., 1993) and the predisposition to lymphoreticular malignancies in ataxia telangiectasia patients (Boder, 1975, Sedgewick and Boder, 1991). However, AT and p53 mutations are associated with other tumor types as well (Donehower, et al., 1992, Jacks, et al., 1994). Thus, the dominance of T-cell tumors in Ku70$^{-/-}$ mice is unique. Our analysis of human tumor samples, however, suggests a possible association of Ku70 with both T- and B-cell lymphomas (FIG. 11).

The expression and molecular genetic analyses of Ku70 conducted in human lymphomas and neuroblastomas support the postulate of a role for Ku70 in tumor suppression. Tumor-specific mutations were first pursues and identified in T-cell lymphomas. However, we expanded the mutational screening to B-cell lymphomas and neuroblastomas, as these tumors are two of the most frequent malignancies affecting the pediatric population. Normal B-lymphocytes and neurons express high nuclear levels of Ku70 protein, similar to those observed in normal T-lymphocytes. The altered pattern of Ku70 expression, mainly the lack of Ku70 nuclear staining and the ectopic cytoplasmic localization of Ku70 protein in a large fraction of tumors studied, suggest potential genetic aberrations. The identification of multiple tumor-specific mutations in a subset of the lymphomas and neuroblastomas screened is consistent with our working hypothesis. Whether mutations represent the basis for lack of or aberrant expression of Ku70 in all of the human tumor specimens examined remains to be further analyzed. There are, however, other mechanisms to inactivate tumor suppressors. Methylation of the promoter region of certain genes, such as the p16/INK4A, produces silencing of transcription and absence of the final gene product (Gonzalez-Zulueta, et al., 1995, Merlo, et al., 1995). Inhibition of tumor suppression function can also be achieved by viral and cellular proteins shown to interact with specific suppressor products, such as p53 and RB (Dyson, et al., 1989, Linzer and Levine, 1979, Sarnow, et al., 1982, Werness, et al., 1990, Whyte, et al., 1988). More recently, it has been demonstrated that p27 is degraded via proteasome-mediated mechanisms rather than tumor-specific mutations (Ponce-Castaneda, et al., 1995), and that p27 -deficiency is associated with tumorigenesis and tumor progression in certain human neoplasms (Loda, et al., 1997, Porter, et al., 1997). The mutations identified in the Ku70 gene, together with the abnormal patterns of expression observed in the majority of human lymphoma samples, are in accordance with the hypothesis that Ku70 has an important role in tumor suppression.

In summary, our studies show that inactivation of Ku70 results in a distinct phenotype, relative to Ku80$^{-/-}$ and SCID mice, which are deficient in the other components of the DNA-PK complex. Consistent with the observation that the Ku70$^{-/-}$ mouse is highly susceptible to the development of spontaneous thymic and disseminated T-cell lymphoma, human T-cell lymphomas examined also showed altered Ku70 expression and tumor-specific Ku70 mutations. These data demonstrate that the disruption of Ku70 facilitates neoplastic growth and strongly suggest that the Ku70 locus is a candidate tumor suppressor gene. Although the Ku70$^{-/-}$ rodent model did not exhibit other tumor types, the high frequency of sister chromatid exchanges in Ku70$^{-/-}$ fibroblasts and their high susceptibility to spontaneous neoplastic transformation raises the possibility that other human tumors may also be affected by the function of the Ku70 locus. This is further supported by the abnormal expression pattern of Ku70 in B-cell lymphomas, as well as the multiple tumor-specific Ku70 mutations detected in B-cell lymphomas and neuroblastomas.

Experimental Procedures

Target Disruption of Ku70 and Generation of Ku70$^{-/-}$ Mice

Mouse genomic Ku70 gene was isolated from a sCos-I cosmid library constructed from a mouse strain 129 embryonic stem cell line (Takiguchi, et al., 1996). The replacement vector was constructed using a 1.5 kb 5'-fragment which contains the promoter locus with four GC-box and exon 1, and a 8 kb EcoRV-EcoRI fragment extending from intron 2 to intron 5 (Ouyang, et al., 1997). Homologous replacement results in a deletion of 336-bp of exon 2 including the translational initiation codon.

The targeting vector was linearized with Not 1 and transfected into CJ7 embryonic stem (ES) cells by electroporation using a Bio-Rad Gene Pulser. Three hundred ES cell clones were screened, and 5 clones carrying the mutation in Ku70 were identified by Southern blotting. Positive ES clones were injected separately into C57BL/6 blastocysts to generate chimeric mice. One clone was successfully transmitted through the germline after chimeras were crossed with C57 BL/6 females. Homozygous Ku70$^{-/-}$ mice were generated by intercrossing Ku70$^{+/-}$ heterozygotes.

The genotypes of the mice were first determined by tail PCR analysis which distinguishes endogenous from the targeted Ku70 allele, and subsequently confirmed by Southern blot analysis. The PCR reaction contained 1 mg genomic DNA; 0.6 mM (each) of primers HO-2: GGGCCAGCTCAT-TCCTCCACTCATG (SEQ ID NO: 40), HO-3: CCTACAGT-GTACCCGGACCTATGCC (SEQ ID NO: 25) and HO-4: CGGAACAGGACTGGTGGTTGAGCC (SEQ ID NO: 41); 0.2 mM (each) dNTP; 1.5 mM MgCl$_2$ and 2.5 U of Taq polymerase. Cycling conditions were 94° C. for 1 min, 64° C. for 1 min, 72° C. for 1 min (30 cycles), followed by an extension at 72° C. for 10 min. Primers HO-2 and HO-4 give a product of the targeted allele that is −380 bp; primers HO-3 and HO-4 yield a wild type product of 407 bp.

Cell Cultures and Determination of Radiosensitivity

Monolayers of cells (1-2×10$^5$ cells) were seeded in 60 mm petri dishes and cultured at 37° C. for 3 days at which time they were near confluence (1-2×10$^6$ cells per dish). The culture medium was then changed daily, and the cells were at a density-inhibited plateau phase by day 6. The pulse-labeling index, as determined by incubation for 30 min with 10 mCi/ml of $^3$H-thymidine and autoradiographic analysis, was <1% indicating a paucity of cycling cells. Experiments were performed on day 6 or 7.

Survival curves were obtained by measuring the colony-forming ability of irradiated cells as described previously (Nagasawa, et al., 1991). A colony containing more than 50 cells was scored as a survivor. Cell survival was always normalized to the cloning efficiency of untreated controls. All experiments were performed at least three times and yielded consistent results.

Spontaneous Transformation of Ku70-Deficient Cells

To study the spontaneous transformation of Ku70-deficient fibroblasts, the well established protocols of Little were used (Little, 1979). Cells were seeded into 6 replicate 100-mm plastic Falcon petri dishes, at densities designed to yield approximately 4000 to 7000 viable (colony forming) cells per dish. After a 0.3- to 4-week incubation at 37° C., with twice weekly renewal of the nutrient medium, the cultures were fixed with 95% ethanol and stained with 0.1% crystal violet. Transformed foci (Type III) appeared as dense piled-up colonies of cells overlying the normal monolayer. Cells from these foci were isolated, expanded and further tested for their ability to grow in soft agar in an anchorage-independent manner.

In parallel with the above, three 100 mm dishes were seeded from a 1:50 dilution of the same cell suspension (80 to 140 viable cells) in each group in order to determine the actual colony forming efficiency. After a 10- to 12-day incubation at 37° C., the samples were fixed and stained, the number of viable colonies counted, and the cloning efficiency determined, which was then used to calculate the number of viable cells seeded in the transformation dishes. The transformation frequency was determined by dividing the total number of transformed foci scored in a treatment group by the total number of viable cells seeded, and it was therefore expressed as transformants per viable cell.

For colony formation in soft agar, a modified MacPherson method (MacPherson, 1973) was used (Nagasawa, et al., 1987). Plastic petri dishes (60 mm) were coated with a layer of 5 ml of 0.5% agarose in medium supplemented with 20% heat-inactivated fetal bovine serum. Two milliliters of the cell suspension were mixed with 4 ml of the 0.5% agarose solution; 1.5 ml of the resulting cell suspension were plated into the agarose-coated dishes. Subsequently, the cultures were fed once a week by adding 1 ml of complete medium (without agarose). The size of the colonies was monitored at 2 days, 1, 2, and 3 weeks after seeding by taking photomicrographs of the cultures on an inverted microscope. For tumor formation in nude mice (Jackson Laboratory), 5×10$^6$ cells were injected into each of the two flanks of two nude mice and tumor formation was scored after 3 weeks.

Analysis of Sister Chromatid Exchange

For analysis of sister chromatid exchange (SCE), the protocols used by Nagasawa et al (Nagasawa, et al., 1991) were followed. Briefly, cells were subcultured from density-inhibited cultures into three replicate T-25 tissue culture flasks in fresh complete medium containing 10$^{-5}$ M bromodeoxyuridine (BrdUrd) for two rounds of cell replication. For three successive 4-h intervals beginning 15 h after subculturing, colcemid (0.2 g/ml) was added to one of the flasks for a 4-h interval prior to fixation. Therefore, harvesting was carried out over a total period of 12 h. Chromosomes were prepared for the analysis of SCE by the air-dry method, as previously described (Nagasawa and Little, 1979, Nagasawa, et al., 1991). The differential staining of sister chromatids was carried out by the fluorescence plus Giemsa technique (Nagasawa, et al., 1991, Perry and Wolff, 1974). SCE was analyzed at peak mitotic indices after completion of the first or second mitosis.

Tissue Preparation

Normal and tumor tissue samples from wild type and/or Ku70$^{-/-}$ mice were fixed in either 10% buffered formalin and embedded in paraffin, or embedded in a cryopreservative solution (OCT compound, Miles Laboratories, Elkhard, Ind.)., snap-frozen in isopentane precooled in liquid nitrogen, and stored at −70° C.

Similarly, twenty-six cases of either T-cell (n=14) or B-cell (n=12) lymphomas as well as 38 neuroblastomas were obtained from surgically removed specimens at Memorial Sloan-Kettering Cancer Center and were used for this study. Samples were either embedded in a cryopreservative solution (OCT compound, Miles Laboratories, Elkhard, Ind.), snap-frozen in isopentane precooled in liquid nitrogen, and stored at −70° C., or fixed in 10% buffered formalin and embedded in paraffin. Representative hemotoxylin-eosin stained sections (5 μm thick) were examined to evaluate the histopathological characteristics of the lesions to be analyzed, including the ratio of normal-to-tumor content for potential microdissection.

DNA Isolation, PCR-SSCP and DNA Sequencing Assays

DNA was extracted from consecutive 30 μm sections of frozen tissue blocks, using a nonorganic method (Oncor, Gaithersburg, Md.) (Dalbagni, et al., 1993). Nine sets of primers (one pair for each of 9 out of the 13 exons of the Ku70 gene) were designed and used to amplify 50% of the coding region of Ku70.

PCR-SSCP analysis was carried out according to a slight modification of the method of Orita et al. (Orita, et al., 1989). Briefly, amplifications were performed with 50-100 ng genomic DNA in 10 μl volumes. Thirty-five cycles were used for amplification consisting of 20 s at 94° C. for denaturation, 20 s at 55-64° C. for the different primers used, and 30 sec at 72° C. for extension. 3 μl amplified samples were mixed with 7 μl sequencing stop solution, and then were denatured 5-10 min at 95-100° C. and chilled in dry ice. Samples (4 μl) were loaded onto both 5-8% nondenaturing polyacrylamide gels containing 5-10% glycerol, and MDE gel (FMC, Philadelphia, Pa.), and run at room temperature for 18 h at 5 Watts. Gels were dried at 80° C. under vacuum and exposed to x-ray film for 4-24 h.

The same primers used in SSCP were used for DNA sequencing assay. DNA fragments that presented bandshifts in SSCP analysis were sequenced by the dideoxy method (Sanger, et al., 1977) using the Sequenase PCR product sequencing kit (Amersham Life Science, Cleveland, Ohio). Both strands were sequenced for each DNA analyzed. The cases that presented point mutations were reanalyzed by at least two additional sequencing studies.

RNA Preparation, RT-PCR and Mutational Analysis

Total RNAs were prepared using RNeasy Mini Kit from Qiagen. Samples from consecutive 30 μM sections of frozen tissue were disrupted in 600 μl lysis buffer and homogenized. 600 μl ethanol was then added to the lysate and applied to RNeasy mini spin column. Following several washing steps, the contaminants were washed away and RNA was eluted in 40 μl RNase free water. Total RNA prepared from lymphoma and neuroblastoma samples was used for in vitro transcription. About 1 μg of total RNA was used as template in a 25 μl RT reaction containing 40 ng of hexamer random primers. One μl of RT product was then used as template in a 25 μl PCR reaction. Thirty cycles of amplification (30 sec at 94° C., 30 sec at 58° C., 2 min at 72° C.) were performed, and the porducts were analyzed on agarose gels. Four PCR primers and 6 sequencing primers were designed to analyze the whole ORF of Ku70. A 25 μl reaction contained 100 ng genomic DNA or 1 μl RT product, 10 pmol of each primer, 1×Expand™ High Fidelity PCR buffer (Boehringer Mannheim), and 1.3 U Expand™ High Fidelity PCR System enzyme mix (Boehringer Mannheim After an initial denaturation for 2 min at 94° C., 30 cycles of 30 sec at 94° C., 30 sec at 58° C., and 2 min at 72° C., and final extension for 7 min at 72° C. were carried out in a PCR microtube thermal Cycler (Perkin Elmer). Direct sequencing of PCR products was performed after pre-treatment by Pre-PCR sequencing kit (Amersham) using specifically designed sequencing primers. All mutations were confirmed by sequencing a newly amplified product.

Immunohistochemistry

Normal and tumor tissue samples from wild type and/or Ku70$^{-/-}$ mice were fixed in either 10% buffered formalin and embedded in paraffin, or embedded in OCT compound (Miles Laboratories) and frozen in liquid nitrogen at −70° C. In addition, twenty-six human T-cell and B-cell lymphomas were also analyzed, in conjunction with human normal tissue samples of lymph node and spleen. Representative 5 mm sections of normal and tumor tissue samples from wild-type and Ku70$^{-/-}$ mice, as well as the 26 human lymphomas were used for immunophenotyping analyses using an avidin-biotin immunoperoxidase technique (Cordon-Cardo and Richon, 1994, Serrano, et al., 1996). Primary antibodies included anti-mouse CD45 (purified rat monoclonal antibody, 1:500, PharMingen), anti-mouse CD3 (purified rabbit serum, 1:1000, Dako), anti-mouse B220 (purified rat monoclonal antibody, 1:1000, PharMingen), anti-mouse CD19 (purified rat monoclonal antibody, 1:1000, PharMingen), and rabbit anti-chromogranin A (purified rabbit serum, 1:1000, Dako), and were incubated overnight at 4° C. We also used a purified rabbit antiserum to the Ku70 nuclear protein (1:500 dilution). Samples were subsequently incubated with biotinylated secondary antibodies (Vector Laboratories) for 30 min (goat anti-rabbit, 1:500; rabbit anti-rat, 1:100), and then with avidin-biotin peroxidase complexes (1:25 dilution, Vector Laboratories) for 30 min. Diaminobenzadine was used as the chromogen and hematoxylin as the counter stain. Wild type lymphoid organs including thymus, spleen and lymph nodes from different mice were used for titration of the antibodies and positive controls. For negative controls, primary antibodies were substituted with class-matched but unrelated antibodies at the same final working dilutions (Ouyang, et al., 1997). Identification of human Ku70 was achieved using the same purified rabbit anti-Ku70 antiserum. For Ku70 expression, both nuclear and cytoplasmic immunoreactivities were examined; the intensity of the staining was scored as strong positive, moderate positive, weak positive and no staining. Nuclear and cytoplasmic immunoreactivities were classified as continuum data, i.e., from undetectable level or 0% to homogeneous staining or 100%.

Flow Cytometry Analysis of the Spontaneous Tumors

Cell lines were established from each primary tumor as follows. Samples of the tumors were dispersed into cell suspension and plated at various densities in RPMI supplemented with 10% heat-inactivated fetal bovine serum and antibiotics. The cell cultures were split 1:2 and 1:4 until they become established. For flow cytometry analysis, tumor cells of early passages were stained with combinations of antibodies specific for various T- and B-lymphocyte surface markers, such as PE-labeled anti-mouse CD4, and FITC-labeled anti-mouse CD8, and analyzed on a Becton Dickinson FAC scan with Cell Quest software (Ouyang, et al., 1997).

References for the Second Series of Experiments

1. Amiel, J., T. Attie, D. Jan, A. Pelet, P. Edery, C. Bidaud, D. Lacombe, P. Tam, J. Simeoni, E. Flori, C. Nihoul-Fekete, A. Munnich and S. Lyonnet (1996) Heterzygous endothelin receptor B (EDNRB) mutations in isolated Hirschsprung disease. Hum. Mol. Genet., 5, 355-367.
2. Anderson, C. W. (1993) DNA damage and the DNA-activated protein kinase. Trends Biochem. Sci., 18, 433-437.
3. Angrist, M., S. Bolk, B. Thiel, E. G. Puffenberaer, R. M. W. Hofstra, C. H. C. M. Buys, D. T. Cass and A. Chakravarti (1995) Mutation analysis of the RET receptor tyrosine kinase in Hirschsprung disease. Hum. Mol. Genet., 4, 821-830.
4. Attie, T., A. Pelet, P. Edery, C. Eng, J. M. Mulligan, J. Amiel, L. Boutrand, C. Beldjord, C. Niboul-Fekete, A. Munnich, B. Ponder and S. Lyonnet (1995) Diversity of RET proto-oncogene mutations in familial and sporadic Hirschsprung disease. Hum. Mol. Genet., 4, 1381-1386.
5. Badner, J. A., W. K. Sieber, K. L. Garver and A. Chakravati (1990) A genetic study of Hirschsprung disease. Am. J. Hum. Genet., 46, 568-580.
6. Barlow, C., S. Hirotsune, R. Paylor, M. Liyanage, M. Eckhaus, F. Collins, Y. Shiloh, J. N. Crawley, T. Ried D. Tagle and A. Wynshaw-Boris (1996) Atm-deficient mice: aparadigm of Ataxia telangiectasia. Cell, 86, 159-171.
7. Biedermann, K. A., J. R. Sun, A. J. Giaccia, L. M. Tosto and J. M. Brown (1991) scid mutation in mice confers hypersensitivity to ionizing radiation and a deficiency in DNA double-strand break repair. Proc. Natl. Acad. Sci. USA, 88, 1394-1397.
8. Blunt, T., N. J. Finnie, G. E. Taccioli, G. C. M. Smith, J. Demengeot, T. M. Gottlieb, R. Mizuta, A. J. Varghese, F. W. Alt, P. A. Jeggo and S. P. Jackson (1995) Defective DNA-dependent protein kinase activity is linked to V(D)J recombination and DNA repair defects associated with the murine scid mutation. Cell, 0.80, 813-823.

9. Boder, E. (1975) Ataxia-telangiectasia: some historic, clinical and pathologic observations. Birth Defects, 11, 255-270.
10. Bosma, G. C., R. P. Custer and M. J. Bosma (1983) A severe combined immunodeficiency mutation in the mouse. Nature (London), 301, 527-530.
11. Bosma, M. J. and A. M. Carroll (1991) The SCID mouse mutant: definition, characterization, and potential uses. Annu. Rev. Immunol., 9, 323-350.
12. Cai, Q.-Q., A. Plet, J. Imbert, M. Lafage-Pochitaloff, C. Cerdan and J.-M. Blanchard (1994) Chromosomal location and expression of the genes coding for Ku p70 and p80 in human cell lines and normal tissues. Cytogenet Cell Genet, 65, 221-227.
13. Carroll, A. M. and M. J. Bosma (1991) T-lymphocyte development in scid mice is arrested shortly after the initiation of T-cell receptor d gene recombination. Genes Dev., 5, 1357-1366.
14. Carroll, A. M., R. R. Hardy and M. J. Bosma (1989) Occurrence of mature B (IgM+, B220+) and T (CD3+) lymphocytes in scid mice. J. Immunol., 143, 1087-1093.
15. Chan, D. W. and S. P. Lees-Miller (1996) The DNA-dependent protein kinase is inactivated by autophosphorylation of the catalytic subunit. J. Biol. Chem., 271, 8936-8941.
16. Cleary, M. L. (1991) Oncogenic conversion of transcription factors by chromosomal translocations. Cell, 66, 619-622.
17. Cordon-Cardo, C. and V. M. Richon (1994) Expression of the retinoblastoma protein is regulated in normal human tissues. Am. J. Path., 144, 500-510.
18. Dalbagni, G., J. C. Presti Jr, V. E. Reuter, Z. F. Zhang, A. S. Sarkis, W. R. Fair and C. Cordon-Cardo (1993) Molecular genetic alterations of chromosome 17 and p53 nuclear overexpression in human bladder cancer Diagn Mol Pathol, 2, 4-13.
19. Danska, J. S., F. Pflumio, C. J. Williams, O. Huner, J E. Dick and C. J. Guidos (1994) Rescue of T cell-specific V(D)J recombination in SCID mice by DNA-damaging agents. Science, 266, 450-455.
20. Donehower, L. A., M. Harvey, B. L. Slagle, M. J. McArthur, C. A. Montgomery Jr., J. S. Butel and A. Bradley (1992) Mice deficient for p53 are developmentally normal but susceptible to spontaneous tumours. Nature (London), 356, 215-221.
21. Dvir, A., S. R. Peterson, M. W. Knuth, H. Lu and W. S. Dynan (1992) Ku autoantigen is the regulatory componer of a template-associated protein kinase that phosphorylates RNA polymerase II. Proc. Natl. Acad. Sci. USA, 89, 11920-11924.
22. Dyson, H., P. M. Howley, K. Munger and E. Harlow (1989 The human papillomavirus 16 E7 oncoprotein is able to bind to the retinoblastoma gene product. Science, 243, 934-937.
23. Edery, P., T. Attie, J. Amiel, A. Pelet, C. Eng, R. M. W. Hofstra, H. Martelli, C. Bidaud, A. Munnich and S. Lyonnet (1996) Mutation of the endothelin-3 gene in the Waardenburg-Hirschsprung disease (Shah-Waardenburg syndrome). Nat. Genet., 12, 442-444.
24. Gonzalez-Zulueta, M., C. M. Bender, A. S. Yang, T. Nguyen., R. W. Beart, J. M. Van Tornout and P. A. Jones (1995) Methylation of the 5'CpG island of the p16/CDKN2 tumor suppressor gene in normal and transformed human tissues correlates with gene silencing. Cancer Res., 55, 4531-4535.
25. Gottlieb, T. M. and S. P. Jackson (1993) The DNA-dependent protein kinase: requirement for DNA ends and association with Ku antigen. Cell, 72, 131-142.
26. Gu, Y., K. J. Seidl, G. A. Rathbun, C. Zhu,-J. P. Manis, N. van der Stope, L. Davidson, H.-L. Cheng, J. M. Sekiguchi, K. Frank, P. Stanhope-Baker, M. S. Schlissel, D. B. Roth and F. W. Alt (1997). Growth retardation and leaky SCID phenotype of Ku70-deficient mice. Immunity, 7, 653-665.
27. Hammarstein, O. and G. Chu (1998) DNA-dependent protein kinase: DNA binding and activation in the absence of Ku. Proc. Natl. Acad. Sci. USA, 95, 525-530.
28. Hofstra, R. M. W., J. Oningu, G. Tan-Sindhunata, Y. Wu E.-J. Kamsteeg, R. P. Stulp, C. van Ravenswaaij-Arts, D. Majoor-Krakauer, M. Angrist, A. Chakravarti, C. Maijeers and C. H. C. M. Buys (1996) A homozygous mutations in the endothelin-3 gene associated with a combined Waardenburg type 2 and Hirschsprung phenotype (Shah-Waardenburg syndrome). Nat. Genet., 12, 445-447.
29. Jacks, T., L. Remington, B. O. Williams, E. M. Schmitt, S. Halachmi, R. T. Bronson and R. A. Weinberg (1994) Tumor spectrum analysis in p53-mutant mice. Curr. Biol., 4, 1-7.
30. Jackson, S. P. and P. A. Jeggo (1995) DNA double-strange break repair and V(D)J recombination, involvement of DNA-PK. Trends Biochem. Sci., 20, 412-415.
31. Jeggo, P. A., G. E. Taccioli and S. P. Jackson (1995) Menage a trois: double strand break repair, V(D)J recombination and DNA-PK. BioEssays, 17, 949-957.
32. Jhappan, C., H. C. Morse III, R. D. Fleischmann, M- M. Gottesman and G. Merlino (1997) DNA-PKcs: a T-cell tumour suppressor encoded at the mouse scid locus. Nat Genet., 17, 483-486.
33. Kaplan, E. L. and P. Meier (1958) Nonparametric estimation from incomplete observations. J. Am. Stat. Assoc., 53, 457-481.
34. Kirchgessner, C. U., C. K. Patil, J. W. Evans, C. A. Cuomo, L. M. Fried, T. Carter, M. A. Oettinger and J. M. Brown (1995) DNA-dependent kinase (p350) as a candidate gene for the murine SCID defect. Science; 267, 1178-1183.
35. Lees-Miller, S. P. (1996) The DNA-dependent protein kinase, DNA-PK: 10 years and no ends in sight. Biochem Cell Biol., 74, 503-512.
36. Lees-Miller, S. P., R. Godbout, D. W. Chan, M. Weinfeld, R. S: Day III, G. M. Barron and J. Allalunis Turner (1995) Absence of p350 subunit of DNA-activated protein kinase from a radiosensitive human cell line. Science, 267, 1183-1185.
37. Liang, F. and M. Jasin (1996) Ku80-deficient cells exhibit excess degradation of extrachromosomal DNA. J. Biol. Chem., 271, 14405-14411.
38. Lieber, M. R., J. E. Hesse, S. Lewis, G. C. Bosma, N. Rosenberg, K. Mizuuchi, M. J. Bosma and M. Gellert (1988) The defect in murine severe combined immune deficiency: joining of signal sequences but not coding segments in V(D)J recombination. Cell, 55, 7-16.
39. Linzer, D. I. and A. J. Levine (1979) Characterization of 54K dalton cellular SV40 tumor antigen present in SV40-transformed cells and uninfected embryonal carcinoma cells. Cell, 17, 43-52.
40. Little, J. B. (1979) Quantitative studies of radiation transformation with the A31-11 mouse BALB/3T3 cell line. Cancer Res., 0.39, 1474-1480.
41. Loda, M., B. Cukor, S. W. Tam, P. Lavin, M. Fiorentino and G. F. Draetta (1997) Increased proteasome-depended degradation of the cyclin-dependent kinase inhibitor p27 in aggressive colorectal carcinomas. Nat. Med., 3, 231-234.

42. MacPherson, I. (1973) Soft agar techniques. In Tissue Culture Methods and Applications, P. F. Kruse Jr. eds. (New York: Academic Press, pp. 276-280.
43. Merlo, A., J. G. Herman, L. Mao, D. J. Lee, E. Gabrielson, P. C. Burger, S. B. Baylin and D. Sidransk (1995) 5'CpG island methylation is associated with transcriptional silencing of the tumor suppressor p16/CDKN2/MTS1 in human cancers. Nat. Med., 1, 686-692.
44. Mimori, T., M. Akizuki, H. Yamagata, S. Inada, S. Yoshida and M. Homma (1981) Characterization of a high molecular weight acidic nuclear protein recognized by autoantibodies in sera from patients with polymyositis scleroderma overlap. J. Clin. Invest., 68, 611-620.
45. Nagasawa, H. and J. B. Little (1979) Effect of tumor promoters, protease inhibitors and repair processes on x-ray-induced sister chromatid exchanges in mouse cells. Proc. Natl. Acad. Sci. USA, 76, 1943-1947.
46. Nagasawa, H., J. B. Little, W. C. Inkret, S. Carpenter. M.-R. Raju, D. J. Chen and G. F. Strniste (1991) Response of x-ray sensitive CHO mutant cells (xrs-6c) to radiation. II. Relationship between cell survival and the induction of chromosomal damage with low doses of a particles. Radiat. Res., 126, 280-288.
47. Nagasawa, H., G. B. Zamansky, E. F. McCone, C. M. Arundel, E. Matkin and J. B. Little (1987) Spontaneous transformation to anchorage-independent growth of a xeroderma pigmentosum fibroblast cell strain. Journal of Investigative Dermatology, 88, 149-153.
48. Nussenzweig, A., C. Chen, V. da Costa Soares, M. Sanchez, K. Sokol, M. C. Nussenzweig and G. C. Li (1996) Requirement for Ku80 in growth and immunoglobulin V(D)J recombination. Nature (London), 382, 551-555.
49. Orita, M., H. Iwahana, H. Kanazawa, K. Hayashi and T. Sekiya (1989) Detection of polymorphisms of human DNA by gel electrophoresis as single-strand conformation polymorphisms. Proc. Natl. Acad. Sci. USA, 86, 2766-2770.
50. Ouyang, H., A. Nussenzweig, A. Kurimasa, V. da Costa Soares, X. Li, C. Cordon-Cardo, W. Li, N. Cheong, M. Nussenzweig, G. Iliakis, D. Chen and G. C. Li (1997) Ku70 is required for DNA repair but not for TCR gene recombination in vivo. J. Exp. Med., 186, 921-929.
51. Pan, Z. Q., A. A. Amin, E. Gibbs, H. Niu and J. Hurwitz (1994) Phosphorylation of the p34 subunit of human single-stranded-DNA-binding protein in cyclin A-activated GI extracts is catalyzed by cdk-cyclin A complex and DNA-dependent protein kinase. Proc. Natl. Acad. Sci. USA, 91, 8343-8347.
52. Pavan, W. J., R. A. Liddell, A. Wright, G. Thibaudeau, P. G. Matteson, K. M. McHugh and L. D. Siracusa (1995) A high-resolution linkage map of the lethal spotting locus: a mouse model for Hirschsprung disease. Mammalian Genome, 6, 1-7.
53. Perry, P. and S. Wolff (1974) New giemsa method for the differential staining of sister chromatids. Nature (London), 251, 156-158.
54. Peterson, S. R., A. Kurimasa, M. Oshimura, W. S. Dynan, E. M. Bradbury and D. J. Chen (1995) Loss of the catalytic subunit of the DNA-dependent protein kinase in DNA double-strand-break-repair mutant mammalian cells. Proc. Natl. Acad. Sci. USA, 92, 3171-3174.
55. Pingault, V., A. Puliti, M. O. Prehu, A. Samadi, N. Bondurand and M. Goossens (1997) Human homology and candidate genes for the Dominant megacolon locus, a mouse model for Hirschsprung disease. Genomics, 39, 86 89.
56. Ponce-Castaneda, M. V., M.-H. Lee, E. Latres, K. Polyak, L. Lacombe, K. Montgomery, S. Mathew, K. Krauter, J. Sheinfeld, J. Massague and e. al. (1995) p27Kip1: chromosomal mapping to 12p12-12p13.1 and absence of mutations in human tumors. Cancer Res., 55, 1211-1214.
57. Porter, P. L., K. E. Malone, P. J. Heagerty, G. M. Alexander, L. A. Gatti, E. J. Firpo, J. R. Daling and J. M. Roberts (1997) Expression of cell cycle regulators p27Kip1 and cyclin E, alone and in combination, correlate with survival in young breast cancer patients. Nat. Med., 3, 222-225.
58. Purdie, C. A., D. J. Harrison, A. Peter, L. Dobbie, S. White, S. E. Howie, D. M. Salter, C. C. Bird, A. H. Wylie, M. L. Hooper and A. R. Clarke (1994) Tumor incidence, spectrum and ploidy in mice with a large deletion in the p53 gene. Oncogene, 9, 603-609.
59. Rathmell, W. K. and G. Chu (1994) Involvement of the Ku autoantigen in the cellular response to DNA double-strand breaks. Proc. Natl. Acad. Sci. USA, 91, 7623-7627.
60. Roth, D. B., T. Lindahl and M. Gellert (1995) How to make ends meet. Curr. Biol., 5, 496-499.
61. Sanger, F., S. Nicklen and A. R. Coulson (1977) DNA sequencing with chain-terminating inhibitors. Proc. Natl. Acad. Sci. USA, 74, 5463-5467.
62. Sarnow, P., Y. S. Ho, J. Williams and A. J. Levine (1982) Adenovirus E1b-58 kd tumor antigen and SV40 large tumor antigen are physically associated with the same 54 kd cellular protein in transformed cells. Cell, 28, 387-394.
63. Sedgewick, R. and E. Boder (1991) Ataxia-telangiectasia. In Handbook of Clinical Neurology, P. Vinken, G. Bruyn and H. Klawans eds. (New York: Elsevier Scientifice Publishers, pp. 347-423.
64. Serrano, M., H.-W. Lee, L. Chin, C. Cordon-Cardo, D. Beach and R. A. DePinho (1996) Role of the INK4a in tumor suppression and cell mortality. Cell, 85, 27-37.
65. Sipley, J. D., J. C. Menninger, K. O. Hartley, D. C. Ward, S. P. Jackson and C. W. Anderson (1995) Gene for the catalytic subunit of the human DNA-activated protein kinase maps to the site of the XRCC7 gene on chromosome 8. Proc. Natl. Acad. Sci. USA, 92, 7515-7519.
66. Smider, V., W. K. Rathmell, M. R. Lieber and G. Chu (1994) Restoration of x-ray resistance and V(D)J recombination in mutant cells by Ku cDNA. Science, 266, 288-291.
67. Smith, C. A., G. T. Williams, R. Kingston, E. J. Jenkinson and J. J. T. Owen (1989) Antibodies to CD3/T-cell receptor complex induce death by apoptosis in immature T cells in thymic cultures. Nature (London), 337, 181-184.
68. Southard-Smith, E. M., L. Kos and W. J. Pavan (1998) Sox10 mutation disrupts neural crest development in Dom Hirschsprung mouse model. Nat. Genet., 18, 60-64.
69. Suwa, A., M. Hirakata, Y. Takeda, S. A. Jesch, T. Mimori and J. A. Hardin (1994) DNA-dependent protein kinase (Ku protein-p350 complex) assembles on double-stranded DNA. Proc. Natl. Acad. Sci. USA, 91, 6904-6908.
70. Taccioli, G. E., T. M. Gottlieb, T. Blunt, A. Priestly, J. Demengeot, R. Mizuta, A. R. Lehmann, F. A. Alt, S. P. Jackson and P. A. Jeggo (1994) Ku80: product of the XRCC5 gene and its role in DNA repair and V(D)J recombination. Science, 265, 1442-1445.
71. Takiguchi, Y., A. Kurimasa, F. Chen, P. E. Pardington, T. Kuriyama, R. T. Okinaka, R. Moyzis and D. J. Chen (1996) Genomic structure and chromosomal assignment of the mouse Ku70 gene. Genomics, 35, 129-135.
72. Thompson, L. H. and P. A. Jeggo (1995) Nomenclature of human genes involved in ionizing radiation sensitivity Mutat. Res., 337, 131-133.

73. Tsukada, T., Y. Tomooka, S. Takai, Y. Ueda, S. Nishikawa, T. Yagi, T. Tokunaga, N. Takeda, Y. Suda, S Abe, I. Matsuo, Y. Ikawa and S. Aizawa (1993) Enhanced proliferative potential in culture of cells from p53-deficient mice. Oncogene, 8, 3313-3322.
74. Werness, B. A., A. J. Levine and P. M. Howley (1990) Association of human papillomavirus types 16 and 19 E6 proteins with p53. Science, 248, 76-79.
75. Whyte, P., K. J. Buchkovich, J. M. Horowitz, S. H. Friend, M. Raybuck, R. A. Weinberg and E. Harlow (1988 Association between an oncogene and an anti-oncogene: the adenovirus E1A proteins bind to the retinoblastoma gene product. Nature (London), 334, 124-129.
76. Yaneva, M., T. Kowalewski and M. R. Lieber (1997) Interaction of DNA-dependent protein kinase with DNA and with Ku: biochemical and atomic-force microscopy studies. EMBO J., 16, 5098-5112.
77. Zhu, C., M. A. Bogue, D.-S. Lim, P. Hasty and D. B. Roth (1996) Ku86-deficient mice exhibit severe combine immunodeficiency and defective processing of V(D)J recombination intermediates. Cell, 86, 379-389.

Third Series of Experiments

Ku-Deficient Cells are Sensitive to γ-Rays and Chemotherapeutic Agents

Survival experiments using cells derived from either Ku70 or Ku80 knock-out mice have shown that these cells are very sensitive to γ-radiation and several chemotherapeutic agents, specifically those agents that induce DNA strand breaks, such as: bleomycin, etoposide, and adriamycin (FIG. 12).

HSP70 Promoter Analysis

Experiments were performed to test the transcriptional activity of the mouse hsp70 promoter. For these experiments, first, the plasmid N3Luc, a reporter gene construct which contains the mouse hsp70 promoter upstream of the firefly luciferase gene was used for our studies. Cells were transiently transfected with this mouse hsp70 promoter-driven luciferase reporter gene construct. Comparison of the luciferase activity before and 8 hours after heat shocking the cells demonstrated that a) this promoter showed little "leakiness" (i.e. low transcription under normal conditions) and b) a high heat-inducible activity. The transcriptional activity after a 15 minute 45° C. heat shock was at least 30 fold increased relative to control levels. Other investigators have reported even higher induction levels (>100 fold) for this promoter (Nguyen et al., J. Biol. Chem. 264: 10487 (1989)).

Mutant of the hsp70 promoter were then generated, including 5'-deletion, linkerscanner mutations and point mutations, fused to the firefly luciferase reporter gene (the mutant N3Luc construct is designated ΔN3Luc), and examined the heat-induced reporter gene expression. Our results showed that specific deletion (e.g., either at 5' or in the centra region of hsp70 promoter) increased the heat induction of transcriptional activity (as measured by firefly luciferase reporter gene activity) by an additional several fold when compared to the heat inducibility of the intact, not mutated promoter. Further data indicate that in cells deficient in Ku70 or Ku80 the heat induction of hsp70 promoter activity is further enhanced.

Figure 13B:
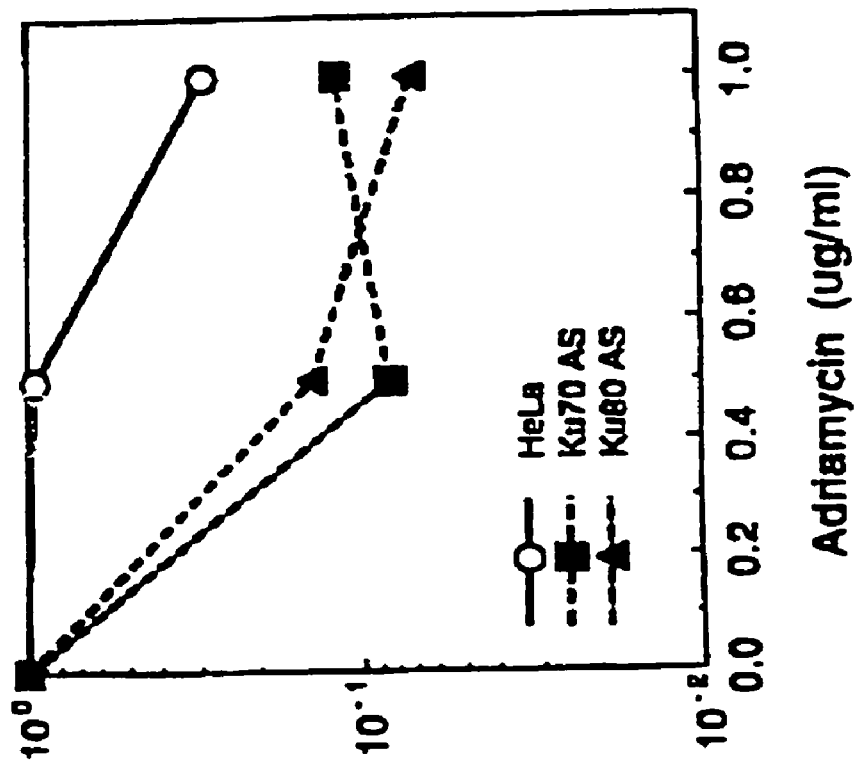
Figure 13A:
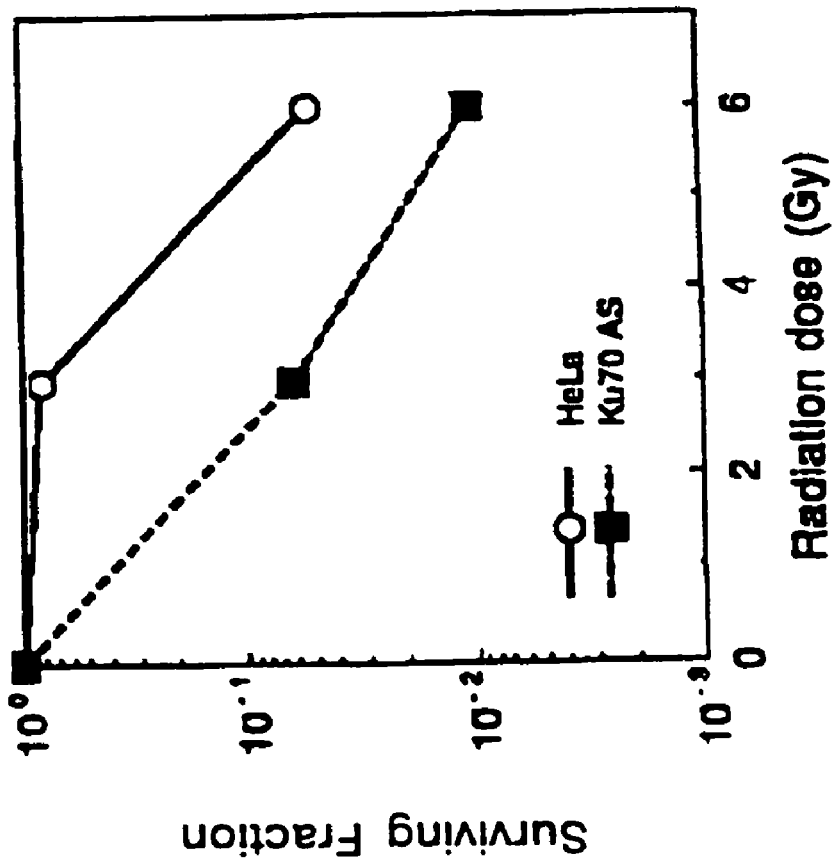

Stable HeLa cells, containing human Ku70 cDNA or human Ku80 cDNA, in the antisense orientation, under the regulation of the Tet-Off™ expression system (Clonetech), were established. Upon induction of the expression system these cells should produce antisense Ku70 or Ku80 RNA, respectively. Experiments were performed showing (FIG. 13) that expression of either Ku70 or Ku80 antisense RNA increased the cytotoxic effect adriamycin by 3-5 fold at 1 μg/ml and that expression of Ku70 antisense RNA increased the cytotoxic effect of y-radiation approximately 5 fold (at 6 Gy).

Fourth Series of Experiments

Catalytic Subunit of DNA-Dependent Protein Kinase: Impact on Lymphocyte Development and Tumorigenesis Introduction The DNA-dependent protein kinase (DNA-PK) consists of a heterodimer DNA-binding complex, Ku70 and Ku80, and a large catalytic subunit, DNA-PKcs. To examine the role of DNA-PKcs in lymphocyte development, radiation sensitivity, and tumorigenesis, we disrupted the mouse DNA-PKcs by homologous recombination. DNA-PKcs-null mice exhibit no growth retardation nor a high frequency of T-cell lymphoma development, but show severe immuodeficiency and radiation hypersensitivity. In contrast to the Ku70-/- and Ku80-/- phenotype, DNA-PKcs-null mice are blocked for V(D)J coding but not for signal-end joint formation. Furthermore, inactivation of DNA-PKcs leads to hyperplasia and displasia of the intestinal mucosa, and production of aberrant crypt foci, suggesting a novel role of DNA-PKcs in tumor suppression.

Severe combined immunodeficiency (SCID) mice are hypersensitive to radiation, deficient in DNA double-strand break repair and impaired in V(D)J recombination. Recent studies strongly suggest that the SCID defect lies in the gene encoding the catalytic subunit of DNA-dependent protein kinase DNA-PK(1-3). DNA-PK is a serine/threonine kinase consisting of a 465-kDa catalytic subunit (DNA-PKcs) and a heterodimeric regulatory complex termed Ku, which is composed of a 70-kDa (Ku70) and an 86-kDa (Ku80) polypeptide. Although it is generally believed that Ku helps to recruit DNA-PKcs to DNA in vitro and is likely to be required for the physiological activation of DNA-PK at the site of DNA damage (4,5), there is evidence at least in vitro that DNA-PKcs can itself bind to linear DNA fragments and become activated for kinase activity in the absence of Ku (6,7). It has been shown that the SCID phenotype correlates with a nonsense mutation at Tyr-4046 in the extreme carboxyl-terminal region of the DNA-PKcs gene (8-10). This T to A transversion results in the substitution of ocher termination codon and a loss of 83 amino acids from the extreme C-terminal end(9, 10). Therefore, one plausible reason for the "leaky" phenotype of SCID is that the truncated DNA-PKcs protein has weak activity, but functionally sufficient for some T-cell development. Recently, Jhappan et al. (11) generated homozygous mice from the transgenic mice harboring the yeast cAMP phosphodiesterase gene (designated Sra5-1 or slip mouse). The Sra-1 homozygotes were found to be immunodeficient, lack mature lymphocytes, suggesting that the transgene had integrated into a gene required for the normal development of T and B cells. The integration of the transgene was subsequently shown to occur directly into the DNA-PKcs locus, as suggested by chromosomal localization of the transgene, the complementation experiments with SCID mice, and the depleted levels of DNA-PK activity. The most striking difference from SCID phenotype, however, is the strong predisposition to thymic lymphoblastic lymphomas which arise in slip mice with complete penetrance. In contrast, lymphoma develop in only about 15% of CB-17 SCID mice, and have not been reported for Ku80 null mice. Integration of these data to generate a global model for the role of DNA-PK complex in tumorigenesis/or tumor suppression is simply difficult. First, assuming that DNA-PK activity requires the assembly of Ku and DNA-PKcs on DNA breaks, then comparison between the Ku80−/− (no tumor development) and slip phenotype (100% penetrance of tumor development) suggests that DNA-PK kinase activity is not required for tumor suppression. Perhaps other distinct functions for this kinase molecule, independent of Ku, are involved in tumor suppression, and inactivation of which leads to the predisposition of thymic lymphoma as seen in the slip mice. It is also plausible that in the generation of slip mice, the multiple copies of transgenes incorporated in DNA-PKcs locus may affect the adjacent gene(s) expression, for example, via methylation or positioning effect. One of these cis-activated/inactivated genes may function as an oncogene/tumor suppressor gene.

To elucidate the function of the individual components of DNA-PK in vivo, we have previously generated Ku70−/− and Ku80−/− mice (13, 16). In the present study, we disrupted DNA-PKcs gene via homologous recombination. In the resultant DNA-PKcs−/− mice, T- and B-lymphocyte development was arrested, V(D)J coding-end rearrangement was deficient, but V(D)J signal-end joining ability was intact. DNA-PKcs-null mice exhibit no growth retardation nor a high frequency of T-cell lmyphoma development. Furthermore, inactivation of DNA-PKcs leads to hyperplasia and displasia of the intestinal mucosa, and production of aberrant crypt foci, suggesting a novel role of DNA-PKcs in tumor suppression.

Materials and Methods

Targeted Disruption of DNA-PKcs and Generation of DNA-PKcs−/− Mice

Mouse genomic DNA-PKcs gene was isolated from sCos-I cosmid library constructed from a mouse strain 129 embryonic stem (ES) cell line. The targeting vector was constructed by substituting half of the exon 3 and part of the intron 3 with-neo gene. The targeting construct was linearized with NotI and transfected into CJ7 ES cells by electroporation. Four hundred clones were screened and eight positive pools were initially identified by PCR. One positive ES clone carrying the targeted mutation of DNA-PKcs was identified by second round PCR, and further confirmed by Southern blot analysis. This positive ES clone was injected into C57BL/6 blastocysts and surgically implanted into pseudopregnant females to generate chimeric mice. The chimeras were crossed with C57BL/6 females, resulting in five mice with germline transmission out of seven males screened. The DNA-PKcs−/− mice were obtained by intercrossing DNA-PKcs+/−mice. CB-17 SCID mice were obtained from Taconic (Germantown, N.Y.).

The genotype of the mice was determined by PCR which distinguishes endogenous from the targeted DNA-PKcs allele. PCR reaction contains 1 μg genomic DNA; 0.6 μM (each) of primers MD-20: TATCCGGAAGTCGCTTAGCA-TTG (SEQ ID NO: 42); MD-21: AAGACGGTTGAAGTCA-GAAGTCC (SEQ ID NO: 43); and POL-8: TTCACATA-CACC-TTGTCTCCGACG (SEQ ID NO: 44); 0.2 mm (each) DNTP; 1.5 mM $MgCl_2$ and 2.5U of Taq polymerase. Primers MD-20 and MD-21 give a product of wild type allele that is 264 bp; primers MD-20 and Pol-8 yield a product of the targeted allele that is 360 bp.

Establishment of Primary and SV40 Transformed Cell Lines

Primary lung fibroblast cells were isolated from 4-week-old DNA-PKcs wild type (+/+), heterozygous (+/−), homozygous (−/−) mice, and CB-17 SCID mouse. Cells were maintained at 37° C. in a humidified atmosphere of 5% $CO_2$ in air using alpha-MEM medium supplemented with 10% fetal calf serum, 100 Unit/ml penicillin and 100 μg/ml streptomycin. SV40 transformed lung fibroblast were obtained by transfecting SV40 T-antigen expression plasmid using a calcium phosphate transfection system (Cat.#18306-019, Gibco BRL, Gaithersburg, Md.).

RT-PCR, Western Blot Analysis and In Vitro Kinase Assay

For RT-PCR assay, total RNA was prepared from SV40 transformed lung fibroblast cells using Qiagen RNeasy kit (Qiagen Inc., Santa Clarita, Calif.). After digestion of contaminated genomic DNA by DNase I (Ambion, Austin Tex.), cDNA synthesis was carried out with the Superscript preamplification system (Gibco BRL, Gaithersburg, Md.) according to the included protocol. PCR primers used for RT-PCR were MD-3: ATCAGAAGGTCTAAGGCTGGAAT (SEQ ID NO: 45), MD-5: CGTACGGTGTTGGCTACTGC (SEQ ID NO: 47) for amplification between exon 1 and 4 of DNA-PKcs, MD-28: CACTGAGGGCTT-TCCGCTCTTGT (SEQ ID NO: 47), MD-29: GCTCTTGTGCACGAATGTTGTAG (SEQ ID NO: 48) for PI-3 kinase domain, and GA-5: AGAA-GACTGTGGATGGCCCC (SEQ ID NO: 49), GA-3: AGGTCCACCACCC-TGTTGC (SEQ ID NO: 50) for control GAPDH amplification.

Whole cell extracts were prepared as described previously (15). Protein concentration of the extracts was determined by Bradford analysis using BSA as a standard. Western blotting analysis of DNA-PKcs and Ku70 was performed as described previously (16) using the DNA-PKcs monoclonal antibody [42-26] and anti-mouse Ku70 goat-polyclonal antibody M-19 (Santa Cruz Biotechnology Inc., Santa Cruz, Calif.).

Histology and Cell Preparation and Flow Cytometric Analysis

To determine the pathological changes, histological sections of various organs of DNA-PKcs−/− and wild-type littermate mice were prepared and examined as previously described (16, 18). For flow cytometry, single cell suspensions from lymphoid organs of 4- to 9-week-old mutants, their littermate controls and CB-17 SCID mice were prepared for staining as described previously (16) and analyzed on FACScan With Cell Quest software (Becton Dickinson, San Jose, Calif.). Cells were stained with combinations of PE-labeled anti-CD4 and FITC-labeled anti-CD8, or PE-labeled anti-B220 and FITC-labeled anti-CD43, or FITC-anti-IgM and PE-anti-B220 (PharMingen), as needed. Bone marrow cells were harvested from femurs by syringe lavage, and cells from thymus and spleen were prepared by homogenization. Cells were collected and washed in PBS plus 5% FCS and counted using a hemacytometer. Samples from individual mice were analyzed separately. Dead cells were gated out by forward and side scatter properties. Experiments were performed at least three times and yielded consistent results.

DNA Preparation and Analysis of V(D)J Recombination Products

T cell antigen receptor (TCR) and immunoglobulin recombination in T and B lymphocytes were measured by amplifying rearranged DNA fragments using PCR. Genomic DNAs were isolated from thymus, spleen and bone marrow (BM) from 4-to 9-week-old DNA-PKcs heterozygous (+/−), homozygous (−/−) mice and SCID mice. Oligonucleotides for PCR primers and probes are as follow. For TCR $V^β8$-$J^β2$ rearrangement (16), $V_β8.1$: GAGGAAAGGTGACAT-TGAGC (SEQ ID NO: 51), $J_β2.6$: GCCTGGTGCCGGGAC-CGAAGTA (SEQ ID NO: 29), and $V_β8$ probe: GGGCT-GAGGCTGATCCATTA (SEQ ID NO: 52). For $TCR_δ$ $D_δ2$-$J_δ1$ rearrangement, DR6: TGGCTTGACATGCAGAAAACACCTG (SEQ ID NO:

31), DR53: TGAATTCCACAGTCACTTGGGTTC (SEQ ID NO: 53) and DR2 probe: GACACGTGATACAAAGC-CCAGGGAA (SEQ ID NO: 33). For $TCR_\delta$ $D_\delta 2$-$J_\delta 1$ signal joint (19), DR21: GTCATATCTTGTCCAGTCAACTTCC (SEQ ID NO: 54), DR162: GATGAGCCAGCTGGATGAG-TAACAC (SEQ ID NO: 55), and DR161 probe: GCCCTCTAGCCATGACA TCAGAGC (SEQ ID NO: 56). For immunoglobulin $V_H 7183$-$J_H 4$ rearrangement(19), DR214: CGCGAAGCTTCGT GGAGTCTGGGGA (SEQ ID NO: 57), DR217: GGGGAATTCCTGAGGAGACGGT-GACT (SEQ ID NO: 58), and DR218 probe: ACCCCAG-TAGTCCATAGCATAGTAAT (SEQ ID NO: 59). For control GAPDH amplification, same primers were used as RT-PCR experiment. Probe DNA for mouse GAPDH was purchased from Ambion Inc. (Cat.#7330, Austin Tex.). Amplified PCR products were resolved on 2% of agarose gel in 0.5×TBE, and transferred to Hybond N+ nylon membrane. Using radiolabeled oligonucleotide or DNA probes, PCR products were hybridized and visualized by autoradiography.

Radiation Survival Assays

Survival curves for each cell line were obtained by measuring the colony-forming ability of irradiated cell populations. Cells were plated on 60-mm plastic petri dishes and irradiated with $^{137}Cs$ (y-rays at the rate of 2.2 Gy/min to achieve a cumulative dose of 1, 2, 3 or 5 Gy 2 hrs after plating. After 7 days cells were fixed and stained with 1% crystal violet in a 70% ethanol solution and colonies which contained more than 20 cells were scored and the mean value for triplicate culture dishes was determined. Cell survival was normalized to plating efficiency of untreated controls for each cell type.

Results

Targeted Disruption of DNA-PKcs Gene

Figure 15A:
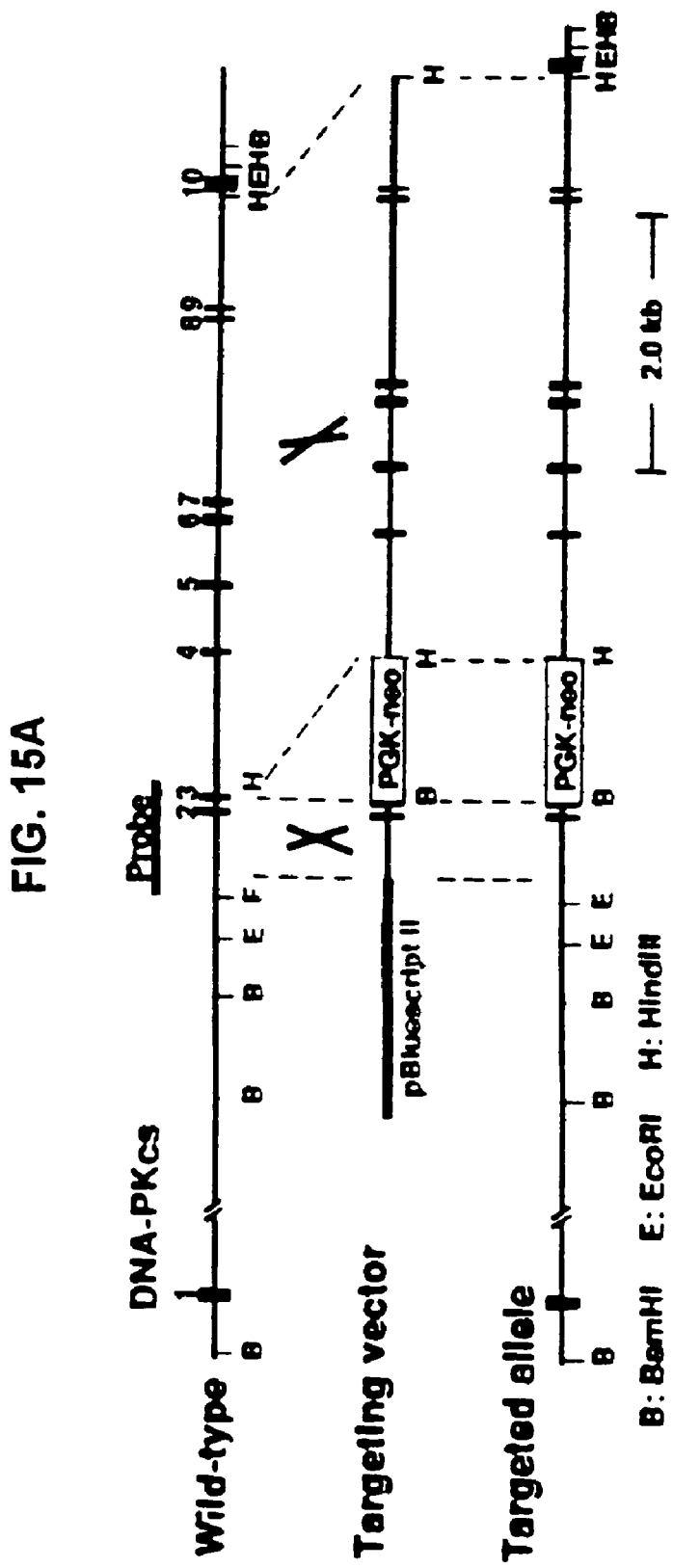
Figure 15C:
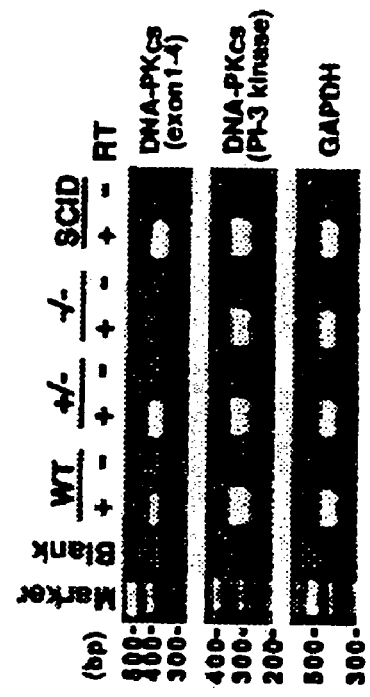
Figure 15B:
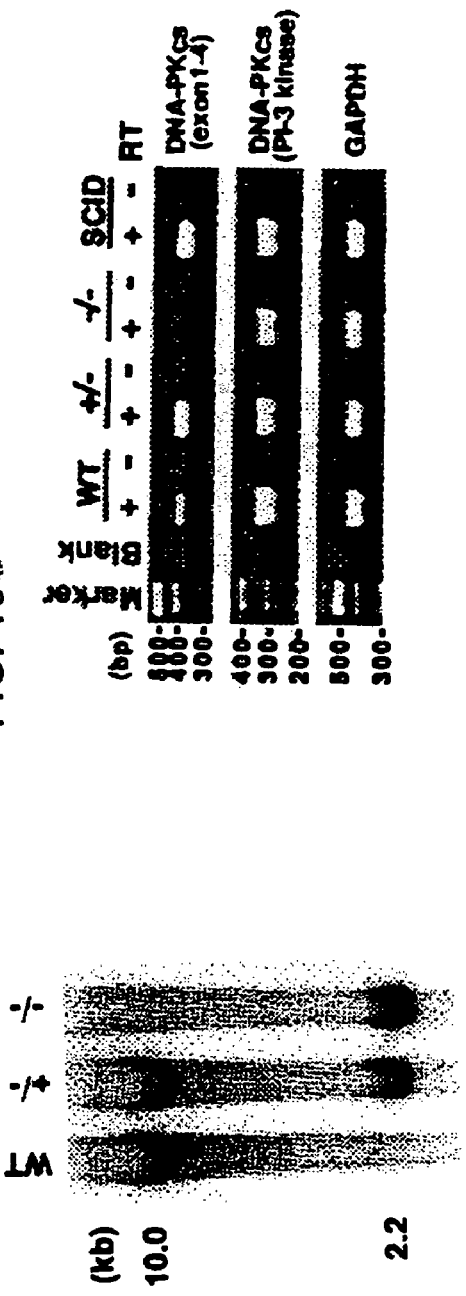

To determine the roles of DNA-PKcs in vivo, we targeted DNA-PKcs in mice via homologous recombination. DNA-PKcs gene was inactivated by substituting 3'-half of the exon 3 and part of the intron 3 with PGK-neo gene (FIGS. 15A and 15B) Mice heterozygous for the targeted DNA-PKcs allele did not show any detectable defects compared with the wild type littermates. These PKcs+/− heterozygotes were subsequently bred with each other generating PKcs−/− homozygotes in 25% of the offspring. Therefore, disruption of DNA-PKcs gene did not result in embryonic lethality. Adult PKcs−/− mice are fertile, and give comparable litter size (about 6 pups) relative to PKcs+/− or PKcs+/+ mice (about 8 pups). In contrast to the 50% smaller body size of Ku70−/− and Ku80−/− mice (13, 16), PKcs−/− mice were about the same size as their PKcs+/−and PKcs+/+littermates.

Figure 15D:
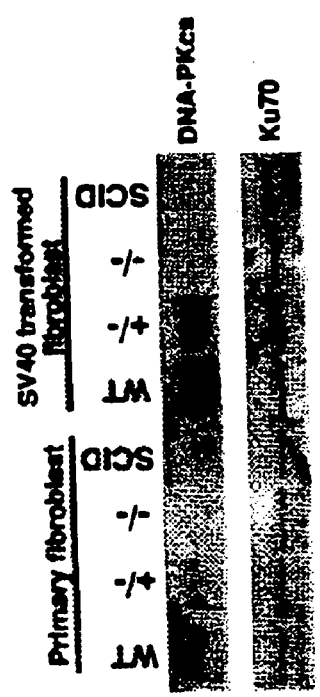

To confirm that the disruption produced a null mutation, DNA-PKcs mRNA and protein expression were analyzed by RT-PCR, Western blotting and in vitro DNA-PK kinase assay. It is clearly shown in FIG. 1C that the RT-PCR products between exon 1 and exon 4 were absent in DNA-PKcs−/− cells. DNA-PKcs immunoreactivity was undetectable (FIG. 15D), and there was no kinase activity in DNA-PKcs−/− fibroblasts (data not shown) The levels of DNA-binding component, the Ku70 and Ku80 proteins, were similar to that of the wild-type controls (FIG. 15D and data not shown).

Development of T- and B-Lymphocytes is Blocked at Early Stage in DNA-PKcs−/− Mice To determine whether there were specific pathological changes in the targeted mice, we examined the histology of various organs (FIG. 16A). With the exception of their lymphoid organs and gastrointestinal tract, DNA-PKcs−/− mice appeared normal. Spleen and lymph nodes were disproportionately smaller by 5-10 fold relative to controls and were devoid of lymphocytes. The DNA-PKcs−/− thymus was also disproportionately smaller, had no cortical-medullary boundary, and contained 50-100-fold fewer thymocytes than wild-type littermates (2-6×$10^6$ and 2×$10^8$, respectively). In addition, the gut-associated lymphoid tissue, specialized structures called Peyer's patches in the small intestine, was drastically reduced or absent.

To examine the immunological defect in DNA-PKcs−/− mice, cells from thymus, bone marrow and spleen were labeled with monoclonal antibodies specific for lymphocyte surface markers and analyzed using multiparameter flow cytometry. Consistent with the histological data, there was a complete absence of mature B cells in the spleen (FIG. 16B). Examination of the bone marrow showed that B-cell development was blocked at early progenitor B220+ CD43+ stage.

DNA-PKcs−/− thymus displayed variable contents of cells expressing $CD4^+CD8+$ thymocytes (1-7%), although CD4− CD8− cells usually made up the majority population (~95%). The spleen cells from DNA-PKcs−/− mice contained detectable CD4+ single positive T cells (1-5%), which was slightly more than that reported for SCID mice. Taken together, the immunological phenotype in DNA-PKcs−/− mice closely resembles that of SCID, but differs from those of Ku80−/− and Ku70−/− mice (13, 16). In terms of successful T-cell development, the rank order is wild type, Ku70−/−, DNA-PKcs−/−, SCID, Ku80−/−, with Ku80−/− being the most deficient.

T-Cell Receptor and Immunoglobulin Gene Rearrangement

To determine whether a null mutation in DNA-PKcs affects rearrangements of antigen-receptor gene segments in T and B lymphocytes in vivo, DNA from the bone marrow was amplified with primers specific to immunoglobulin V-$DJ_H$ rearrangements, and DNA from the thymus was amplified with primers that detect V-$DJ_\beta$ and $D_\delta$-$J_\delta$-rearrangements (FIG. 16C). Similar to that found in SCID mice, V-$DJ_H$ rearrangements were not detected in DNA-PKcs−/− B cells, possibly accounting for the absence of mature B cells in these mutant mice.

DNA-PKcs −/− T cells in the thymus and spleen do undergo $D_\delta 2$-$J_\delta 2$ recombination at a level which is similar to that found in SCID mice and in the heterozygous littermates. However, the V-$DJ_\beta$ rearrangements were significantly reduced in both quantity and diversity (FIG. 16C). Signal joint formation of $D_\delta$-$J_\delta$ rearrangements in both DNA-PKcs−/− and SCID mice shows, however, much higher signals than control heterozygous littermates. In conclusion, our results demonstrate that DNA-PKcs is required for coding but not for signal joint formation in mice, a phenotype that closely resembles that found in SCID mice, but distinctly different from the Ku70−/− or Ku80−/− mice.

Absence of DNA-PKcs Confers Radiation Hypersensitivity

To demonstrate that inactivation of DNA-PKcs leads to hypersensitivity to ionizing radiation, monolayers of DNA-PKcs−/−, DNA-PKcs+/−, and DNA-PKcs+/+ lung fibroblasts were exposed to graded doses of (y-irradiation (0-5 Gy), and survival was determined by the colony formation assay. FIG. 17 clearly shows that DNA-PKcs−/− cells were much more radiosensitive than the heterozygous and the wild type controls, with a >100-fold difference in survival after 5 Gy of (y-irradiation. The radiation dose-response curve of DNA-PKcs−/− cells was, however, nearly identical to that of the SCID lung fibroblast cells.

Preneoplastic Lesions in DNA-PKcs-/- Mice

Recently, Jhappan et al (11) reported that the integration of a transgene at the DNA-PKcs locus resulted in strong predisposition to thymic lymphoblastic lymphomas, which arise in slip mice with complete penetrance. To examine whether our DNA-PKcs-/- mice are also susceptible to tumor development, we randomly assigned litters arising from heterozygous intercrosses (e.g., PKcs+/+, PKcs+/-and PKcs-/-) as well as homozygous crosses, and monitored the mice daily for tumor development and survival. None of the DNA-PKcs+/+(n=59) and DNA-PKcs+/-(n=102) littermates developed tumors through an observation period of twelve months. Among 120 DNA-PKcs-/- mice, only 3 developed thymic lymphomas between 3 to 12 months of age, in sharp contrast to the observation with slip mice.

Autopsy examination of the lower gastrointestinal tract revealed the lack of mature Peyer's patches in DNA-PKcs-/- mice. In addition, we observed an increase in cellularity in the colonic glands, which was confirmed by the Ki67 proliferative index (data not shown). In each of 21 randomly selected, healthy DNA-PKcs-/- mice (ages between 1 to 6 months), we found intestinal segments with inflammatory infiltrates composed of polymorphonuclear cells, resulting in histopathological changes compatible with inflammatory polyps (FIG. 18A). In addition, in 15 of these 21 null mice, we detected the presence of hyperplastic polypoid lesions, composed of well differentiated colonic epithelial cells with foci of mild to moderate dysplasia (FIG. 18B). In eight cases we found areas of moderate to severe dysplasia. In the cases with severe dysplasia, we further identified areas of loose connective tissue stroma and dysplastic cells intruding the core of the stalk, suggesting invasion into the lamina propria (FIG. 18C). Furthermore, three of these cases revealed segments of colonic mucosa replaced by flat lesions composed of dysplastic cells, reminiscent of the so-called aberrant crypt foci (FIG. 18D). In two of these cases, these changes were observed along all intestine, including the small bowel.

Discussion

In summary, we carried out targeted disruption of DNA-PKcs-/- gene in mice via homologous recombination. In the resultant DNA-PKcs-/- mice, both T- and B-lymphocyte development were arrested at early progenitor stages, V(D)J coding-end rearrangement deficient, but V(D)J signal-end joining ability intact. DNA-PKcs-/- fibroblasts are hypersensitive to radiation and deficient in the repair of DNA double strand breaks (data not shown). Taken together, our data conclusively demonstrate DNA-PKcs-/- is essential for the development of T- and B-lymphocytes. We have also provided direct and definitive genetic evidence that the SCID phenotype is caused by the alteration of DNA-PKcs protein. The striking similarity between DNA-PKcs-/- and SCID mice in terms of their lymphocyte development and V(D)J recombination suggest that the "leaky" phenotype frequently observed in the lymphocyte development of SCID mice may not be due to the "leakiness" of DNA-PKcs expression. Thus, there may exist alternate, perhaps less efficient, pathways in V(D)J recombination lymphocyte development.

Of significant interest are three other novel findings. First, during an 12-month observation period, only 3 out of 120 DNA-PKcs-/- mice developed thymic lymphoma. This low frequency of thymic lymphoma is similar to that observed in Ku80-/- and SCID mice, but distinctly different from Ku70-/- mice and slip mice in which DNA-PKcs locus was disrupted by the integration of a transgene (11). The marked difference between DNA-PKcs-/- (with a less than 3% incidence of spontaneous tumor development) and slip mice (which show strong predisposition to thymic lymphoblastic lymphomas) raises the question for the role of DNA-PKcs in lymphomagenesis. While DNA-PKcs plays a crucial role in DNA DSB repair and V(D)J recombination, our data suggest that the DNA-PK catalytic subunit is not essential for T-cell tumor suppression. Differences in genetic background are unlikely to contribute to the different phenotypes of Ku70-/- and Ku80-/- and DNA-PKcs-/- in the development of tumors. All of our Ku70-/- and Ku80-/- and DNA-PKcs-/- strains were in a mixed 129/SV×C57 µL/6 background and were generated in the transgenic mouse core facility at Memorial Sloan-Kettering Cancer Center using identical protocols. Furthermore, an independently derived line of DNA-PKcs-/- mice had a phenotype essentially identical to that we described (20). And, up-to-date, the propensity for lymphoma development has not been reported in DNA-PKcs-deficient mice generated via targeted disruption (20, 21).

Second, that DNA-PKcs-/- mice are able to carry out signal-end rejoining and exhibit no growth retardation, in contrast to Ku70-/- and Ku80-/- animals (13, 16, 22), strongly suggests that Ku proteins may have functions in V(D)J recombination and DNA damage repair that are independent of DNA-PKcs.

Third, and perhaps most interesting, is the propensity of DNA-PKcs-/- mice for development of hyperplastic polyps and aberrant crypt foci (ACF) in the intestine. These changes are considered preneoplastic lesions and carcinoma in situ-like lesions in carcinogen-treated rodents and in humans with a high risk for developing colorectal malignancy (23-27). Our results clearly show that inactivation of DNA-PKcs leads to hyperplasia, dysplasia of intestinal mucosa and production of aberrant crypt foci, suggesting a role of DNA-PKcs in tumor suppression.

Carcinogenesis is a complex, multistep process, involving multiple events occurring at molecular, cellular, and morphological levels. Because colon tumors evolve through well-defined morphological stages, an elegant model for colorectal tumorigenesis has been established (26). The development of colorectal tumors appears to be initiated by mutations at the APC tumor suppressor gene, which leads to the formation of benign adenomas. Sequential mutations in RAS, DCC and p53 tumor suppressor genes appear to complete the process, that finally result in progression from the benign to malignant state. Recent studies of two distinct hereditary syndromes, Familial Adenomatous Polyposis (FAP) and Hereditary Nonpolyposis Colorectal Cancer (HNPCC) (27) suggest that the genetic defect in FAP affects the rate of tumor initiation by disrupting the "gatekeeper" function of APC gene. In contrast, the defect in HNPCC largely affects tumor progression by targeting the genome guardian function of DNA mismatch repair genes (MMR). It is plausible that mutation in DNA-PKcs, in addition to alterations in APC gene, may affect the initiation of a colorectal tumor or result in a predisposition to such tumors. Alternatively, defect in DNA-PKcs may affect tumor progression, a "caretaker" role similar to that proposed for the MMR genes. It has been shown that DNA-PKcs phosphorylates many transcription factors in vitro (28-31), suggesting the involvement of DNA-PKcs in transcription regulation. Although it remains to be proven, it is likely that the potential tumor suppressor function of DNA-PKcs may be related to the transcription control activity of this kinase molecule. Further investigations should reveal how DNA- PKcs exerts its effect and why mutations in different components of the DNA-PK complex result in discrete phenotypes.

References for the Fourth Series of Experiments

1. Peterson, S. R., Kurimasa, A., Oshimura, M., Dynan, W. S., Bradbury, E. M. & Chen, D. J. (1995) *Proc. Natl. Acad. Sci. USA* 92, 3171-3174.
2. Blunt, T., Finnie, N. J., Taccioli, G. E., Smith, G. C. M., Demengeot, J., Gottlieb, T. M., Mizuta, R., Varghese, A. J., Alt, F. W., Jeggo, P. A., et al. (1995) Cell 80, 813-823.
3. Kirchgessner, C. U., Patil, C. K., evans, J. W., Cuomo, C. A., Fried, L. M., Carter, T., Oettinger, M. A. & Brown, J. M. (1995) Science 267, 1178-1183.
4. Chan, D. W. & Lees-Miller, S. P. (1996) *J. Biol, Chem.* 271, 8936-8941.
5. Suwa, A., Hirakata, M., Takeda, Y., Jesch, S. A., Mimori, T. & Hardin, J. A. (1994) *Proc. Natl. Acad. Sci. USA* 91, 6904-6908.
6. Yaneva, M., Kowalewski, T. & Lieber, M. R. (1997) *EMBO J.* 16, 5098-5112.
7. Hammarstein, 0. & Chu, G. (1998) *Proc. Natl. Acad. Sci. USA* 95, 525-530.
8. Danska, J. S., Holland, D. P., Mariathasan, S., Williams, K. M. & Guigos, C. J. (1996) *Mol. Cell. Biol.* 16, 5507-5517.
9. Araki, R., Fujimori, A., Hamatani, K. Mita, K. Saito, T., Mori, M., Fukumura, R., Morimyo, M., Muto, M., Itoh, M., et al. (1997) *Proc. Natl. Acad. Sci. USA* 94, 2438-2443.
10. Blunt, T., Gell, D., Fox, M., Taccioli, G. E., Lehman. A. R., Jackson, S. P. & Jeggo, P. A. (1996) *Proc. Natl. Acad. Sci. USA* 93, 10285-10290.
11. Jhappan, C., Morse III, H. C., Fleischmann, R. D., Gottesman, M. M. & Merlino, G. (1997) *Nat. Genet.* 17, 483-486.
12. Custer, R. P., Bosma, G. C. & Bosma, M. J. (1985) *Am. J. Pathol.* 120, 464-477.
13. Nussenzweig, A., Chen, C., da Costa Soares, V., Sanchez, M., Sokol, K., Nussenzweig, M. C. & Li, G. C. (1996) Nature (London) 382, 551-555.
14. Li, G. C., Ouyang, H., Li, X., Nagasawa, H., Little, J. B., Chen, D. J., Ling, C. C., Fuks, Z. & Cordon-Dardo, C. (1998) Mol. Cell 2, 1-8.
15. Peterson, S. R., Stackhouse, M., Waltman, M. J., Chen, F., Sato, K. & Chen, D. J. (1997) *J. Biol. Chem.* 272, 10227-10231.
16. Ouyang, H., Nussenzweig, A., Kurimasa, A., da Costa Soares, V., Li, X., Cordon-Cardo, C., Li, W., Cheong, N., Nussenzweig, M., Iliakis, G., et al. (1997) *J. Exp. Med.* 186, 921-929.
17. Carter, T., Vancurova, I., Sun, I., Lou, W. & DeLeon, S. (1990) *Mol. Cell. Biol.* 10, 6460-6471.
18. Serano, M., Lee, H.-W., Chin, L., Cordon-Cardo, C., Beach, D. & DePinho, R. A. (1996) *Cell* 85, 27-37.
19. Zhu, C., Bogue, M. A., Lim, D.-S., Hasty, P. & Roth, D. B. (1996) *Cell* 86, 379-389.
20. Gao, Y., Chaudhuri, J., Zhu, C., Davidson, L., Weaver, D. T. & Alt, F. W. (1998) *Immunity* 9, 367-376.
21. Taccioli, G. E., Amatucci, A. G., Beamish, H. J., Gell, D., Xiang, X. H., Torres Arzayus, M. I., Priestly, A., Jackson, S. P., Rothstein, A. M., Jeggo, P. A., et al. (1998) Immunity 9, 355-366.
22. Gu, Y., Seidl, K. J., Rathbun, G. A., Zhu, C., Manis, J. P., vander Stoep, N., Davidson, L., Cheng, H.-L., Sekiguchi, J. M., Frank, K., et al. (1997) *Immunity* 7, 653-665.
23. Moen, C. J. A., van der Valk, M. A., Bird, R. P., Augustinus, A. M. & Demant, P. (1996) *Cancer Res.* 56, 2382-2386.
24. Roncussi, L., Pedroni, M., Fante, R., Di Gregorio, C. & Ponz de Leon, M. (1993) *Cancer Res.* 53, 3726-3729.
25. Bird, R. P. (1995) *Cancer Lett.* 93, 55-71.
26. Vogelstein, B. & Kinzler, K. W. (1993) *Trends Genet.* 9, 138-141.
27. Kinzler, K. W. & Vogelstein, B. (1996) *Cell* 87, 159-170.
28. Yumoto, Y., Shirakawa, H., Yoshida, M., Suwa, A., Watanabe, F. & Teraoka, H. (1998) *J. Biochem. (Tokyo)* 124, 519-527.
29. Peterson, S. R., Jesch, S. A., Chamberlin, T. N., Dvir, A., Rabindran, S. K., Wu, C. & Dynan, W. S. (1995) *J. Biol. Chem.* 20, 1449-1254.
30. Pan, Z. Q., Amin, A. A. Gibbs, E., Niu, II. & Hurwitz, J. (1994) *Proc. Natl. Acad. Sci. USA* 91, 8343-8347.
31. Anderson, C. W. (1993) *Trends Biochem. Sci.* 18, 433-437.
32. Saito, T., Matsuda, Y., Ishii, H., Watanabe, F., Mori, M., Hayashi, A., Araki, R., Fujimori, A., Fukumura, R., Morimyo, M., et al. (1998) *Mamm. Genome* 9, 769-772.

---

What is claimed is;

1. A method for treating a tumor in a subject comprising administering to the subject by selectively introducing to the tumor an antisense nucleic acid having the sequence of a human Ku70 cDNA in the antisense orientation that specifically hybridizes to a nucleic acid encoding human Ku70 so as to prevent expression thereof, wherein (a) the antisense nucleic acid is administered in an amount sufficient to increase the sensitivity of the tumor to heat, chemical or radiation-induced DNA damage, and (b) the antisense nucleic acid is introduced into the subject via an adenoviral vector comprising an expression vector encoding the antisense nucleic acid under the control of a heat shock promoter.

2. The method of claim 1, further comprising administering to the subject a DNA-damaging agent.

3. The method of claim 2, wherein the DNA-damaging agent is adriamycin, bleomycin or etoposide.

4. The method of claim 2, wherein the DNA-damaging agent is ionizing radiation.

5. The method of claim 2, wherein the DNA-damaging agent induces double strand breaks.

6. A method for treating cancer in a subject comprising selectively introducing to the cancer in the subject an expression vector encoding an antisense nucleic acid having the sequence of a human Ku70 cDNA in the antisense orientation, under the control of a heat shock promoter, that specifically hybridizes to a nucleic acid encoding human Ku70 so as to prevent expression thereof, and inducing expression of the antisense nucleic acid, wherein (a) the antisense nucleic acid is expressed in the subject's cancer cells in an amount sufficient to increase the sensitivity of those cells to heat, chemical, or ionizing radiation-induced DNA damage, and (b) the expression vector is in the form of an adenovirus.

7. The method of claim 6, further comprising directing heat, ionizing radiation, or chemotherapy at the site of cancer.

8. The method of claim 3, further comprising applying electric field energy to the site of cancer.

9. The method of claim 8, wherein the electric field energy comprises radiofrequency radiation.

10. The method of claim 6, further comprising implanting a reservoir of one or more chemotherapeutic agents near a site of cancer, wherein the chemotherapeutic agents are releasable over a period of time of at least eight hours.

* * * * *